(12) United States Patent
Whittingham et al.

(10) Patent No.: US 7,166,621 B2
(45) Date of Patent: Jan. 23, 2007

(54) PYRIDYLOXYALKANOIC ACID AMIDE DERIVATIVES USEFUL AS FUNGICIDES

(75) Inventors: William Guy Whittingham, Bracknell (GB); Kevin Robert Lawson, Bracknell (GB); Paul Anthony Worthington, Bracknell (GB); Charles Adam Russell, Bracknell (GB); Roger Salmon, Bracknell (GB); Leslie Francis May, Bracknell (GB); Mario Jorg, Basel (CH); Johannes Paul Pachlatko, Basel (CH)

(73) Assignees: Syngenta Limited, Guilford (GB); Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/497,627

(22) PCT Filed: Nov. 25, 2002

(86) PCT No.: PCT/GB02/05303

§ 371 (c)(1),
(2), (4) Date: Nov. 5, 2004

(87) PCT Pub. No.: WO03/048128

PCT Pub. Date: Jun. 12, 2003

(65) Prior Publication Data

US 2005/0065032 A1    Mar. 24, 2005

(30) Foreign Application Priority Data

Dec. 6, 2001  (GB) ................... 0129267.1

(51) Int. Cl.
*A01N 43/00* (2006.01)
*C07D 213/64* (2006.01)
*C07D 213/65* (2006.01)
*C07D 213/70* (2006.01)

(52) U.S. Cl. .................. 514/345; 514/277; 514/351; 546/290; 546/300; 546/302

(58) Field of Classification Search ................ 546/290, 546/300, 302; 514/277, 345, 351; 504/116
See application file for complete search history.

(56) References Cited

U.S. PATENT DOCUMENTS 4,116,677 A * 9/1978 Walker et al. ............... 504/338
4,168,319 A * 9/1979 Walker et al. ............... 514/622
6,090,815 A * 7/2000 Masuda et al. ........... 514/258.1

FOREIGN PATENT DOCUMENTS

WO    9933810    7/1999

* cited by examiner

Primary Examiner—Sabiha N. Qazi
(74) Attorney, Agent, or Firm—Jacqueline Haley

(57) ABSTRACT

Fungicidal compounds of the general formula (I): wherein X and Y are independently H, halo, $C_{1-8}$ alkyl, $C_{3-6}$ cycloalkyl, $C_{2-8}$ alkenyl, $C_{2-8}$ alkynyl, $C_{1-8}$ alkoxy, $C_{1-8}$ alkylthio, nitro, amino, mono- or di-($C_{1-6}$)alkylamino, mono- or di-($C_{2-6}$) alkenylamino, mono- or di-($C_{2-6}$)alkynylamino, formylamino, $C_{1-4}$ alkyl(formyl)amino, $C_{1-4}$ alkylcarbonylamino, $C_{1-4}$ alkyl($C_{1-4}$ alkylcarbonyl)amino, cyano, formyl, $C_{1-4}$ alkylcarbonyl, $C_{1-4}$ alkoxycarbonyl, aminocarbonyl, mono- or di-($C_{1-4}$)alkylaminocarbonyl, carboxy, $C_{1-4}$ alkylcarbonyloxy, aryl($C_{1-4}$)alkylcarbonyloxy, $C_{1-4}$ alkylsulphinyl, $C_{1-4}$ alkylsulphonyl, $C_{1-4}$ alkylsulphonyloxy, aryl, heteroaryl, aryloxy, arylthio, heteroaryloxy or heteroarylthio wherein any of the foregoing alkyl, cycloalkyl, alkenyl, alkynyl, aryl, heteroaryl, groups or moieties are optionally substituted; $R^1$ is phenyl, cyano, $C_{1-4}$ alkyl, $C_{2-4}$ alkenyl or $C_{2-4}$ alkynyl in which the alkyl, alkenyl and alkynyl groups are optionally substituted on their terminal carbon atom with one, two or three halogen atoms, with a cyano group, with a $C_{1-4}$ alkylcarbonyl group, with a $C_{1-4}$ alkoxycarbonyl group or with a hydroxy group, or $R^1$ is alkoxyalkyl, alkylthioalkyl, alkylsulphinylalkyl or alkylsulphonylalkyl in which the total number of carbon atoms is 2 or 3; $R^2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy; $R^3$ and $R^4$ are independently H, $C_{1-3}$ alkyl, $C_{2-3}$ alkenyl or $C_{2-3}$ alkynyl provided that both are not H and that when both are other than H their combined total of carbon atoms does not exceed 4, or $R^3$ and $R^4$ join with the carbon atom to which they are attached to form a 3 or 4 membered carbocyclic ring optionally containing one O, S or N atom and optionally substituted with halo or $C_{1-4}$ alkyl; and $R^5$ is halo, $C_{1-4}$ alkyl or $C_{3-4}$ cycloalkyl in which the alkyl or cycloalkyl group is optionally substituted with halo, hydroxy, $C_{1-6}$ alkoxy, $C_{1-6}$ alkylthio, cyano, $C_{1-4}$ alkylcarbonyloxy, aminocarbonyloxy, mono- or di($C_{1-4}$)alkylaminocarbonyloxy, or tri($C_{1-4}$)alkylsilyloxy. The compounds and compositions containing them are especially useful for combating fungal infections of plants.

5 Claims, No Drawings

PYRIDYLOXYALKANOIC ACID AMIDE DERIVATIVES USEFUL AS FUNGICIDES

This application is a 371 of International Application No. PCT/GB02/05303 filed Nov. 25, 2002, which claims priority to GB 0129267.1, filed Dec. 6, 2001, the contents of which are incorporated herein by reference.

This invention relates to novel pyridyloxyalkanoic acid amide derivatives, to processes for preparing them, to compositions containing them and to methods of using them to combat fungi, especially fungal infections of plants.

Certain pyridyl- and pyrimidinyloxy(thio)alkanoic acid amide derivatives are described in, for example, WO 99/33810 and U.S. Pat. No. 6,090,815 together with their use as agricultural and horticultural fungicides. In addition, certain phenoxyalkanoic acid amide derivatives are described in, for example, U.S. Pat. No. 4,116,677 and U.S. Pat. No. 4,168,319 together with their use as herbicides and mildewicides.

The present invention is concerned with the provision of alternative pyridyloxy-alkanoic acid amide derivatives for use as plant fungicides.

Thus, according to the present invention, there is provided a compound of the general formula (I):

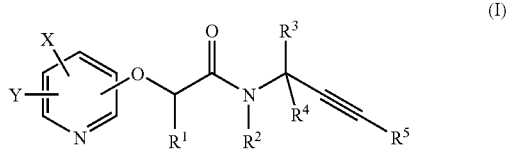

wherein X and Y are independently H, halo, $C_{1-8}$ alkyl, $C_{3-6}$ cycloalkyl, $C_{2-8}$ alkenyl, $C_{2-8}$ alkynyl, $C_{1-8}$ alkoxy, $C_{1-8}$ alkylthio, nitro, amino, mono- or di-($C_{1-6}$)alkylamino, mono- or di-($C_{2-6}$)alkenylamino, mono- or di-($C_{2-6}$)alkynylamino, formylamino, $C_{1-4}$ alkyl(formyl)amino, $C_{1-4}$ alkylcarbonylamino, $C_{1-4}$ alkyl($C_{1-4}$ alkylcarbonyl)amino, cyano, formyl, $C_{1-4}$ alkylcarbonyl, $C_{1-4}$ alkoxycarbonyl, aminocarbonyl, mono- or di-($C_{1-4}$)alkylaminocarbonyl, carboxy, $C_{1-4}$ alkylcarbonyloxy, aryl($C_{1-4}$)alkylcarbonyloxy, $C_{1-4}$ alkylsulphinyl, $C_{1-4}$ alkylsulphonyl, $C_{1-4}$ alkylsulphonyloxy, aryl, heteroaryl, aryloxy, arylthio, heteroaryloxy or heteroarylthio wherein any of the foregoing alkyl, cycloalkyl, alkenyl, alkynyl, aryl, heteroaryl, groups or moieties are optionally substituted; $R^1$ is phenyl, cyano, $C_{1-4}$ alkyl, $C_{2-4}$ alkenyl or $C_{2-4}$ alkynyl in which the alkyl, alkenyl and alkynyl groups are optionally substituted on their terminal carbon atom with one, two or three halogen atoms (e.g. 2-fluoroethyl, 2-chloroethyl, 2,2-difluoroethyl and 2,2,2-trifluoroethyl), with a cyano group (e.g. cyanomethyl), with a $C_{1-4}$ alkylcarbonyl group (e.g. acetylmethyl), with a $C_{1-4}$ alkoxycarbonyl group (e.g. methoxycarbonylmethyl and methoxycarbonylethyl) or with a hydroxy group (e.g. hydroxymethyl), or $R^1$ is alkoxyalkyl, alkylthioalkyl, alkylsulphinylalkyl or alkylsulphonylalkyl in which the total number of carbon atoms is 2 or 3 (e.g. methoxymethyl, methylthiomethyl, ethoxymethyl, 1-methoxyethyl and 2-methoxyethyl); $R^2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy; $R^3$ and $R^4$ are independently H, $C_{1-3}$ alkyl, $C_{2-3}$ alkenyl or $C_{2-3}$ alkynyl provided that both are not H and that when both are other than H their combined total of carbon atoms does not exceed 4, or $R^3$ and $R^4$ join with the carbon atom to which they are attached to form a 3 or 4 membered carbocyclic ring optionally containing one O, S or N atom and optionally substituted with halo or $C_{1-4}$ alkyl; and $R^5$ is halo, $C_{1-4}$ alkyl or $C_{3-6}$ cycloalkyl in which the alkyl or cycloalkyl group is optionally substituted with halo, hydroxy, $C_{1-6}$ alkoxy, $C_{1-6}$ alkylthio, cyano, $C_{1-4}$ alkylcarbonyloxy, aminocarbonyloxy, mono- or di($C_{1-4}$)alkylaminocarbonyloxy or tri($C_{1-4}$)alkylsilyloxy.

The compounds of the invention contain at least one asymmetric carbon atom (and at least two when $R^3$ and $R^4$ are different) and may exist as enantiomers (or as pairs of diastereoisomers) or as mixtures of such. However, these mixtures may be separated into individual isomers or isomer pairs, and this invention embraces such isomers and mixtures thereof in all proportions. It is to be expected that for any given compound, one isomer may be more fungicidally active than another.

Except where otherwise stated, alkyl groups and alkyl moieties of alkoxy, alkylamino, etc., suitably contain from 1 to 6, typically from 1 to 4, carbon atoms in the form of straight or branched chains. Examples are methyl, ethyl, n- and iso-propyl, n-, sec-, iso- and tert-butyl, n-pentyl and n-hexyl. Examples of suitable optional substituents of alkyl groups and moieties include halo, hydroxy, $C_{1-4}$ alkoxy and $C_{1-4}$ alkoxy($C_{1-4}$)alkoxy, optionally substituted aryl and optionally substituted heteroaryl. Where the optional substituent is halo, the haloalkyl group or moiety is typically trichloromethyl or trifluoromethyl.

Alkenyl and alkynyl moieties also suitably contain from 2 to 6, typically from 2 to 4, carbon atoms in the form of straight or branched chains. Examples are allyl, ethynyl and propargyl. Optional substituents include halo.

Halo includes fluoro, chloro, bromo and iodo. Most commonly it is fluoro, chloro or bromo.

Aryl is usually phenyl but also includes naphthyl, anthryl and phenanthryl.

Heteroaryl is typically a 5- or 6-membered aromatic ring containing one or more O, N or S heteroatoms, which may be fused to one or more other aromatic or heteroaromatic rings, such as a benzene ring. Examples are thienyl, furyl, pyrrolyl, isoxazolyl, oxazolyl, oxadiazolyl, pyrazolyl, imidazolyl, triazolyl, isothiazolyl, tetrazolyl, thiadiazolyl, pyridyl, pyrimidinyl, pyrazinyl, pyridazinyl, triazinyl, benzofuryl, benzothienyl, dibenzofuryl, benzothiazolyl, benzoxazolyl, benzimidazolyl, indolyl, quinolinyl and quinoxalinyl groups and, where appropriate, N-oxides and salts thereof.

Any of the aryl or heteroaryl values are optionally substituted. Except where otherwise stated, substituents which may be present include one or more of the following: halo, hydroxy, mercapto, $C_{1-8}$ alkyl (especially methyl and ethyl), $C_{2-6}$ alkenyl (especially allyl), $C_{2-6}$ alkynyl (especially propargyl), $C_{1-6}$ alkoxy (especially methoxy), $C_{2-6}$ alkenyloxy (especially allyloxy), $C_{2-6}$ alkynyloxy (especially propargyloxy), halo($C_{1-8}$)alkyl (especially trifluoromethyl), halo($C_{1-6}$)alkoxy (especially trifluoromethoxy), $C_{1-6}$ alkylthio (especially methylthio), hydroxy($C_{1-6}$)alkyl, $C_{1-4}$ alkoxy($C_{1-4}$)alkyl, $C_{1-4}$alkoxy($C_{1-4}$)alkoxy, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridyl or pyrimidinyl), optionally substituted aryloxy (especially optionally substituted phenoxy), optionally substituted heteroaryloxy (especially optionally substituted pyridyloxy or pyrimidinyloxy), optionally substituted arylthio (especially optionally substituted phenylthio), optionally substituted heteroarylthio (especially optionally substituted pyridylthio or pyrimidinylthio), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridyl- or pyrimidinyl-($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridylethenyl or pyrimidinylethenyl), optionally substituted aryl($C_{1-4}$)alkoxy (especially optionally substituted benzyloxy and phenethyloxy), optionally substituted heteroaryl($C_{1-4}$)alkoxy (especially optionally substituted pyridyl- or pyrimidinyl($C_{1-4}$)alkoxy), optionally substituted aryloxy($C_{1-4}$)alkyl (especially phenoxymethyl), optionally substituted heteroaryloxy-($C_{1-4}$)alkyl (especially optionally substituted pyridyloxy or pyrimidinyloxy-($C_{1-4}$)alkyl), optionally substituted aryl($C_{1-4}$)alkylthio (especially optionally substituted benzylthio and phenethylthio), optionally substituted heteroaryl($C_{1-4}$)alkylthio (especially optionally substituted pyridyl or pyrimidinyl($C_{1-4}$)alkylthio), optionally substituted arylthio($C_{1-4}$)alkyl (especially phenylthiomethyl), optionally substituted heteroarylthio-($C_{1-4}$)alkyl (especially optionally substituted pyridylthio- or pyrimidinylthio($C_{1-4}$)alkyl), acyloxy, including $C_{1-4}$ alkanoyloxy (especially acetyloxy) and benzoyloxy, cyano, isocyano, thiocyanato, isothiocyanato, nitro, NR'R", —NHCOR', —NHCONR'R", —CONR'R", —COOR', —SO$_2$R', —OSO$_2$R', —COR', —CR'=NR" or —N=CR'R" in which R' and R" are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Substituents which may be present in the aryl or heteroaryl rings of any of the foregoing substituents include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkyloxy, halo-($C_{1-4}$)alkyl, halo($C_{1-4}$)alkoxy, $C_{1-4}$ alkylthio, halo($C_{1-4}$)alkylthio, hydroxy($C_{1-4}$)alkyl, $C_{1-4}$alkoxy($C_{1-4}$)alkyl, $C_{3-6}$ cycloalkyl, $C_{3-6}$ cycloalkyl ($C_{1-4}$)alkyl, alkanoyloxy, phenoxy, benzyloxy, benzoyloxy, cyano, isocyano, thiocyanato, isothiocyanato, nitro, —NR'R", —NHCOR', —NHCONR'R", —CONR'R", —COOR', —SO$_2$R', —OSO$_2$R', —COR', —CR'=NR" or —N=CR'R", in which R' and R" have the meanings given above.

The alkanoic acid amide side chain in the compound of general formula (I) may be attached to the pyridine ring at the 2-, 3- or 4-position. Preferably it is attached to the 3- or 4-position and more preferably to the 3-position.

$R^1$ is preferably methyl, ethyl, n-propyl, methoxymethyl, allyl or propargyl, and more preferably ethyl, n-propyl or methoxymethyl. Also of particular interest are compounds where $R^1$ is 2-fluoroethyl, 2-chloroethyl, 2,2-difluoroethyl and 2,2,2-trifluoroethyl, vinyl, ethynyl, allyl, prop-1-enyl, propargyl, prop-1-ynyl, cyano, cyanomethyl and phenyl.

$R^2$ is preferably H, methyl, ethyl, n-propyl, methoxymethyl, ethoxymethyl or benzyloxymethyl and more preferably H.

$R^3$ and $R^4$ are, for example, both methyl or methyl and ethyl, or $R^3$ and $R^4$ join with the carbon atom to which they are attached to form cyclopropyl.

$R^5$ is preferably halo (especially fluoro or chloro), $C_{1-4}$ alkyl (especially methyl), hydroxy($C_{1-4}$)alkyl (especially hydroxymethyl) or $C_{1-4}$ alkoxy($C_{1-4}$)alkyl (especially methoxymethyl, ethoxymethyl and 1-methoxyethyl).

In one aspect, the invention provides a compound of the general formula (I) wherein X and Y are independently H, halo, $C_{1-8}$ alkyl, $C_{3-6}$ cycloalkyl, $C_{2-8}$ alkenyl, $C_{2-8}$ alkynyl, $C_{1-8}$ alkoxy, $C_{1-8}$ alkylthio, nitro, amino, mono- or di-($C_{1-6}$)alkylamino, mono- or di-($C_{2-6}$)alkenylamino, mono- or di-($C_{2-6}$)alkynylamino, formylamino, $C_{1-4}$ alkyl(formyl)amino, $C_{1-4}$ alkylcarbonylamino, $C_{1-4}$ alkyl($C_{1-4}$ alkylcarbonyl)amino, cyano, formyl, $C_{1-4}$ alkylcarbonyl, $C_{1-4}$ alkoxycarbonyl, aminocarbonyl, mono- or di-($C_{1-4}$) alkylaminocarbonyl, carboxy, $C_{1-4}$ alkylcarbonyloxy, aryl ($C_{1-4}$)alkylcarbonyloxy, $C_{1-4}$ alkylsulphinyl, $C_{1-4}$ alkylsulphonyl, $C_{1-4}$ alkylsulphonyloxy, aryl, heteroaryl, aryloxy, arylthio, heteroaryloxy or heteroarylthio wherein any of the foregoing alkyl, cycloalkyl, alkenyl, alkynyl, aryl, heteroaryl, groups or moieties are optionally substituted; $R^1$ is phenyl, cyano, $C_{2-3}$ alkenyl, $C_{2-3}$ alkynyl or $C_{1-3}$ alkyl optionally substituted with fluoro, cyano or $C_{1-2}$ alkoxy, provided that when $R^1$ is alkoxyalkyl it contains no more than 3 carbon atoms; $R^2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy; $R^3$ and $R^4$ are independently H, $C_{1-3}$ alkyl, $C_{2-3}$ alkenyl or $C_{2-3}$ alkynyl provided that both are not H and that when both are other than H their combined total of carbon atoms does not exceed 4, or $R^3$ and $R^4$ join with the carbon atom to which they are attached to form a 3 or 4 membered carbocyclic ring optionally containing one O, S or N atom; and $R^5$ is halo, $C_{1-4}$ alkyl or $C_{3-4}$ cycloalkyl in which the alkyl or cycloalkyl group is optionally substituted with halo, $C_{1-4}$ alkoxy, cyano, $C_{1-4}$ alkylcarbonyloxy, aminocarbonyloxy or mono- or di($C_{1-4}$)alkylaminocarbonyloxy.

In another aspect, the invention provides a compound of the general formula (I) wherein X and Y have the meanings given hereinbefore; $R^1$ is methyl, ethyl, n-propyl, methoxymethyl, allyl or propargyl; $R^2$ is H, methyl, ethyl, n-propyl, methoxymethyl, ethoxymethyl or benzyloxymethyl; $R^3$ and $R^4$ are both methyl or methyl and ethyl, or $R^3$ and $R^4$ join with the carbon atom to which they are attached to form cyclopropyl; and $R^5$ is halo, $C_{1-4}$ alkyl, hydroxy($C_{1-4}$)alkyl or $C_{1-4}$ alkoxy($C_{1-4}$)alkyl. $R^5$ is preferably methyl, hydroxymethyl, methoxymethyl, methoxymethyl, 1-methoxyethyl or chloro.

Typically, in the compound of the general formula (I), X is H and Y is halo, $C_{1-4}$ alkyl, cyclopropyl, $C_{2-4}$ alkenyl, $C_{2-4}$ alkynyl, $C_{1-4}$ alkoxy, $C_{1-4}$ alkylthio, nitro, amino, mono- or di-($C_{1-4}$)alkylamino, formylamino, $C_{1-4}$ alkyl(formyl)amino, $C_{1-4}$ alkylcarbonylamino, $C_{1-4}$ alkyl($C_{1-4}$ alkylcarbonyl)amino, cyano, formyl, $C_{1-4}$ alkylcarbonyl, $C_{1-4}$ alkoxycarbonyl, aminocarbonyl, mono- or di($C_{1-4}$) alkylaminocarbonyl, carboxy, $C_{1-4}$ alkylcarbonyloxy, phenyl($C_{1-4}$)alkylcarbonyloxy, $C_{1-4}$ alkylsulphinyl, $C_{1-4}$ alkylsulphonyl, $C_{1-4}$ alkylsulphonyloxy, phenyl, heteroaryl, phenoxy, phenylthio, heteroaryloxy or heteroarylthio wherein any of the foregoing alkyl, cycloalkyl, alkenyl or alkynyl groups or moieties are optionally substituted with halo, hydroxy or $C_{1-4}$ alkoxy and any of the foregoing phenyl or heteroaryl groups or moieties are optionally substituted with halo, $C_{1-4}$ alkyl, $C_{1-4}$ alkoxy, nitro or cyano and heteroaryl is furyl, thienyl, pyridyl or pyrimidinyl. An example of $C_{1-4}$ alkylcarbonylamino is methylcarbonylamino and an example of substituted $C_{1-4}$ alkylsulphonyloxy is trifluoromethylsulphonyloxy.

Thus, in another aspect, the invention provides a compound of the general formula (I) wherein $R^1$ is methyl, ethyl, n-propyl, methoxymethyl, allyl or propargyl; $R^2$ is H, methyl, ethyl, n-propyl, methoxymethyl, ethoxymethyl or benzyloxymethyl; $R^3$ and $R^4$ are both methyl or methyl and ethyl, or $R^3$ and $R^4$ join with the carbon atom to which they are attached to form cyclopropyl; $R^5$ is halo (especially chloro), $C_{1-4}$ alkyl (especially methyl), hydroxy($C_{1-4}$)alkyl (especially hydroxymethyl) or $C_{1-4}$ alkoxy($C_{1-4}$)alkyl (especially methoxymethyl, ethoxymethyl or 1-methoxyethyl); X is H; and Y is halo, $C_{1-4}$ alkyl, cyclopropyl, $C_{2-4}$ alkenyl, $C_{2-4}$ alkynyl, $C_{1-4}$ alkoxy, $C_{1-4}$ alkylthio, nitro, amino, mono or di-($C_{1-4}$)alkylamino, formylamino, $C_{1-4}$ alkyl(formyl)amino, $C_{1-4}$ alkylcarbonylamino, $C_{1-4}$ alkyl($C_{1-4}$ alkylcarbonyl)amino, cyano, formyl, $C_{1-4}$ alkylcarbonyl, $C_{1-4}$ alkoxycarbonyl, aminocarbonyl, mono- or di-($C_{1-4}$)alkylaminocarbonyl, carboxy, $C_{1-4}$ alkylcarbonyloxy, phenyl($C_{1-4}$)alkylcarbonyloxy, $C_{1-4}$ alkylsulphinyl, $C_{1-4}$ alkylsulphonyl, $C_{1-4}$ alkylsulphonyloxy, phenyl, heteroaryl, phenoxy, phenylthio, heteroaryloxy or heteroarylthio, wherein any of the foregoing alkyl, cycloalkyl, alkenyl or alkynyl groups or moieties which Y may be are optionally substituted with halo, hydroxy or $C_{1-4}$ alkoxy, any of the foregoing phenyl or heteroaryl groups or moieties which Y may be are optionally substituted with halo, $C_{1-4}$ alkyl, $C_{1-4}$ alkoxy, nitro or cyano and heteroaryl is furyl, thienyl, pyridyl or pyrimidinyl.

Preferably, in the general formula (I), the alkanoic acid amide side chain is attached to the pyridine ring at the 3-position.

In yet another aspect the invention provides a compound of general formula (I) wherein X is H, $C_{1-4}$ alkyl, halo ($C_{1-4}$)alkyl or CN; Y is H, halo, $C_{1-4}$ alkyl or halo($C_{1-4}$)alkyl; $R^1$ is methyl, ethyl, n-propyl or methoxymethyl; $R^2$ is H, methyl, ethyl or n-propyl, methoxymethyl or ethoxymethyl; $R^3$ and $R^4$ are both methyl or $R^3$ is methyl and $R^4$ is ethyl; $R^5$ is halo, $C_{1-4}$ alkyl, hydroxy($C_{1-4}$)alkyl or $C_{1-4}$ alkoxy($C_{1-4}$)alkyl; and the alkanoic acid amide side chain is attached to the 3-position of the pyridine ring.

In yet another aspect the invention provides a compound of general formula (I) wherein X is H, $C_{1-4}$ alkyl, halo ($C_{1-4}$)alkyl or CN; Y is H, halo, $C_{1-4}$ alkyl or halo($C_{1-4}$)alkyl; $R^1$ is methyl, ethyl, n-propyl or methoxymethyl; $R^2$ is H, methyl, ethyl or n-propyl, methoxymethyl or ethoxymethyl; $R^3$ and $R^4$ are both methyl or $R^3$ is methyl and $R^4$ is ethyl; $R^5$ is halo, $C_{1-4}$ alkyl, hydroxy($C_{1-4}$)alkyl or $C_{1-4}$ alkoxy($C_{1-4}$)alkyl; and the alkanoic acid amide side chain is attached to the 4-position of the pyridine ring.

Compounds that form part of the invention are illustrated in Tables 1 to 3 below. The compounds have the general formula (I) in which the values of X, Y, $R^1$, $R^2$, $R^3$, $R^4$ and $R^5$ are given in the tables. In Table 1 the alkanoic acid amide side chain is attached to the 3-position of the pyridine ring (3-pyridines); in Table 2 the alkanoic acid amide side chain is attached to the 4-position of the pyridine ring (4-pyridines); and in Table 3 the alkanoic acid amide side chain is attached to the 2-position of the pyridine ring (2-pyridines).

TABLE 1

3-Pyridines

| Compound No. | X | Y | $R^1$ | $R^2$ | $R^3$ | $R^4$ | $R^5$ | Melting Point (° C.) |
|---|---|---|---|---|---|---|---|---|
| 1 | H | 5-Cl | $C_2H_5$ | H | $CH_3$ | $CH_3$ | $C_2H_5$ | 94.0–95.5 |
| 2 | H | 5-Cl | $CH_3$ | H | $CH_3$ | $CH_3$ | $CH_3$ | 89–91 |
| 3 | H | 5-Cl | $n-C_3H_7$ | H | $CH_3$ | $CH_3$ | $CH_3$ | 73–75 |
| 4 | H | 5-Cl | $i-C_3H_7$ | H | $CH_3$ | $CH_3$ | $CH_3$ | oil |
| 5 | H | 5-Cl | $C_2H_5$ | H | $CH_3$ | $CH_3$ | Cl | 78–82 |
| 6 | H | 5-Cl | $C_2H_5$ | H | $CH_3$ | $CH_3$ | Br | oil |
| 7 | H | 5-Cl | $C_2H_5$ | H | $CH_3$ | $CH_3$ | I | 133–135 |
| 8 | H | 5-Cl | $C_2H_5$ | H | $CH_3$ | $CH_3$ | $CH_3$ | 87–89 |
| 9 | H | 5-Cl | $C_2H_5$ | $CH_2OC_2H_5$ | $CH_3$ | $CH_3$ | $CH_3$ | oil |
| 10 | H | 5-Cl | $C_2H_5$ | $CH_3$ | $CH_3$ | $CH_3$ | $CH_3$ | 67–68 |
| 11 | H | 5-Cl | $C_2H_5$ | H | $CH_3$ | $CH_3$ | $CH_3$ | 133.5–135.5 |
| 12 | 6-$CH_3$ | H | $C_2H_5$ | H | $CH_3$ | $CH_3$ | $CH_3$ | |
| 13 | H | 5-Br | $C_2H_5$ | H | $CH_3$ | $CH_3$ | $CH_3$ | 102–104 |
| 14 | H | 5-Br | $C_2H_5$ | H | $CH_3$ | $CH_3$ | $C_2H_5$ | 90–92 |
| 15 | H | 5-CON($i-C_3H_7$)$_2$ | $C_2H_5$ | H | $CH_3$ | $CH_3$ | $C_2H_5$ | gum |
| 16 | H | 5-$CO_2CH_3$ | $C_2H_5$ | H | $CH_3$ | $CH_3$ | $C_2H_5$ | oil |
| 17 | H | 5-$CO_2H$ | $C_2H_5$ | H | $CH_3$ | $CH_3$ | $C_2H_5$ | 162–164 |
| 18 | H | 5-Cl | $CH_2CH=CH_2$ | H | $CH_3$ | $CH_3$ | $CH_3$ | |
| 19 | H | 5-Cl | $CH_2C\equiv CH$ | H | $CH_3$ | $CH_3$ | $CH_3$ | |
| 20 | H | 5-Cl | $CH_2CF_3$ | H | $CH_3$ | $CH_3$ | $CH_3$ | |
| 21 | H | 5-Cl | $CH_2OCH_3$ | H | $CH_3$ | $CH_3$ | $CH_3$ | |
| 22 | H | 5-Cl | $CH_2CN$ | H | $CH_3$ | $CH_3$ | $CH_3$ | |
| 23 | H | 5-Cl | $CH_3$ | H | $CH_3$ | $CH_3$ | $C_2H_5$ | |
| 24 | H | 5-Cl | $n-C_3H_7$ | H | $CH_3$ | $CH_3$ | $C_2H_5$ | |
| 25 | H | 5-Cl | $CH_2CH=CH_2$ | H | $CH_3$ | $CH_3$ | $C_2H_5$ | |
| 26 | H | 5-Cl | $CH_2C\equiv CH$ | H | $CH_3$ | $CH_3$ | $C_2H_5$ | |
| 27 | H | 5-Cl | $CH_2CF_3$ | H | $CH_3$ | $CH_3$ | $C_2H_5$ | |
| 28 | H | 5-Cl | $CH_2OCH_3$ | H | $CH_3$ | $CH_3$ | $C_2H_5$ | |
| 29 | H | 5-Cl | $CH_2CN$ | H | $CH_3$ | $CH_3$ | $C_2H_5$ | |
| 30 | H | 5-Cl | $C_6H_5$ | H | $CH_3$ | $CH_3$ | $C_2H_5$ | |
| 31 | H | 5-Cl | $CH_3$ | H | $CH_3$ | $CH_3$ | cyclopropyl | |
| 32 | H | 5-Cl | $C_2H_5$ | H | $CH_3$ | $CH_3$ | cyclopropyl | |
| 33 | H | 5-Cl | $n-C_3H_7$ | H | $CH_3$ | $CH_3$ | cyclopropyl | |
| 34 | H | 5-Cl | $CH_2CH=CH_2$ | H | $CH_3$ | $CH_3$ | cyclopropyl | |
| 35 | H | 5-Cl | $CH_2C\equiv CH$ | H | $CH_3$ | $CH_3$ | cyclopropyl | |
| 36 | H | 5-Cl | $CH_2CF_3$ | H | $CH_3$ | $CH_3$ | cyclopropyl | |
| 37 | H | 5-Cl | $CH_2OCH_3$ | H | $CH_3$ | $CH_3$ | cyclopropyl | |
| 38 | H | 5-Cl | $CH_2CN$ | H | $CH_3$ | $CH_3$ | cyclopropyl | |
| 39 | H | 5-Cl | $C_6H_5$ | H | $CH_3$ | $CH_3$ | cyclopropyl | |

TABLE 1-continued

3-Pyridines

| Compound No. | X | Y | $R^1$ | $R^2$ | $R^3$ | $R^4$ | $R^5$ | Melting Point (° C.) |
|---|---|---|---|---|---|---|---|---|
| 40 | H | 5-Cl | $CH_3$ | H | $CH_3$ | $CH_3$ | $CH_2CF_3$ | |
| 41 | H | 5-Cl | $C_2H_5$ | H | $CH_3$ | $CH_3$ | $CH_2CF_3$ | |
| 42 | H | 5-Cl | $CH_2CH=CH_2$ | H | $CH_3$ | $CH_3$ | $CH_2CF_3$ | |
| 43 | H | 5-Cl | $CH_2C\equiv CH$ | H | $CH_3$ | $CH_3$ | $CH_2CF_3$ | |
| 44 | H | 5-Cl | $CH_2CF_3$ | H | $CH_3$ | $CH_3$ | $CH_2CF_3$ | |
| 45 | H | 5-Cl | $CH_2OCH_3$ | H | $CH_3$ | $CH_3$ | $CH_2CF_3$ | |
| 46 | H | 5-Cl | $CH_2CN$ | H | $CH_3$ | $CH_3$ | $CH_2CF_3$ | |
| 47 | H | 5-Cl | $C_6H_5$ | H | $CH_3$ | $CH_3$ | $CH_2CF_3$ | |
| 48 | H | 5-Cl | $CH_3$ | H | $CH_3$ | $CH_3$ | $CH_2OCH_3$ | |
| 49 | H | 5-Cl | $C_2H_5$ | H | $CH_3$ | $CH_3$ | $CH_2OCH_3$ | |
| 50 | H | 5-Cl | $CH_2CH=CH_2$ | H | $CH_3$ | $CH_3$ | $CH_2OCH_3$ | |
| 51 | H | 5-Cl | $CH_2C\equiv CH$ | H | $CH_3$ | $CH_3$ | $CH_2OCH_3$ | |
| 52 | H | 5-Cl | $CH_2CF_3$ | H | $CH_3$ | $CH_3$ | $CH_2OCH_3$ | |
| 53 | H | 5-Cl | $CH_2OCH_3$ | H | $CH_3$ | $CH_3$ | $CH_2OCH_3$ | |
| 54 | H | 5-Cl | $CH_2CN$ | H | $CH_3$ | $CH_3$ | $CH_2OCH_3$ | |
| 55 | H | 5-Cl | $C_6H_5$ | H | $CH_3$ | $CH_3$ | $CH_2OCH_3$ | |
| 56 | H | 5-Cl | $CH_3$ | $CH_3$ | $CH_3$ | $CH_3$ | $CH_3$ | |
| 57 | H | 5-Cl | $CH_2CH=CH_2$ | $CH_3$ | $CH_3$ | $CH_3$ | $CH_3$ | |
| 58 | H | 5-Cl | $CH_2C\equiv CH$ | $CH_3$ | $CH_3$ | $CH_3$ | $CH_3$ | |
| 59 | H | 5-Cl | $CH_2CF_3$ | $CH_3$ | $CH_3$ | $CH_3$ | $CH_3$ | |
| 60 | H | 5-Cl | $CH_2OCH_3$ | $CH_3$ | $CH_3$ | $CH_3$ | $CH_3$ | |
| 61 | H | 5-Cl | $CH_2CN$ | $CH_3$ | $CH_3$ | $CH_3$ | $CH_3$ | |
| 62 | H | 5-Cl | $C_6H_5$ | $CH_3$ | $CH_3$ | $CH_3$ | $CH_3$ | |
| 63 | H | 5-Cl | $CH_3$ | $CH_3$ | $CH_3$ | $CH_3$ | $C_2H_5$ | |
| 64 | H | 5-Cl | $C_2H_5$ | $CH_3$ | $CH_3$ | $CH_3$ | $C_2H_5$ | |
| 65 | H | 5-Cl | $CH_2CH=CH_2$ | $CH_3$ | $CH_3$ | $CH_3$ | $C_2H_5$ | |
| 66 | H | 5-Cl | $CH_2C\equiv CH$ | $CH_3$ | $CH_3$ | $CH_3$ | $C_2H_5$ | |
| 67 | H | 5-Cl | $CH_2CF_3$ | $CH_3$ | $CH_3$ | $CH_3$ | $C_2H_5$ | |
| 68 | H | 5-Cl | $CH_2OCH_3$ | $CH_3$ | $CH_3$ | $CH_3$ | $C_2H_5$ | |
| 69 | H | 5-Cl | $CH_2CN$ | $CH_3$ | $CH_3$ | $CH_3$ | $C_2H_5$ | |
| 70 | H | 5-Cl | $C_6H_5$ | $CH_3$ | $CH_3$ | $CH_3$ | $C_2H_5$ | |
| 71 | H | 5-Cl | $CH_3$ | $CH_2OC_2H_5$ | $CH_3$ | $CH_3$ | $CH_3$ | |
| 72 | H | 5-Cl | $n-C_3H_7$ | $CH_2OC_2H_5$ | $CH_3$ | $CH_3$ | $CH_3$ | |
| 73 | H | 5-Cl | $CH_2CH=CH_2$ | $CH_2OC_2H_5$ | $CH_3$ | $CH_3$ | $CH_3$ | |
| 74 | H | 5-Cl | $CH_2C\equiv CH$ | $CH_2OC_2H_5$ | $CH_3$ | $CH_3$ | $CH_3$ | |
| 75 | H | 5-Cl | $CH_2CF_3$ | $CH_2OC_2H_5$ | $CH_3$ | $CH_3$ | $CH_3$ | |
| 76 | H | 5-Cl | $CH_2OCH_3$ | $CH_2OC_2H_5$ | $CH_3$ | $CH_3$ | $CH_3$ | |
| 77 | H | 5-Cl | $CH_2CN$ | $CH_2OC_2H_5$ | $CH_3$ | $CH_3$ | $CH_3$ | |
| 78 | H | 5-Cl | $C_6H_5$ | $CH_2OC_2H_5$ | $CH_3$ | $CH_3$ | $CH_3$ | |
| 79 | H | 5-Cl | $CH_3$ | $CH_2OC_2H_5$ | $CH_3$ | $CH_3$ | $C_2H_5$ | |
| 80 | H | 5-Cl | $C_2H_5$ | $CH_2OC_2H_5$ | $CH_3$ | $CH_3$ | $C_2H_5$ | |
| 81 | H | 5-Cl | $CH_2CH=CH_2$ | $CH_2OC_2H_5$ | $CH_3$ | $CH_3$ | $C_2H_5$ | |
| 82 | H | 5-Cl | $CH_2C\equiv CH$ | $CH_2OC_2H_5$ | $CH_3$ | $CH_3$ | $C_2H_5$ | |
| 83 | H | 5-Cl | $CH_2CF_3$ | $CH_2OC_2H_5$ | $CH_3$ | $CH_3$ | $C_2H_5$ | |
| 84 | H | 5-Cl | $CH_2OCH_3$ | $CH_2OC_2H_5$ | $CH_3$ | $CH_3$ | $C_2H_5$ | |
| 85 | H | 5-Cl | $CH_2CN$ | $CH_2OC_2H_5$ | $CH_3$ | $CH_3$ | $C_2H_5$ | |
| 86 | H | 5-Cl | $C_6H_5$ | $CH_2OC_2H_5$ | $CH_3$ | $CH_3$ | $C_2H_5$ | |
| 87 | H | 5-Cl | $CH_3$ | H | $CH_2CH=CH_2$ | $CH_3$ | $CH_3$ | |
| 88 | H | 5-Cl | $C_2H_5$ | H | $CH_2CH=CH_2$ | $CH_3$ | $CH_3$ | |
| 89 | H | 5-Cl | $CH_2CH=CH_2$ | H | $CH_2CH=CH_2$ | $CH_3$ | $CH_3$ | |
| 90 | H | 5-Cl | $CH_2C\equiv CH$ | H | $CH_2CH=CH_2$ | $CH_3$ | $CH_3$ | |
| 91 | H | 5-Cl | $CH_2CF_3$ | H | $CH_2CH=CH_2$ | $CH_3$ | $CH_3$ | |
| 92 | H | 5-Cl | $CH_2OCH_3$ | H | $CH_2CH=CH_2$ | $CH_3$ | $CH_3$ | |
| 93 | H | 5-Cl | $CH_2CN$ | H | $CH_2CH=CH_2$ | $CH_3$ | $CH_3$ | |
| 94 | H | 5-Cl | $C_6H_5$ | H | $CH_2CH=CH_2$ | $CH_3$ | $CH_3$ | |
| 95 | H | 5-Cl | $CH_3$ | H | $CH_2CH=CH_2$ | $CH_3$ | $C_2H_5$ | |
| 96 | H | 5-Cl | $C_2H_5$ | H | $CH_2CH=CH_2$ | $CH_3$ | $C_2H_5$ | |
| 97 | H | 5-Cl | $CH_2CH=CH_2$ | H | $CH_2CH=CH_2$ | $CH_3$ | $C_2H_5$ | |
| 98 | H | 5-Cl | $CH_2C\equiv CH$ | H | $CH_2CH=CH_2$ | $CH_3$ | $C_2H_5$ | |
| 99 | H | 5-Cl | $CH_2CF_3$ | H | $CH_2CH=CH_2$ | $CH_3$ | $C_2H_5$ | |
| 100 | H | 5-Cl | $CH_2OCH_3$ | H | $CH_2CH=CH_2$ | $CH_3$ | $C_2H_5$ | |
| 101 | H | 5-Cl | $CH_2CN$ | H | $CH_2CH=CH_2$ | $CH_3$ | $C_2H_5$ | |
| 102 | H | 5-Cl | $C_6H_5$ | H | $CH_2CH=CH_2$ | $CH_3$ | $C_2H_5$ | |
| 103 | 6-$CH_3$ | 5-Cl | $CH_3$ | H | $CH_3$ | $CH_3$ | $CH_3$ | |
| 104 | 6-$CH_3$ | 5-Cl | $C_2H_5$ | H | $CH_3$ | $CH_3$ | $CH_3$ | |
| 105 | 6-$CH_3$ | 5-Cl | $CH_2CH=CH_2$ | H | $CH_3$ | $CH_3$ | $CH_3$ | |
| 106 | 6-$CH_3$ | 5-Cl | $CH_2C\equiv CH$ | H | $CH_3$ | $CH_3$ | $CH_3$ | |
| 107 | 6-$CH_3$ | 5-Cl | $CH_2CF_3$ | H | $CH_3$ | $CH_3$ | $CH_3$ | |
| 108 | 6-$CH_3$ | 5-Cl | $CH_2OCH_3$ | H | $CH_3$ | $CH_3$ | $CH_3$ | |
| 109 | 6-$CH_3$ | 5-Cl | $CH_2CN$ | H | $CH_3$ | $CH_3$ | $CH_3$ | |
| 110 | 6-$CH_3$ | 5-Cl | $C_6H_5$ | H | $CH_3$ | $CH_3$ | $CH_3$ | |
| 111 | 6-$CH_3$ | 5-Cl | $CH_3$ | H | $CH_3$ | $CH_3$ | $C_2H_5$ | |
| 112 | 6-$CH_3$ | 5-Cl | $C_2H_5$ | H | $CH_3$ | $CH_3$ | $C_2H_5$ | |
| 113 | 6-$CH_3$ | 5-Cl | $CH_2CH=CH_2$ | H | $CH_3$ | $CH_3$ | $C_2H_5$ | |

TABLE 1-continued

3-Pyridines

| Compound No. | X | Y | R$^1$ | R$^2$ | R$^3$ | R$^4$ | R$^5$ | Melting Point (° C.) |
|---|---|---|---|---|---|---|---|---|
| 114 | 6-CH$_3$ | 5-Cl | CH$_2$C≡CH | H | CH$_3$ | CH$_3$ | C$_2$H$_5$ | |
| 115 | 6-CH$_3$ | 5-Cl | CH$_2$CF$_3$ | H | CH$_3$ | CH$_3$ | C$_2$H$_5$ | |
| 116 | 6-CH$_3$ | 5-Cl | CH$_2$OCH$_3$ | H | CH$_3$ | CH$_3$ | C$_2$H$_5$ | |
| 117 | 6-CH$_3$ | 5-Cl | CH$_2$CN | H | CH$_3$ | CH$_3$ | C$_2$H$_5$ | |
| 118 | 6-CH$_3$ | 5-Cl | C$_6$H$_5$ | H | CH$_3$ | CH$_3$ | C$_2$H$_5$ | |
| 119 | H | 5-Cl | CH$_3$ | H | CH$_3$ | CH$_3$ | n-C$_3$H$_7$ | |
| 120 | H | 5-Cl | C$_2$H$_5$ | H | CH$_3$ | CH$_3$ | n-C$_3$H$_7$ | |
| 121 | H | 5-Cl | CH$_2$CH=CH$_2$ | H | CH$_3$ | CH$_3$ | n-C$_3$H$_7$ | |
| 122 | H | 5-Cl | CH$_2$C≡CH | H | CH$_3$ | CH$_3$ | n-C$_3$H$_7$ | |
| 123 | H | 5-Cl | CH$_2$CF$_3$ | H | CH$_3$ | CH$_3$ | n-C$_3$H$_7$ | |
| 124 | H | 5-Cl | CH$_2$OCH$_3$ | H | CH$_3$ | CH$_3$ | n-C$_3$H$_7$ | |
| 125 | H | 5-Cl | CH$_2$CN | H | CH$_3$ | CH$_3$ | n-C$_3$H$_7$ | |
| 126 | H | 5-Cl | C$_6$H$_5$ | H | CH$_3$ | CH$_3$ | n-C$_3$H$_7$ | |
| 127 | H | 5-Br | CH$_3$ | H | CH$_3$ | CH$_3$ | n-C$_3$H$_7$ | |
| 128 | H | 5-Br | C$_2$H$_5$ | H | CH$_3$ | CH$_3$ | n-C$_3$H$_7$ | |
| 129 | H | 5-Br | CH$_2$CH=CH$_2$ | H | CH$_3$ | CH$_3$ | n-C$_3$H$_7$ | |
| 130 | H | 5-Br | CH$_2$C≡CH | H | CH$_3$ | CH$_3$ | n-C$_3$H$_7$ | |
| 131 | H | 5-Br | CH$_2$CF$_3$ | H | CH$_3$ | CH$_3$ | n-C$_3$H$_7$ | |
| 132 | H | 5-Br | CH$_2$OCH$_3$ | H | CH$_3$ | CH$_3$ | n-C$_3$H$_7$ | |
| 133 | H | 5-Br | CH$_2$CN | H | CH$_3$ | CH$_3$ | n-C$_3$H$_7$ | |
| 134 | H | 5-Br | C$_6$H$_5$ | H | CH$_3$ | CH$_3$ | n-C$_3$H$_7$ | |
| 135 | H | 5-Cl | CH$_3$ | H | CH$_3$ | C$_2$H$_5$ | CH$_3$ | |
| 136 | H | 5-Cl | C$_2$H$_5$ | H | CH$_3$ | C$_2$H$_5$ | CH$_3$ | |
| 137 | H | 5-Cl | n-C$_3$H$_7$ | H | CH$_3$ | C$_2$H$_5$ | CH$_3$ | |
| 138 | H | 5-Cl | CH$_2$CH=CH$_2$ | H | CH$_3$ | C$_2$H$_5$ | CH$_3$ | |
| 139 | H | 5-Cl | CH$_2$C≡CH | H | CH$_3$ | C$_2$H$_5$ | CH$_3$ | |
| 140 | H | 5-Cl | CH$_2$CF$_3$ | H | CH$_3$ | C$_2$H$_5$ | CH$_3$ | |
| 141 | H | 5-Cl | CH$_2$OCH$_3$ | H | CH$_3$ | C$_2$H$_5$ | CH$_3$ | |
| 142 | H | 5-Cl | CH$_2$CN | H | CH$_3$ | C$_2$H$_5$ | CH$_3$ | |
| 143 | H | 5-Cl | C$_6$H$_5$ | H | CH$_3$ | C$_2$H$_5$ | CH$_3$ | |
| 144 | H | 5-Cl | CH$_3$ | H | CH$_3$ | C$_2$H$_5$ | C$_2$H$_5$ | |
| 145 | H | 5-Cl | C$_2$H$_5$ | H | CH$_3$ | C$_2$H$_5$ | C$_2$H$_5$ | |
| 146 | H | 5-Cl | CH$_2$CH=CH$_2$ | H | CH$_3$ | C$_2$H$_5$ | C$_2$H$_5$ | |
| 147 | H | 5-Cl | CH$_2$C≡CH | H | CH$_3$ | C$_2$H$_5$ | C$_2$H$_5$ | |
| 148 | H | 5-Cl | CH$_2$CF$_3$ | H | CH$_3$ | C$_2$H$_5$ | C$_2$H$_5$ | |
| 149 | H | 5-Cl | CH$_2$OCH$_3$ | H | CH$_3$ | C$_2$H$_5$ | C$_2$H$_5$ | |
| 150 | 6-Cl | 5-Cl | CH$_3$ | H | CH$_3$ | C$_2$H$_5$ | CH$_2$OSi(CH$_3$)$_2$(t-C$_4$H$_9$) | |
| 151 | 6-Cl | 5-Cl | C$_2$H$_5$ | H | CH$_3$ | C$_2$H$_5$ | CH$_2$OSi(CH$_3$)$_2$(t-C$_4$H$_9$) | |
| 152 | H | 5-Cl | CH$_3$ | H | CH$_3$ | C$_2$H$_5$ | cyclopropyl | |
| 153 | H | 5-Cl | C$_2$H$_5$ | H | CH$_3$ | C$_2$H$_5$ | cyclopropyl | |
| 154 | H | 5-Cl | CH$_2$CH=CH$_2$ | H | CH$_3$ | C$_2$H$_5$ | cyclopropyl | |
| 155 | H | 5-Cl | CH$_2$C≡CH | H | CH$_3$ | C$_2$H$_5$ | cyclopropyl | |
| 156 | H | 5-Cl | CH$_2$CF$_3$ | H | CH$_3$ | C$_2$H$_5$ | cyclopropyl | |
| 157 | H | 5-Cl | CH$_2$OCH$_3$ | H | CH$_3$ | C$_2$H$_5$ | cyclopropyl | |
| 158 | H | 5-Cl | CH$_3$ | H | CH$_3$ | CH$_3$ | CH$_2$OSi(CH$_3$)$_2$(t-C$_4$H$_9$) | |
| 159 | H | 5-Cl | C$_2$H$_5$ | H | CH$_3$ | CH$_3$ | CH$_2$OSi(CH$_3$)$_2$(t-C$_4$H$_9$) | |
| 160 | H | 5-Cl | CH$_3$ | H | CH$_3$ | C$_2$H$_5$ | CH$_2$CF$_3$ | |
| 161 | H | 5-Cl | C$_2$H$_5$ | H | CH$_3$ | C$_2$H$_5$ | CH$_2$CF$_3$ | |
| 162 | H | 5-Cl | CH$_2$CH=CH$_2$ | H | CH$_3$ | C$_2$H$_5$ | CH$_2$CF$_3$ | |
| 163 | H | 5-Cl | CH$_2$C≡CH | H | CH$_3$ | C$_2$H$_5$ | CH$_2$CF$_3$ | |
| 164 | H | 5-Cl | CH$_2$CF$_3$ | H | CH$_3$ | C$_2$H$_5$ | CH$_2$CF$_3$ | |
| 165 | H | 5-Cl | CH$_2$OCH$_3$ | H | CH$_3$ | C$_2$H$_5$ | CH$_2$CF$_3$ | |
| 166 | H | 5-Cl | CH$_2$CN | H | CH$_3$ | C$_2$H$_5$ | CH$_2$CF$_3$ | |
| 167 | H | 5-Cl | C$_6$H$_5$ | H | CH$_3$ | C$_2$H$_5$ | CH$_2$CF$_3$ | |
| 168 | H | 5-Cl | CH$_3$ | H | CH$_3$ | C$_2$H$_5$ | CH$_2$OCH$_3$ | |
| 169 | H | 5-Cl | C$_2$H$_5$ | H | CH$_3$ | C$_2$H$_5$ | CH$_2$OCH$_3$ | |
| 170 | H | 5-Cl | CH$_2$CH=CH$_2$ | H | CH$_3$ | C$_2$H$_5$ | CH$_2$OCH$_3$ | |
| 171 | H | 5-Cl | CH$_2$C≡CH | H | CH$_3$ | C$_2$H$_5$ | CH$_2$OCH$_3$ | |
| 172 | H | 5-Cl | CH$_2$CF$_3$ | H | CH$_3$ | C$_2$H$_5$ | CH$_2$OCH$_3$ | |
| 173 | H | 5-Cl | CH$_2$OCH$_3$ | H | CH$_3$ | C$_2$H$_5$ | CH$_2$OCH$_3$ | |
| 174 | H | 5-Cl | CH$_2$CN | H | CH$_3$ | C$_2$H$_5$ | CH$_2$OCH$_3$ | |
| 175 | H | 5-Cl | C$_6$H$_5$ | H | CH$_3$ | C$_2$H$_5$ | CH$_2$OCH$_3$ | |
| 176 | H | 5-Cl | CH$_3$ | H | CH$_3$ | CF$_3$ | CH$_3$ | |
| 177 | H | 5-Cl | C$_2$H$_5$ | H | CH$_3$ | CF$_3$ | CH$_3$ | |
| 178 | H | 5-Cl | CH$_2$CH=CH$_2$ | H | CH$_3$ | CF$_3$ | CH$_3$ | |
| 179 | H | 5-Cl | CH$_2$C≡CH | H | CH$_3$ | CF$_3$ | CH$_3$ | |
| 180 | H | 5-Cl | CH$_2$CF$_3$ | H | CH$_3$ | CF$_3$ | CH$_3$ | |
| 181 | H | 5-Cl | CH$_2$OCH$_3$ | H | CH$_3$ | CF$_3$ | CH$_3$ | |
| 182 | H | 5-Cl | CH$_2$CN | H | CH$_3$ | CF$_3$ | CH$_3$ | |
| 183 | H | 5-Cl | C$_6$H$_5$ | H | CH$_3$ | CF$_3$ | CH$_3$ | |
| 184 | H | 5-Cl | CH$_3$ | H | CH$_3$ | CF$_3$ | C$_2$H$_5$ | |
| 185 | H | 5-Cl | C$_2$H$_5$ | H | CH$_3$ | CF$_3$ | C$_2$H$_5$ | |
| 186 | H | 5-Cl | CH$_2$CH=CH$_2$ | H | CH$_3$ | CF$_3$ | C$_2$H$_5$ | |
| 187 | H | 5-Cl | CH$_2$C≡CH | H | CH$_3$ | CF$_3$ | C$_2$H$_5$ | |

TABLE 1-continued

3-Pyridines

| Compound No. | X | Y | $R^1$ | $R^2$ | $R^3$ | $R^4$ | $R^5$ | Melting Point (° C.) |
|---|---|---|---|---|---|---|---|---|
| 188 | H | 5-Cl | $CH_2CF_3$ | H | $CH_3$ | $CF_3$ | $C_2H_5$ | |
| 189 | H | 5-Cl | $CH_2OCH_3$ | H | $CH_3$ | $CF_3$ | $C_2H_5$ | |
| 190 | H | 5-Cl | $CH_2CN$ | H | $CH_3$ | $CF_3$ | $C_2H_5$ | |
| 191 | H | 5-Cl | $C_6H_5$ | H | $CH_3$ | $CF_3$ | $C_2H_5$ | |
| 192 | H | 5-Cl | $CH_3$ | H | | $CH_2CH_2$ | $CH_3$ | |
| 193 | H | 5-Cl | $C_2H_5$ | H | | $CH_2CH_2$ | $CH_3$ | |
| 194 | H | 5-Cl | $CH_2CH=CH_2$ | H | | $CH_2CH_2$ | $CH_3$ | |
| 195 | H | 5-Cl | $CH_2C\equiv CH$ | H | | $CH_2CH_2$ | $CH_3$ | |
| 196 | H | 5-Cl | $CH_2CF_3$ | H | | $CH_2CH_2$ | $CH_3$ | |
| 197 | H | 5-Cl | $CH_2OCH_3$ | H | | $CH_2CH_2$ | $CH_3$ | |
| 198 | H | 5-Cl | $CH_2CN$ | H | | $CH_2CH_2$ | $CH_3$ | |
| 199 | H | 5-Cl | $C_6H_5$ | H | | $CH_2CH_2$ | $CH_3$ | |
| 200 | H | 5-Cl | $CH_3$ | H | | $CH_2CH_2$ | $C_2H_5$ | |
| 201 | H | 5-Cl | $C_2H_5$ | H | | $CH_2CH_2$ | $C_2H_5$ | |
| 202 | H | 5-Cl | $CH_2CH=CH_2$ | H | | $CH_2CH_2$ | $C_2H_5$ | |
| 203 | H | 5-Cl | $CH_2C\equiv CH$ | H | | $CH_2CH_2$ | $C_2H_5$ | |
| 204 | H | 5-Cl | $CH_2CF_3$ | H | | $CH_2CH_2$ | $C_2H_5$ | |
| 205 | H | 5-Cl | $CH_2OCH_3$ | H | | $CH_2CH_2$ | $C_2H_5$ | |
| 206 | H | 5-Cl | $CH_2CN$ | H | | $CH_2CH_2$ | $C_2H_5$ | |
| 207 | H | 5-Cl | $C_6H_5$ | H | | $CH_2CH_2$ | $C_2H_5$ | |
| 208 | H | 5-Cl | $CH_3$ | H | | $CH_2CH_2$ | cyclopropyl | |
| 209 | H | 5-Cl | $C_2H_5$ | H | | $CH_2CH_2$ | cyclopropyl | |
| 210 | H | 5-Cl | $CH_2CH=CH_2$ | H | | $CH_2CH_2$ | cyclopropyl | |
| 211 | H | 5-Cl | $CH_2C\equiv CH$ | H | | $CH_2CH_2$ | cyclopropyl | |
| 212 | H | 5-Cl | $CH_2CF_3$ | H | | $CH_2CH_2$ | cyclopropyl | |
| 213 | H | 5-Cl | $CH_2OCH_3$ | H | | $CH_2CH_2$ | cyclopropyl | |
| 214 | H | 5-Cl | $CH_2CN$ | H | | $CH_2CH_2$ | cyclopropyl | |
| 215 | H | 5-Cl | $C_6H_5$ | H | | $CH_2CH_2$ | cyclopropyl | |
| 216 | H | 5-Cl | $CH_3$ | H | | $CH_2CH_2$ | $CH_2CF_3$ | |
| 217 | H | 5-Cl | $C_2H_5$ | H | | $CH_2CH_2$ | $CH_2CF_3$ | |
| 218 | H | 5-Cl | $CH_2CH=CH_2$ | H | | $CH_2CH_2$ | $CH_2CF_3$ | |
| 219 | H | 5-Cl | $CH_2C\equiv CH$ | H | | $CH_2CH_2$ | $CH_2CF_3$ | |
| 220 | H | 5-Cl | $CH_2CF_3$ | H | | $CH_2CH_2$ | $CH_2CF_3$ | |
| 221 | H | 5-Cl | $CH_2OCH_3$ | H | | $CH_2CH_2$ | $CH_2CF_3$ | |
| 222 | H | 5-Cl | $CH_2CN$ | H | | $CH_2CH_2$ | $CH_2CF_3$ | |
| 223 | H | 5-Cl | $C_6H_5$ | H | | $CH_2CH_2$ | $CH_2CF_3$ | |
| 224 | H | 5-Cl | $CH_3$ | H | | $CH_2CH_2$ | $CH_2OCH_3$ | |
| 225 | H | 5-Cl | $C_2H_5$ | H | | $CH_2CH_2$ | $CH_2OCH_3$ | |
| 226 | H | 5-Cl | $CH_2CH=CH_2$ | H | | $CH_2CH_2$ | $CH_2OCH_3$ | |
| 227 | H | 5-Cl | $CH_2C\equiv CH$ | H | | $CH_2CH_2$ | $CH_2OCH_3$ | |
| 228 | H | 5-Cl | $CH_2CF_3$ | H | | $CH_2CH_2$ | $CH_2OCH_3$ | |
| 229 | H | 5-Cl | $CH_2OCH_3$ | H | | $CH_2CH_2$ | $CH_2OCH_3$ | |
| 230 | H | 5-Cl | $CH_2CN$ | H | | $CH_2CH_2$ | $CH_2OCH_3$ | |
| 231 | H | 5-Cl | $C_6H_5$ | H | | $CH_2CH_2$ | $CH_2OCH_3$ | |
| 232 | H | 5-Br | $CH_3$ | H | $CH_3$ | $CH_3$ | $CH_3$ | |
| 233 | H | 5-Br | $CH_2CH=CH_2$ | H | $CH_3$ | $CH_3$ | $CH_3$ | |
| 234 | H | 5-Br | $CH_2C\equiv CH$ | H | $CH_3$ | $CH_3$ | $CH_3$ | |
| 235 | H | 5-Br | $CH_2CF_3$ | H | $CH_3$ | $CH_3$ | $CH_3$ | |
| 236 | H | 5-Br | $CH_2OCH_3$ | H | $CH_3$ | $CH_3$ | $CH_3$ | |
| 237 | H | 5-Br | $CH_2CN$ | H | $CH_3$ | $CH_3$ | $CH_3$ | |
| 238 | H | 5-Br | $C_6H_5$ | H | $CH_3$ | $CH_3$ | $CH_3$ | |
| 239 | H | 5-Br | $CH_3$ | H | $CH_3$ | $CH_3$ | $C_2H_5$ | |
| 240 | H | 5-Br | $CH_2CH=CH_2$ | H | $CH_3$ | $CH_3$ | $C_2H_5$ | |
| 241 | H | 5-Br | $CH_2C\equiv CH$ | H | $CH_3$ | $CH_3$ | $C_2H_5$ | |
| 242 | H | 5-Br | $CH_2CF_3$ | H | $CH_3$ | $CH_3$ | $C_2H_5$ | |
| 243 | H | 5-Br | $CH_2OCH_3$ | H | $CH_3$ | $CH_3$ | $C_2H_5$ | |
| 244 | H | 5-Br | $CH_2CN$ | H | $CH_3$ | $CH_3$ | $C_2H_5$ | |
| 245 | H | 5-Br | $C_6H_5$ | H | $CH_3$ | $CH_3$ | $C_2H_5$ | |
| 246 | 6-Cl | 5-Cl | $CH_3$ | H | $CH_3$ | $CH_3$ | $CH_3$ | |
| 247 | 6-Cl | 5-Cl | $C_2H_5$ | H | $CH_3$ | $CH_3$ | $CH_3$ | |
| 248 | 6-Cl | 5-Cl | $CH_2CH=CH_2$ | H | $CH_3$ | $CH_3$ | $CH_3$ | |
| 249 | 6-Cl | 5-Cl | $CH_2C\equiv CH$ | H | $CH_3$ | $CH_3$ | $CH_3$ | |
| 250 | 6-Cl | 5-Cl | $CH_2CF_3$ | H | $CH_3$ | $CH_3$ | $CH_3$ | |
| 251 | 6-Cl | 5-Cl | 6-Cl | H | $CH_3$ | $CH_3$ | $CH_3$ | |
| 252 | 6-Cl | 5-Cl | 6-Cl | H | $CH_3$ | $CH_3$ | $CH_3$ | |
| 253 | 6-Cl | 5-Cl | 6-Cl | H | $CH_3$ | $CH_3$ | $CH_3$ | |
| 254 | 6-Cl | 5-Cl | $CH_3$ | H | $CH_3$ | $CH_3$ | $C_2H_5$ | |
| 255 | 6-Cl | 5-Cl | $C_2H_5$ | H | $CH_3$ | $CH_3$ | $C_2H_5$ | |
| 256 | 6-Cl | 5-Cl | $CH_2CH=CH_2$ | H | $CH_3$ | $CH_3$ | $C_2H_5$ | |
| 257 | 6-Cl | 5-Cl | $CH_2C\equiv CH$ | H | $CH_3$ | $CH_3$ | $C_2H_5$ | |
| 258 | 6-Cl | 5-Cl | $CH_3$ | H | $CH_3$ | $CH_3$ | $CH_2OCH_3$ | |
| 259 | 6-Cl | 5-Cl | $C_2H_5$ | H | $CH_3$ | $CH_3$ | $CH_2OCH_3$ | |
| 260 | 6-Cl | 5-Cl | $CH_2OCH_3$ | H | $CH_3$ | $CH_3$ | $CH_2OCH_3$ | |
| 261 | 6-Cl | 5-Cl | $C_6H_5$ | H | $CH_3$ | $CH_3$ | $C_2H_5$ | |

TABLE 1-continued

3-Pyridines

| Compound No. | X | Y | $R^1$ | $R^2$ | $R^3$ | $R^4$ | $R^5$ | Melting Point (° C.) |
|---|---|---|---|---|---|---|---|---|
| 262 | 4-SCH$_3$ | 5-OC$_6$H$_5$ | CH$_3$ | H | CH$_3$ | CH$_3$ | CH$_3$ | |
| 263 | 4-SCH$_3$ | 5-OC$_6$H$_5$ | C$_2$H$_5$ | H | CH$_3$ | CH$_3$ | CH$_3$ | |
| 264 | 4-SCH$_3$ | 5-OC$_6$H$_5$ | CH$_2$CH=CH$_2$ | H | CH$_3$ | CH$_3$ | CH$_3$ | |
| 265 | 4-SCH$_3$ | 5-OC$_6$H$_5$ | CH$_2$C≡CH | H | CH$_3$ | CH$_3$ | CH$_3$ | |
| 266 | 4-SCH$_3$ | 5-OC$_6$H$_5$ | CH$_2$CF$_3$ | H | CH$_3$ | CH$_3$ | CH$_3$ | |
| 267 | 4-SCH$_3$ | 5-OC$_6$H$_5$ | CH$_2$OCH$_3$ | H | CH$_3$ | CH$_3$ | CH$_3$ | |
| 268 | 4-SCH$_3$ | 5-OC$_6$H$_5$ | CH$_2$CN | H | CH$_3$ | CH$_3$ | CH$_3$ | |
| 269 | 4-SCH$_3$ | 5-OC$_6$H$_5$ | C$_6$H$_5$ | H | CH$_3$ | CH$_3$ | CH$_3$ | |
| 270 | 4-SCH$_3$ | 5-OC$_6$H$_5$ | CH$_3$ | H | CH$_3$ | CH$_3$ | C$_2$H$_5$ | |
| 271 | 4-SCH$_3$ | 5-OC$_6$H$_5$ | C$_2$H$_5$ | H | CH$_3$ | CH$_3$ | C$_2$H$_5$ | |
| 272 | 4-SCH$_3$ | 5-OC$_6$H$_5$ | CH$_2$CH=CH$_2$ | H | CH$_3$ | CH$_3$ | C$_2$H$_5$ | |
| 273 | 4-SCH$_3$ | 5-OC$_6$H$_5$ | CH$_2$C≡CH | H | CH$_3$ | CH$_3$ | C$_2$H$_5$ | |
| 274 | 4-SCH$_3$ | 5-OC$_6$H$_5$ | CH$_2$CF$_3$ | H | CH$_3$ | CH$_3$ | C$_2$H$_5$ | |
| 275 | 4-SCH$_3$ | 5-OC$_6$H$_5$ | CH$_2$OCH$_3$ | H | CH$_3$ | CH$_3$ | C$_2$H$_5$ | |
| 276 | 4-SCH$_3$ | 5-OC$_6$H$_5$ | CH$_2$CN | H | CH$_3$ | CH$_3$ | C$_2$H$_5$ | |
| 277 | 4-SCH$_3$ | 5-OC$_6$H$_5$ | C$_6$H$_5$ | H | CH$_3$ | CH$_3$ | C$_2$H$_5$ | |
| 278 | H | 5-CON(i-C$_3$H$_7$)$_2$ | CH$_3$ | H | CH$_3$ | CH$_3$ | CH$_3$ | |
| 279 | H | 5-CON(i-C$_3$H$_7$)$_2$ | C$_2$H$_5$ | H | CH$_3$ | CH$_3$ | CH$_3$ | |
| 280 | H | 5-CON(i-C$_3$H$_7$)$_2$ | CH$_2$CH=CH$_2$ | H | CH$_3$ | CH$_3$ | CH$_3$ | |
| 281 | H | 5-CON(i-C$_3$H$_7$)$_2$ | CH$_2$C≡CH | H | CH$_3$ | CH$_3$ | CH$_3$ | |
| 282 | H | 5-CON(i-C$_3$H$_7$)$_2$ | CH$_2$CF$_3$ | H | CH$_3$ | CH$_3$ | CH$_3$ | |
| 283 | H | 5-CON(i-C$_3$H$_7$)$_2$ | CH$_2$OCH$_3$ | H | CH$_3$ | CH$_3$ | CH$_3$ | |
| 284 | H | 5-CON(i-C$_3$H$_7$)$_2$ | CH$_2$CN | H | CH$_3$ | CH$_3$ | CH$_3$ | |
| 285 | H | 5-CON(i-C$_3$H$_7$)$_2$ | C$_6$H$_5$ | H | CH$_3$ | CH$_3$ | CH$_3$ | |
| 286 | H | 5-CON(i-C$_3$H$_7$)$_2$ | CH$_3$ | H | CH$_3$ | CH$_3$ | C$_2$H$_5$ | |
| 287 | H | 5-CON(i-C$_3$H$_7$)$_2$ | CH$_2$CH=CH$_2$ | H | CH$_3$ | CH$_3$ | C$_2$H$_5$ | |
| 288 | H | 5-CON(i-C$_3$H$_7$)$_2$ | CH$_2$C≡CH | H | CH$_3$ | CH$_3$ | C$_2$H$_5$ | |
| 289 | H | 5-CON(i-C$_3$H$_7$)$_2$ | CH$_2$CF$_3$ | H | CH$_3$ | CH$_3$ | C$_2$H$_5$ | |
| 290 | H | 5-CON(i-C$_3$H$_7$)$_2$ | CH$_2$OCH$_3$ | H | CH$_3$ | CH$_3$ | C$_2$H$_5$ | |
| 291 | H | 5-CON(i-C$_3$H$_7$)$_2$ | CH$_2$CN | H | CH$_3$ | CH$_3$ | C$_2$H$_5$ | |
| 292 | H | 5-CON(i-C$_3$H$_7$)$_2$ | C$_6$H$_5$ | H | CH$_3$ | CH$_3$ | C$_2$H$_5$ | |
| 293 | H | 5-CO$_2$CH$_2$C$_6$H$_5$ | CH$_3$ | H | CH$_3$ | CH$_3$ | CH$_3$ | |
| 294 | H | 5-CO$_2$CH$_2$C$_6$H$_5$ | C$_2$H$_5$ | H | CH$_3$ | CH$_3$ | CH$_3$ | |
| 295 | H | 5-CO$_2$CH$_2$C$_6$H$_5$ | CH$_2$CH=CH$_2$ | H | CH$_3$ | CH$_3$ | CH$_3$ | |
| 296 | H | 5-CO$_2$CH$_2$C$_6$H$_5$ | CH$_2$C≡CH | H | CH$_3$ | CH$_3$ | CH$_3$ | |
| 297 | H | 5-CO$_2$CH$_2$C$_6$H$_5$ | CH$_2$CF$_3$ | H | CH$_3$ | CH$_3$ | CH$_3$ | |
| 298 | H | 5-CO$_2$CH$_2$C$_6$H$_5$ | CH$_2$OCH$_3$ | H | CH$_3$ | CH$_3$ | CH$_3$ | |
| 299 | H | 5-CO$_2$CH$_2$C$_6$H$_5$ | CH$_2$CN | H | CH$_3$ | CH$_3$ | CH$_3$ | |
| 300 | H | 5-CO$_2$CH$_2$C$_6$H$_5$ | C$_6$H$_5$ | H | CH$_3$ | CH$_3$ | CH$_3$ | |
| 301 | H | 5-CO$_2$CH$_2$C$_6$H$_5$ | CH$_3$ | H | CH$_3$ | CH$_3$ | C$_2$H$_5$ | |
| 302 | H | 5-CO$_2$CH$_2$C$_6$H$_5$ | C$_2$H$_5$ | H | CH$_3$ | CH$_3$ | C$_2$H$_5$ | |
| 303 | H | 5-CO$_2$CH$_2$C$_6$H$_5$ | CH$_2$CH=CH$_2$ | H | CH$_3$ | CH$_3$ | C$_2$H$_5$ | |
| 304 | H | 5-CO$_2$CH$_2$C$_6$H$_5$ | CH$_2$C≡CH | H | CH$_3$ | CH$_3$ | C$_2$H$_5$ | |
| 305 | H | 5-CO$_2$CH$_2$C$_6$H$_5$ | CH$_2$CF$_3$ | H | CH$_3$ | CH$_3$ | C$_2$H$_5$ | |
| 306 | H | 5-CO$_2$CH$_2$C$_6$H$_5$ | CH$_2$OCH$_3$ | H | CH$_3$ | CH$_3$ | C$_2$H$_5$ | |
| 307 | H | 5-CO$_2$CH$_2$C$_6$H$_5$ | CH$_2$CN | H | CH$_3$ | CH$_3$ | C$_2$H$_5$ | |
| 308 | H | 5-CO$_2$CH$_2$C$_6$H$_5$ | C$_6$H$_5$ | H | CH$_3$ | CH$_3$ | C$_2$H$_5$ | |
| 309 | H | 5-CON(i-C$_3$H$_7$)$_2$ | CH$_3$ | H | CH$_3$ | C$_2$H$_5$ | CH$_3$ | |
| 310 | H | 5-CON(i-C$_3$H$_7$)$_2$ | C$_2$H$_5$ | H | CH$_3$ | C$_2$H$_5$ | CH$_3$ | |
| 311 | H | 5-CON(i-C$_3$H$_7$)$_2$ | CH$_2$CH=CH$_2$ | H | CH$_3$ | C$_2$H$_5$ | CH$_3$ | |
| 312 | H | 5-CON(i-C$_3$H$_7$)$_2$ | CH$_2$C≡CH | H | CH$_3$ | C$_2$H$_5$ | CH$_3$ | |
| 313 | H | 5-CON(i-C$_3$H$_7$)$_2$ | CH$_2$CF$_3$ | H | CH$_3$ | C$_2$H$_5$ | CH$_3$ | |
| 314 | H | 5-CON(i-C$_3$H$_7$)$_2$ | CH$_2$OCH$_3$ | H | CH$_3$ | C$_2$H$_5$ | CH$_3$ | |
| 315 | H | 5-CON(i-C$_3$H$_7$)$_2$ | CH$_2$CN | H | CH$_3$ | C$_2$H$_5$ | CH$_3$ | |
| 316 | H | 5-CON(i-C$_3$H$_7$)$_2$ | C$_6$H$_5$ | H | CH$_3$ | C$_2$H$_5$ | CH$_3$ | |
| 317 | H | 5-CON(i-C$_3$H$_7$)$_2$ | CH$_3$ | H | CH$_3$ | C$_2$H$_5$ | C$_2$H$_5$ | |
| 318 | H | 5-CON(i-C$_3$H$_7$)$_2$ | C$_2$H$_5$ | H | CH$_3$ | C$_2$H$_5$ | C$_2$H$_5$ | |
| 319 | H | 5-CON(i-C$_3$H$_7$)$_2$ | CH$_2$CH=CH$_2$ | H | CH$_3$ | C$_2$H$_5$ | C$_2$H$_5$ | |
| 320 | H | 5-CON(i-C$_3$H$_7$)$_2$ | CH$_2$C≡CH | H | CH$_3$ | C$_2$H$_5$ | C$_2$H$_5$ | |
| 321 | H | 5-CON(i-C$_3$H$_7$)$_2$ | CH$_2$CF$_3$ | H | CH$_3$ | C$_2$H$_5$ | C$_2$H$_5$ | |
| 322 | H | 5-CON(i-C$_3$H$_7$)$_2$ | CH$_2$OCH$_3$ | H | CH$_3$ | C$_2$H$_5$ | C$_2$H$_5$ | |
| 323 | H | 5-CON(i-C$_3$H$_7$)$_2$ | CH$_2$CN | H | CH$_3$ | C$_2$H$_5$ | C$_2$H$_5$ | |
| 324 | H | 5-CON(i-C$_3$H$_7$)$_2$ | C$_6$H$_5$ | H | CH$_3$ | C$_2$H$_5$ | C$_2$H$_5$ | |
| 325 | H | 5-COCH$_3$ | CH$_3$ | H | CH$_3$ | CH$_3$ | CH$_3$ | |
| 326 | H | 5-COCH$_3$ | C$_2$H$_5$ | H | CH$_3$ | CH$_3$ | CH$_3$ | |
| 327 | H | 5-COCH$_3$ | CH2CH=CH$_2$ | H | CH$_3$ | CH$_3$ | CH$_3$ | |
| 328 | H | 5-COCH$_3$ | CH$_2$C≡CH | H | CH$_3$ | CH$_3$ | CH$_3$ | |
| 329 | H | 5-COCH$_3$ | CH$_2$CF$_3$ | H | CH$_3$ | CH$_3$ | CH$_3$ | |
| 330 | H | 5-COCH$_3$ | CH$_2$OCH$_3$ | H | CH$_3$ | CH$_3$ | CH$_3$ | |
| 331 | H | 5-COCH$_3$ | CH$_2$CN | H | CH$_3$ | CH$_3$ | CH$_3$ | |
| 332 | H | 5-COCH$_3$ | C$_6$H$_5$ | H | CH$_3$ | CH$_3$ | CH$_3$ | |
| 333 | H | 5-COCH$_3$ | CH$_3$ | H | CH$_3$ | CH$_3$ | C$_2$H$_5$ | |
| 334 | H | 5-COCH$_3$ | C$_2$H$_5$ | H | CH$_3$ | CH$_3$ | C$_2$H$_5$ | |
| 335 | H | 5-COCH$_3$ | CH$_2$CH=CH$_2$ | H | CH$_3$ | CH$_3$ | C$_2$H$_5$ | |

TABLE 1-continued

3-Pyridines

| Compound No. | X | Y | $R^1$ | $R^2$ | $R^3$ | $R^4$ | $R^5$ | Melting Point (° C.) |
|---|---|---|---|---|---|---|---|---|
| 336 | H | 5-COCH$_3$ | CH=CH$_2$ | H | CH$_3$ | CH$_3$ | C$_2$H$_5$ | |
| 337 | H | 5-COCH$_3$ | CH$_2$CF$_3$ | H | CH$_3$ | CH$_3$ | C$_2$H$_5$ | |
| 338 | H | 5-COCH$_3$ | CH$_2$OCH$_3$ | H | CH$_3$ | CH$_3$ | C$_2$H$_5$ | |
| 339 | H | 5-COCH$_3$ | CH$_2$CN | H | CH$_3$ | CH$_3$ | C$_2$H$_5$ | |
| 340 | H | 5-COCH$_3$ | C$_6$H$_5$ | H | CH$_3$ | CH$_3$ | C$_2$H$_5$ | |
| 341 | H | 5-CN | CH$_3$ | H | CH$_3$ | CH$_3$ | CH$_3$ | |
| 342 | H | 5-CN | C$_2$H$_5$ | H | CH$_3$ | CH$_3$ | CH$_3$ | |
| 343 | H | 5-CN | CH$_2$CH=CH$_2$ | H | CH$_3$ | CH$_3$ | CH$_3$ | |
| 344 | H | 5-CN | CH$_2$C≡CH | H | CH$_3$ | CH$_3$ | CH$_3$ | |
| 345 | H | 5-CN | CH$_2$CF$_3$ | H | CH$_3$ | CH$_3$ | CH$_3$ | |
| 346 | H | 5-CN | CH$_2$OCH$_3$ | H | CH$_3$ | CH$_3$ | CH$_3$ | |
| 347 | H | 5-CN | CH$_2$CN | H | CH$_3$ | CH$_3$ | CH$_3$ | |
| 348 | H | 5-CN | C$_6$H$_5$ | H | CH$_3$ | CH$_3$ | CH$_3$ | |
| 349 | H | 5-CN | CH$_3$ | H | CH$_3$ | CH$_3$ | C$_2$H$_5$ | |
| 350 | H | 5-CN | C$_2$H$_5$ | H | CH$_3$ | CH$_3$ | C$_2$H$_5$ | |
| 351 | H | 5-CN | CH$_2$CH=CH$_2$ | H | CH$_3$ | CH$_3$ | C$_2$H$_5$ | |
| 352 | H | 5-CN | CH$_2$C≡CH | H | CH$_3$ | CH$_3$ | C$_2$H$_5$ | |
| 353 | H | 5-CN | CH$_2$CF$_3$ | H | CH$_3$ | CH$_3$ | C$_2$H$_5$ | |
| 354 | H | 5-CN | CH$_2$OCH$_3$ | H | CH$_3$ | CH$_3$ | C$_2$H$_5$ | |
| 355 | H | 5-CN | CH$_2$CN | H | CH$_3$ | CH$_3$ | C$_2$H$_5$ | |
| 356 | H | 5-CN | C$_6$H$_5$ | H | CH$_3$ | CH$_3$ | C$_2$H$_5$ | |
| 357 | H | 5-C≡CH | CH$_3$ | H | CH$_3$ | CH$_3$ | CH$_3$ | |
| 358 | H | 5-C≡CH | C$_2$H$_5$ | H | CH$_3$ | CH$_3$ | CH$_3$ | |
| 359 | H | 5-C≡CH | CH$_2$CH=CH$_2$ | H | CH$_3$ | CH$_3$ | CH$_3$ | |
| 360 | H | 5-C≡CH | CH$_2$C≡CH | H | CH$_3$ | CH$_3$ | CH$_3$ | |
| 361 | H | 5-C≡CH | CH$_2$CF$_3$ | H | CH$_3$ | CH$_3$ | CH$_3$ | |
| 362 | H | 5-C≡CH | CH$_2$OCH$_3$ | H | CH$_3$ | CH$_3$ | CH$_3$ | |
| 363 | H | 5-C≡CH | CH$_2$CN | H | CH$_3$ | CH$_3$ | CH$_3$ | |
| 364 | H | 5-C≡CH | C$_6$H$_5$ | H | CH$_3$ | CH$_3$ | CH$_3$ | |
| 365 | H | 5-C≡CH | CH$_3$ | H | CH$_3$ | CH$_3$ | C$_2$H$_5$ | |
| 366 | H | 5-C≡CH | C$_2$H$_5$ | H | CH$_3$ | CH$_3$ | C$_2$H$_5$ | |
| 367 | H | 5-C≡CH | CH$_2$CH=CH$_2$ | H | CH$_3$ | CH$_3$ | C$_2$H$_5$ | |
| 368 | H | 5-C≡CH | CH$_2$C≡CH | H | CH$_3$ | CH$_3$ | C$_2$H$_5$ | |
| 369 | H | 5-C≡CH | CH$_2$CF$_3$ | H | CH$_3$ | CH$_3$ | C$_2$H$_5$ | |
| 370 | H | 5-C≡CH | CH$_2$OCH$_3$ | H | CH$_3$ | CH$_3$ | C$_2$H$_5$ | |
| 371 | H | 5-C≡CH | CH$_2$CN | H | CH$_3$ | CH$_3$ | C$_2$H$_5$ | |
| 372 | H | 5-C≡CH | C$_6$H$_5$ | H | CH$_3$ | CH$_3$ | C$_2$H$_5$ | |
| 373 | H | 5-CH=CH$_2$ | CH$_3$ | H | CH$_3$ | CH$_3$ | CH$_3$ | |
| 374 | H | 5-CH=CH$_2$ | C$_2$H$_5$ | H | CH$_3$ | CH$_3$ | CH$_3$ | |
| 375 | H | 5-CH=CH$_2$ | n-C$_3$H$_7$ | H | CH$_3$ | CH$_3$ | CH$_3$ | |
| 376 | H | 5-CH=CH$_2$ | CH$_2$OCH$_3$ | H | CH$_3$ | CH$_3$ | CH$_3$ | |
| 377 | H | 5-C(OC$_2$H$_5$)=CH$_2$ | CH$_3$ | H | CH$_3$ | CH$_3$ | CH$_3$ | |
| 378 | H | 5-C(OC$_2$H$_5$)=CH$_2$ | C$_2$H$_5$ | H | CH$_3$ | CH$_3$ | CH$_3$ | |
| 379 | H | 5-C(OC$_2$H$_5$)=CH$_2$ | n-C$_3$H$_7$ | H | CH$_3$ | CH$_3$ | CH$_3$ | |
| 380 | H | 5-C(OC$_2$H$_5$)=CH$_2$ | CH$_2$OCH$_3$ | H | CH$_3$ | CH$_3$ | CH$_3$ | |
| 381 | H | 5-Cl | CH$_3$ | H | CH$_3$ | CH$_3$ | CH$_2$OC$_2$H$_5$ | |
| 382 | H | 5-Cl | C$_2$H$_5$ | H | CH$_3$ | CH$_3$ | CH$_2$OC$_2$H$_5$ | |
| 383 | H | 5-Cl | CH$_3$ | H | CH$_3$ | CH$_3$ | CH(OCH$_3$)CH$_3$ | |
| 384 | H | 5-Cl | C$_2$H$_5$ | H | CH$_3$ | CH$_3$ | CH(OCH$_3$)CH$_3$ | |
| 385 | H | 5-Cl | CH$_2$CH$_2$F | H | CH$_3$ | CH$_3$ | CH$_3$ | |
| 386 | H | 5-Br | CH$_2$CH$_2$F | H | CH$_3$ | CH$_3$ | CH$_2$OH | |
| 387 | 6-CH$_3$ | 5-Cl | CH$_2$CH$_2$F | H | CH$_3$ | CH$_3$ | CH$_2$OCH$_3$ | |
| 388 | 6-Cl | 5-Cl | CH$_2$CH$_2$F | H | CH$_3$ | CH$_3$ | CH$_3$ | |
| 389 | 4-SCH$_3$ | 5-OC$_6$H$_5$ | CH$_2$CH$_2$F | H | CH$_3$ | CH$_3$ | CH$_2$OH | |
| 390 | H | 5-COCH$_3$ | CH$_2$CH$_2$F | H | CH$_3$ | CH$_3$ | CH$_2$OCH$_3$ | |
| 391 | H | 5-CN | CH$_2$CH$_2$F | H | CH$_3$ | CH$_3$ | CH$_3$ | |
| 392 | H | 5-C≡CH | CH$_2$CH$_2$F | H | CH$_3$ | CH$_3$ | CH$_2$OH | |
| 393 | H | 5-CH=CH$_2$ | CH$_2$CH$_2$F | H | CH$_3$ | C$_2$H$_5$ | CH$_2$OCH$_3$ | |
| 394 | H | 5-C(OC$_2$H$_5$)=CH$_2$ | CH$_2$CH$_2$F | H | CH$_3$ | C$_2$H$_5$ | CH$_3$ | |
| 395 | 6-CH$_3$ | H | CH$_2$CH$_2$F | H | CH$_3$ | C$_2$H$_5$ | CH$_2$OH | |
| 396 | H | 5-CON(i-C$_3$H$_7$)$_2$ | CH$_2$CH$_2$F | H | CH$_3$ | C$_2$H$_5$ | CH$_2$OCH$_3$ | |
| 397 | H | 5-CO$_2$CH$_3$ | CH$_2$CH$_2$F | H | CH$_3$ | C$_2$H$_5$ | CH$_2$OH | |
| 398 | H | 5-CO$_2$H | CH$_2$CH$_2$F | H | CH$_3$ | C$_2$H$_5$ | CH$_3$ | |
| 399 | H | 5-I | CH$_2$CH$_2$F | H | CH$_3$ | C$_2$H$_5$ | CH$_2$OCH$_3$ | |
| 400 | H | 5-Cl | CH$_2$CHF$_2$ | H | CH$_3$ | CH$_3$ | CH$_3$ | |
| 401 | H | 5-Br | CH$_2$CHF$_2$ | H | CH$_3$ | CH$_3$ | CH$_2$OH | |
| 402 | 6-CH$_3$ | 5-Cl | CH$_2$CHF$_2$ | H | CH$_3$ | CH$_3$ | CH$_2$OCH$_3$ | |
| 403 | 6-Cl | 5-Cl | CH$_2$CHF$_2$ | H | CH$_3$ | CH$_3$ | CH$_3$ | |
| 404 | 4-SCH$_3$ | 5-OC$_6$H$_5$ | CH$_2$CHF$_2$ | H | CH$_3$ | CH$_3$ | CH$_2$OH | |
| 405 | H | 5-COCH$_3$ | CH$_2$CHF$_2$ | H | CH$_3$ | CH$_3$ | CH$_2$OCH$_3$ | |
| 406 | H | 5-CN | CH$_2$CHF$_2$ | H | CH$_3$ | CH$_3$ | CH$_3$ | |
| 407 | H | 5-C≡CH | CH$_2$CHF$_2$ | H | CH$_3$ | CH$_3$ | CH$_2$OH | |
| 408 | H | 5-CH=CH$_2$ | CH$_2$CHF$_2$ | H | CH$_3$ | C$_2$H$_5$ | CH$_2$OCH$_3$ | |
| 409 | H | 5-C(OC$_2$H$_5$)=CH$_2$ | CH$_2$CHF$_2$ | H | CH$_3$ | C$_2$H$_5$ | CH$_3$ | |

TABLE 1-continued

3-Pyridines

| Compound No. | X | Y | $R^1$ | $R^2$ | $R^3$ | $R^4$ | $R^5$ | Melting Point (° C.) |
|---|---|---|---|---|---|---|---|---|
| 410 | 6-$CH_3$ | H | $CH_2CHF_2$ | H | $CH_3$ | $C_2H_5$ | $CH_2OH$ | |
| 411 | H | 5-$CON(i-C_3H_7)_2$ | $CH_2CHF_2$ | H | $CH_3$ | $C_2H_5$ | $CH_2OCH_3$ | |
| 412 | H | 5-$CO_2CH_3$ | $CH_2CHF_2$ | H | $CH_3$ | $C_2H_5$ | $CH_2OH$ | |
| 413 | H | 5-$CO_2H$ | $CH_2CHF_2$ | H | $CH_3$ | $C_2H_5$ | $CH_3$ | |
| 414 | H | 5-I | $CH_2CHF_2$ | H | $CH_3$ | $C_2H_5$ | $CH_2OCH_3$ | |
| 415 | H | 5-Cl | $CH_2CH_2Cl$ | H | $CH_3$ | $CH_3$ | $CH_3$ | |
| 416 | H | 5-Br | $CH_2CH_2Cl$ | H | $CH_3$ | $CH_3$ | $CH_2OH$ | |
| 417 | 6-$CH_3$ | 5-Cl | $CH_2CH_2Cl$ | H | $CH_3$ | $CH_3$ | $CH_2OCH_3$ | |
| 418 | 6-Cl | 5-Cl | $CH_2CH_2Cl$ | H | $CH_3$ | $CH_3$ | $CH_3$ | |
| 419 | 4-$SCH_3$ | 5-$OCH_6H_5$ | $CH_2CH_2Cl$ | H | $CH_3$ | $CH_3$ | $CH_2OH$ | |
| 420 | H | 5-$COCH_3$ | $CH_2CH_2Cl$ | H | $CH_3$ | $CH_3$ | $CH_2OCH_3$ | |
| 421 | H | 5-CN | $CH_2CH_2Cl$ | H | $CH_3$ | $CH_3$ | $CH_3$ | |
| 422 | H | 5-C≡CH | $CH_2CH_2Cl$ | H | $CH_3$ | $CH_3$ | $CH_2OH$ | |
| 423 | H | 5-CH=$CH_2$ | $CH_2CH_2Cl$ | H | $CH_3$ | $C_2H_5$ | $CH_2OCH_3$ | |
| 424 | H | 5-C($OC_2H_5$)=$CH_2$ | $CH_2CH_2Cl$ | H | $CH_3$ | $C_2H_5$ | $CH_3$ | |
| 425 | 6-$CH_3$ | H | $CH_2CH_2Cl$ | H | $CH_3$ | $C_2H_5$ | $CH_2OH$ | |
| 426 | H | 5-$CON(i-C_3H_7)_2$ | $CH_2CH_2Cl$ | H | $CH_3$ | $C_2H_5$ | $CH_2OCH_3$ | |
| 427 | H | 5-$CO_2CH_3$ | $CH_2CH_2Cl$ | H | $CH_3$ | $C_2H_5$ | $CH_2OH$ | |
| 428 | H | 5-$CO_2H$ | $CH_2CH_2Cl$ | H | $CH_3$ | $C_2H_5$ | $CH_3$ | |
| 429 | H | 5-I | $CH_2CH_2Cl$ | H | $CH_3$ | $C_2H_5$ | $CH_2OCH_3$ | |
| 430 | H | 5-Cl | CH=$CH_2$ | H | $CH_3$ | $CH_3$ | $CH_3$ | |
| 431 | H | 5-Br | CH=$CH_2$ | H | $CH_3$ | $CH_3$ | $CH_2OH$ | |
| 432 | 6-$CH_3$ | 5-Cl | CH=$CH_2$ | H | $CH_3$ | $CH_3$ | $CH_2OCH_3$ | |
| 433 | 6-Cl | 5-Cl | CH=$CH_2$ | H | $CH_3$ | $CH_3$ | $CH_3$ | |
| 434 | 4-$SCH_3$ | 5-$OCH_6H_5$ | CH=$CH_2$ | H | $CH_3$ | $CH_3$ | $CH_2OH$ | |
| 435 | H | 5-$COCH_3$ | CH=$CH_2$ | H | $CH_3$ | $CH_3$ | $CH_2OCH_3$ | |
| 436 | H | 5-CN | CH=$CH_2$ | H | $CH_3$ | $CH_3$ | $CH_3$ | |
| 437 | H | 5-C≡CH | CH=$CH_2$ | H | $CH_3$ | $CH_3$ | $CH_2OH$ | |
| 438 | H | 5-CH=$CH_2$ | CH=$CH_2$ | H | $CH_3$ | $C_2H_5$ | $CH_2OCH_3$ | |
| 439 | H | 5-C($OC_2H_5$)=$CH_2$ | CH=$CH_2$ | H | $CH_3$ | $C_2H_5$ | $CH_3$ | |
| 440 | 6-$CH_3$ | H | CH=$CH_2$ | H | $CH_3$ | $C_2H_5$ | $CH_2OH$ | |
| 441 | H | 5-$CON(i-C_3H_7)_2$ | CH=$CH_2$ | H | $CH_3$ | $C_2H_5$ | $CH_2OCH_3$ | |
| 442 | H | 5-$CO_2CH_3$ | CH=$CH_2$ | H | $CH_3$ | $C_2H_5$ | $CH_2OH$ | |
| 443 | H | 5-$CO_2H$ | CH=$CH_2$ | H | $CH_3$ | $C_2H_5$ | $CH_3$ | |
| 444 | H | 5-I | CH=$CH_2$ | H | $CH_3$ | $C_2H_5$ | $CH_2OCH_3$ | |
| 445 | H | 5-Cl | C≡CH | H | $CH_3$ | $CH_3$ | $CH_3$ | |
| 446 | H | 5-Br | C≡CH | H | $CH_3$ | $CH_3$ | $CH_2OH$ | |
| 447 | 6-$CH_3$ | 5-Cl | C≡CH | H | $CH_3$ | $CH_3$ | $CH_2OCH_3$ | |
| 448 | 6-Cl | 5-Cl | C≡CH | H | $CH_3$ | $CH_3$ | $CH_3$ | |
| 449 | 4-$SCH_3$ | 5-$OCH_6H_5$ | C≡CH | H | $CH_3$ | $CH_3$ | $CH_2OH$ | |
| 450 | H | 5-$COCH_3$ | C≡CH | H | $CH_3$ | $CH_3$ | $CH_2OCH_3$ | |
| 451 | H | 5-CN | C≡CH | H | $CH_3$ | $CH_3$ | $CH_3$ | |
| 452 | H | 5-C≡CH | C≡CH | H | $CH_3$ | $CH_3$ | $CH_2OH$ | |
| 453 | H | 5-CH=$CH_2$ | C≡CH | H | $CH_3$ | $C_2H_5$ | $CH_2OCH_3$ | |
| 454 | H | 5-C($OC_2H_5$)=$CH_2$ | C≡CH | H | $CH_3$ | $C_2H_5$ | $CH_3$ | |
| 455 | 6-$CH_3$ | H | C≡CH | H | $CH_3$ | $C_2H_5$ | $CH_2OH$ | |
| 456 | H | 5-$CON(i-C_3H_7)_2$ | C≡CH | H | $CH_3$ | $C_2H_5$ | $CH_2OCH_3$ | |
| 457 | H | 5-$CO_2CH_3$ | C≡CH | H | $CH_3$ | $C_2H_5$ | $CH_2OH$ | |
| 458 | H | 5-$CO_2H$ | C≡CH | H | $CH_3$ | $C_2H_5$ | $CH_3$ | |
| 459 | H | 5-I | C≡CH | H | $CH_3$ | $C_2H_5$ | $CH_2OCH_3$ | |
| 460 | H | 5-Cl | CH=$CHCH_3$ | H | $CH_3$ | $CH_3$ | $CH_3$ | |
| 461 | H | 5-Br | CH=$CHCH_3$ | H | $CH_3$ | $CH_3$ | $CH_2OH$ | |
| 462 | 6-$CH_3$ | 5-Cl | CH=$CHCH_3$ | H | $CH_3$ | $CH_3$ | $CH_2OCH_3$ | |
| 463 | 6-Cl | 5-Cl | CH=$CHCH_3$ | H | $CH_3$ | $CH_3$ | $CH_3$ | |
| 464 | 4-$SCH_3$ | 5-$OCH_6H_5$ | CH=$CHCH_3$ | H | $CH_3$ | $CH_3$ | $CH_2OH$ | |
| 465 | H | 5-$COCH_3$ | CH=$CHCH_3$ | H | $CH_3$ | $CH_3$ | $CH_2OCH_3$ | |
| 466 | H | 5-CN | CH=$CHCH_3$ | H | $CH_3$ | $CH_3$ | $CH_3$ | |
| 467 | H | 5-C≡CH | CH=$CHCH_3$ | H | $CH_3$ | $CH_3$ | $CH_2OH$ | |
| 468 | H | 5-CH=$CH_2$ | CH=$CHCH_3$ | H | $CH_3$ | $C_2H_5$ | $CH_2OCH_3$ | |
| 469 | H | 5-C($OC_2H_5$)=$CH_2$ | CH=$CHCH_3$ | H | $CH_3$ | $C_2H_5$ | $CH_3$ | |
| 470 | 6-$CH_3$ | H | CH=$CHCH_3$ | H | $CH_3$ | $C_2H_5$ | $CH_2OH$ | |
| 471 | H | 5-$CON(J-C_3H_7)_2$ | CH=$CHCH_3$ | H | $CH_3$ | $C_2H_5$ | $CH_2OCH_3$ | |
| 472 | H | 5-$CO_2CH_3$ | CH=$CHCH_3$ | H | $CH_3$ | $C_2H_5$ | $CH_2OH$ | |
| 473 | H | 5-$CO_2H$ | CH=$CHCH_3$ | H | $CH_3$ | $C_2H_5$ | $CH_3$ | |
| 474 | H | 5-I | CH=$CHCH_3$ | H | $CH_3$ | $C_2H_5$ | $CH_2OCH_3$ | |
| 475 | H | 5-Cl | C≡$CCH_3$ | H | $CH_3$ | $CH_3$ | $CH_3$ | |
| 476 | H | 5-Br | C≡$CCH_3$ | H | $CH_3$ | $CH_3$ | $CH_2OH$ | |
| 477 | 6-$CH_3$ | 5-Cl | C≡$CCH_3$ | H | $CH_3$ | $CH_3$ | $CH_2OCH_3$ | |
| 478 | 6-Cl | 5-Cl | C≡$CCH_3$ | H | $CH_3$ | $CH_3$ | $CH_3$ | |
| 479 | 4-$SCH_3$ | 5-$OCH_6H_5$ | C≡$CCH_3$ | H | $CH_3$ | $CH_3$ | $CH_2OH$ | |
| 480 | H | 5-$COCH_3$ | C≡$CCH_3$ | H | $CH_3$ | $CH_3$ | $CH_2OCH_3$ | |
| 481 | H | 5-CN | C≡$CCH_3$ | H | $CH_3$ | $CH_3$ | $CH_3$ | |
| 482 | H | 5-C≡CH | C≡$CCH_3$ | H | $CH_3$ | $CH_3$ | $CH_2OH$ | |
| 483 | H | 5-CH=$CH_2$ | C≡$CCH_3$ | H | $CH_3$ | $C_2H_5$ | $CH_2OCH_3$ | |

TABLE 1-continued

3-Pyridines

| Compound No. | X | Y | $R^1$ | $R^2$ | $R^3$ | $R^4$ | $R^5$ | Melting Point (° C.) |
|---|---|---|---|---|---|---|---|---|
| 484 | H | 5-C(OC$_2$H$_5$)=CH$_2$ | C≡CCH$_3$ | H | CH$_3$ | C$_2$H$_5$ | CH$_3$ | |
| 485 | 6-CH$_3$ | H | C≡CCH$_3$ | H | CH$_3$ | C$_2$H$_5$ | CH$_2$OH | |
| 486 | H | 5-CON(i-C$_3$H$_7$)$_2$ | C≡CCH$_3$ | H | CH$_3$ | C$_2$H$_5$ | CH$_2$OCH$_3$ | |
| 487 | H | 5-CO$_2$CH$_3$ | C≡CCH$_3$ | H | CH$_3$ | C$_2$H$_5$ | CH$_2$OH | |
| 488 | H | 5-CO$_2$H | C≡CCH$_3$ | H | CH$_3$ | C$_2$H$_5$ | CH$_3$ | |
| 489 | H | 5-I | C≡CCH$_3$ | H | CH$_3$ | C$_2$H$_5$ | CH$_2$OCH$_3$ | |
| 490 | H | 5-Cl | CN | H | CH$_3$ | CH$_3$ | CH$_3$ | |
| 491 | H | 5-Br | CN | H | CH$_3$ | CH$_3$ | CH$_2$OH | |
| 492 | 6-CH$_3$ | 5-Cl | CN | H | CH$_3$ | CH$_3$ | CH$_2$OCH$_3$ | |
| 493 | 6-Cl | 5-Cl | CN | H | CH$_3$ | CH$_3$ | CH$_3$ | |
| 494 | 4-SCH$_3$ | 5-OCH$_6$H$_5$ | CN | H | CH$_3$ | CH$_3$ | CH$_2$OH | |
| 495 | H | 5-COCH$_3$ | CN | H | CH$_3$ | CH$_3$ | CH$_2$OCH$_3$ | |
| 496 | H | 5-CN | CN | H | CH$_3$ | CH$_3$ | CH$_3$ | |
| 497 | H | 5-C≡CH | CN | H | CH$_3$ | CH$_3$ | CH$_2$OH | |
| 498 | H | 5-CH=CH$_2$ | CN | H | CH$_3$ | C$_2$H$_5$ | CH$_2$OCH$_3$ | |
| 499 | H | 5-C(OC$_2$H$_5$)=CH$_2$ | CN | H | CH$_3$ | C$_2$H$_5$ | CH$_3$ | |
| 500 | 6-CH$_3$ | H | CN | H | CH$_3$ | C$_2$H$_5$ | CH$_2$OH | |
| 501 | H | 5-CON(i-C$_3$H$_7$)$_2$ | CN | H | CH$_3$ | C$_2$H$_5$ | CH$_2$OCH$_3$ | |
| 502 | H | 5-CO$_2$CH$_3$ | CN | H | CH$_3$ | C$_2$H$_5$ | CH$_2$OH | |
| 503 | H | 5-CO$_2$H | CN | H | CH$_3$ | C$_2$H$_5$ | CH$_3$ | |
| 504 | H | 5-I | CN | H | CH$_3$ | C$_2$H$_5$ | CH$_2$OCH$_3$ | |

TABLE 2

4-Pyridines

| Compound No. | X | Y | $R^1$ | $R^2$ | $R^3$ | $R^4$ | $R^5$ | Melting Point (° C.) |
|---|---|---|---|---|---|---|---|---|
| 1 | H | H | C$_2$H$_5$ | H | CH$_3$ | CH$_3$ | CH$_3$ | |
| 2 | H | H | CH$_3$ | H | CH$_3$ | CH$_3$ | CH$_3$ | |
| 3 | H | H | n-C$_3$H$_7$ | H | CH$_3$ | CH$_3$ | CH$_3$ | |
| 4 | H | 2-Cl | CH$_3$ | H | CH$_3$ | CH$_3$ | CH$_3$ | |
| 5 | H | 2-Cl | C$_2$H$_5$ | H | CH$_3$ | CH$_3$ | CH$_3$ | |
| 6 | H | 2-Cl | n-C$_3$H$_7$ | H | CH$_3$ | CH$_3$ | CH$_3$ | |
| 7 | H | 2-Cl | CH$_2$CH=CH$_2$ | H | CH$_3$ | CH$_3$ | CH$_3$ | |
| 8 | H | 2-Cl | CH$_2$C≡CH | H | CH$_3$ | CH$_3$ | CH$_3$ | |
| 9 | H | 2-Cl | CH$_2$CF$_3$ | H | CH$_3$ | CH$_3$ | CH$_3$ | |
| 10 | H | 2-Cl | CH$_2$OCH$_3$ | H | CH$_3$ | CH$_3$ | CH$_3$ | |
| 11 | H | 2-Cl | CH$_2$CN | H | CH$_3$ | CH$_3$ | CH$_3$ | |
| 12 | H | 2-Cl | C$_6$H$_5$ | H | CH$_3$ | CH$_3$ | CH$_3$ | |
| 13 | H | 2-Cl | CH$_3$ | H | CH$_3$ | CH$_3$ | C$_2$H$_5$ | |
| 14 | H | 2-Cl | C$_2$H$_5$ | H | CH$_3$ | CH$_3$ | C$_2$H$_5$ | |
| 15 | H | 2-Cl | n-C$_3$H$_7$ | H | CH$_3$ | CH$_3$ | C$_2$H$_5$ | |
| 16 | H | 2-Cl | CH$_2$CH=CH$_2$ | H | CH$_3$ | CH$_3$ | C$_2$H$_5$ | |
| 17 | H | 2-Cl | CH$_2$C≡CH | H | CH$_3$ | CH$_3$ | C$_2$H$_5$ | |
| 18 | H | 2-Cl | CH$_2$CF$_3$ | H | CH$_3$ | CH$_3$ | C$_2$H$_5$ | |
| 19 | H | 2-Cl | CH$_2$OCH$_3$ | H | CH$_3$ | CH$_3$ | C$_2$H$_5$ | |
| 20 | H | 2-Cl | CH$_2$CN | H | CH$_3$ | CH$_3$ | C$_2$H$_5$ | |
| 21 | H | 2-Cl | C$_6$H$_5$ | H | CH$_3$ | CH$_3$ | C$_2$H$_5$ | |
| 22 | 6-Cl | 2-Cl | CH$_3$ | H | CH$_3$ | CH$_3$ | CH$_3$ | |
| 23 | 6-Cl | 2-Cl | C$_2$H$_5$ | H | CH$_3$ | CH$_3$ | CH$_3$ | |
| 24 | 6-Cl | 2-Cl | n-C$_3$H$_7$ | H | CH$_3$ | CH$_3$ | CH$_3$ | |
| 25 | 6-Cl | 2-Cl | CH$_2$CH=CH$_2$ | H | CH$_3$ | CH$_3$ | CH$_3$ | |
| 26 | 6-Cl | 2-Cl | CH$_2$C≡CH | H | CH$_3$ | CH$_3$ | CH$_3$ | |
| 27 | 6-Cl | 2-Cl | CH$_2$CF$_3$ | H | CH$_3$ | CH$_3$ | CH$_3$ | |
| 28 | 6-Cl | 2-Cl | CH$_2$OCH$_3$ | H | CH$_3$ | CH$_3$ | CH$_3$ | |
| 29 | 6-Cl | 2-Cl | CH$_2$CN | H | CH$_3$ | CH$_3$ | CH$_3$ | |
| 30 | 6-Cl | 2-Cl | C$_6$H$_5$ | H | CH$_3$ | CH$_3$ | CH$_3$ | |
| 31 | 6-Cl | 2-Cl | CH$_3$ | H | CH$_3$ | CH$_3$ | C$_2$H$_5$ | |
| 32 | 6-Cl | 2-Cl | C$_2$H$_5$ | H | CH$_3$ | CH$_3$ | C$_2$H$_5$ | |
| 33 | 6-Cl | 2-Cl | n-C$_3$H$_7$ | H | CH$_3$ | CH$_3$ | C$_2$H$_5$ | |
| 34 | 6-Cl | 2-Cl | CH$_2$CH=CH$_2$ | H | CH$_3$ | CH$_3$ | C$_2$H$_5$ | |
| 35 | 6-Cl | 2-Cl | CH$_2$C≡CH | H | CH$_3$ | CH$_3$ | C$_2$H$_5$ | |
| 36 | 6-Cl | 2-Cl | CH$_2$CF$_3$ | H | CH$_3$ | CH$_3$ | C$_2$H$_5$ | |
| 37 | 6-Cl | 2-Cl | CH$_2$OCH$_3$ | H | CH$_3$ | CH$_3$ | C$_2$H$_5$ | |
| 38 | 6-Cl | 2-Cl | CH$_2$CN | H | CH$_3$ | CH$_3$ | C$_2$H$_5$ | |
| 39 | 6-Cl | 2-Cl | C$_2$H$_5$ | H | CH$_3$ | CH$_3$ | n-C$_3$H$_7$ | |

TABLE 3

2-Pyridines

| Compound No. | X | Y | $R^1$ | $R^2$ | $R^3$ | $R^4$ | $R^5$ | Melting Point (° C.) |
|---|---|---|---|---|---|---|---|---|
| 1 | H | 4-Cl | $CH_3$ | H | $CH_3$ | $CH_3$ | $CH_3$ | |
| 2 | H | 4-Cl | $C_2H_5$ | H | $CH_3$ | $CH_3$ | $CH_3$ | |
| 3 | H | 4-Cl | n-$C_3H_7$ | H | $CH_3$ | $CH_3$ | $CH_3$ | |
| 4 | H | 4-Cl | $CH_2CH=CH_2$ | H | $CH_3$ | $CH_3$ | $CH_3$ | |
| 5 | H | 4-Cl | $CH_2C≡CH$ | H | $CH_3$ | $CH_3$ | $CH_3$ | |
| 6 | H | 4-Cl | $CH_2CF_3$ | H | $CH_3$ | $CH_3$ | $CH_3$ | |
| 7 | H | 4-Cl | $CH_2OCH_3$ | H | $CH_3$ | $CH_3$ | $CH_3$ | |
| 8 | H | 4-Cl | $CH_2CN$ | H | $CH_3$ | $CH_3$ | $CH_3$ | |
| 9 | H | 4-Cl | $C_6H_5$ | H | $CH_3$ | $CH_3$ | $CH_3$ | |
| 10 | H | 4-Cl | $CH_3$ | H | $CH_3$ | $CH_3$ | $C_2H_5$ | |
| 11 | H | 4-Cl | $C_2H_5$ | H | $CH_3$ | $CH_3$ | $C_2H_5$ | |
| 12 | H | 4-Cl | n-$C_3H_7$ | H | $CH_3$ | $CH_3$ | $C_2H_5$ | |
| 13 | H | 4-Cl | $CH_2CH=CH_2$ | H | $CH_3$ | $CH_3$ | $C_2H_5$ | |
| 14 | H | 4-Cl | $CH_2C≡CH$ | H | $CH_3$ | $CH_3$ | $C_2H_5$ | |
| 15 | H | 4-Cl | $CH_2CF_3$ | H | $CH_3$ | $CH_3$ | $C_2H_5$ | |
| 16 | H | 4-Cl | $CH_2OCH_3$ | H | $CH_3$ | $CH_3$ | $C_2H_5$ | |
| 17 | H | 4-Cl | $CH_2CN$ | H | $CH_3$ | $CH_3$ | $C_2H_5$ | |
| 18 | H | 4-Cl | $C_6H_5$ | H | $CH_3$ | $CH_3$ | $C_2H_5$ | |
| 19 | 4-Cl | 6-Cl | $CH_3$ | H | $CH_3$ | $CH_3$ | $CH_3$ | |
| 20 | 4-Cl | 6-Cl | $C_2H_5$ | H | $CH_3$ | $CH_3$ | $CH_3$ | |
| 21 | 4-Cl | 6-Cl | n-$C_3H_7$ | H | $CH_3$ | $CH_3$ | $CH_3$ | |
| 22 | 4-Cl | 6-Cl | $CH_2CH=CH_2$ | H | $CH_3$ | $CH_3$ | $CH_3$ | |
| 23 | 4-Cl | 6-Cl | $CH_2C≡CH$ | H | $CH_3$ | $CH_3$ | $CH_3$ | |
| 24 | 4-Cl | 6-Cl | $CH_2CF_3$ | H | $CH_3$ | $CH_3$ | $CH_3$ | |
| 25 | 4-Cl | 6-Cl | $CH_2OCH_3$ | H | $CH_3$ | $CH_3$ | $CH_3$ | |
| 26 | 4-Cl | 6-Cl | $CH_2CN$ | H | $CH_3$ | $CH_3$ | $CH_3$ | |
| 27 | 4-Cl | 6-Cl | $C_6H_5$ | H | $CH_3$ | $CH_3$ | $CH_3$ | |
| 28 | 4-Cl | 6-Cl | $CH_3$ | H | $CH_3$ | $CH_3$ | $C_2H_5$ | |
| 29 | 4-Cl | 6-Cl | $C_2H_5$ | H | $CH_3$ | $CH_3$ | $C_2H_5$ | |
| 30 | 4-Cl | 6-Cl | n-$C_3H_7$ | H | $CH_3$ | $CH_3$ | $C_2H_5$ | |
| 31 | 4-Cl | 6-Cl | $CH_2CH=CH_2$ | H | $CH_3$ | $CH_3$ | $C_2H_5$ | |
| 32 | 4-Cl | 6-Cl | $CH_2C≡CH$ | H | $CH_3$ | $CH_3$ | $C_2H_5$ | |
| 33 | 4-Cl | 6-Cl | $CH_2CF_3$ | H | $CH_3$ | $CH_3$ | $C_2H_5$ | |
| 34 | 4-Cl | 6-Cl | $CH_2OCH_3$ | H | $CH_3$ | $CH_3$ | $C_2H_5$ | |
| 35 | 4-Cl | 6-Cl | $CH_2CN$ | H | $CH_3$ | $CH_3$ | $C_2H_5$ | |
| 36 | 4-Cl | 6-Cl | $C_6H_5$ | H | $CH_3$ | $CH_3$ | $C_2H_5$ | |
| 37 | H | H | $C_2H_5$ | H | $CH_3$ | $CH_3$ | $CH_3$ | |
| 38 | 3-CN | 6-$CH_3$ | $CH_3$ | H | $CH_3$ | $CH_3$ | $CH_3$ | |
| 39 | 4-$CF_3$ | 6-$CH_3$ | n-$C_3H_7$ | H | $CH_3$ | $CH_3$ | $CH_3$ | |

The compounds of the invention are characterised by the melting points given in Table 1 and/or by the NMR data given in Table 4.

TABLE 4

Selected Proton NMR Data

| Compound No. (Table) | Proton NMR Data (δ) (ppm) |
|---|---|
| 4 (1) | 1.08(6H, m); 1.60(6H, s); 1.80(3H, s); 2.25–2.35(1H, m); 4.22(1H, d); 6.20(1H, br s); 7.26(1H, m); 8.26(2H, m). |
| 6 (1) | 1.03(3H, t); 1.65(6H, s); 2.00(2H, m); 4.48(1H, t); 6.4(1H, br s); 7.26(1H, m); 8.25(2H, m) |
| 9 (1) | 1.10(3H, t); 1.32(3H, t); 1.72(3H, s); 1.74(3H, s); 1.86(3H, s); 2.00(2H, m); 3.60(2H, m); 4.82(1H, m); 4.90(1H, d); 5.25(1H, d); 7.40(1H, m); 8.15(1H, m); 8.28(1H, m) |
| 11 (1) | 1.60(3H, s); 1.65(3H, s); 1.85(3H, s); 5.45(1H, s); 6.65(1H, br s); 7.25(1H, s); 7.40(3H, m); 7.50(2H, m); 8.25(2H, m) |
| 15 (1) | 1.06–1.10(3H, t); 1.16–1.20(3H, t); 1.20–1.64(12H, m); 1.66(3H, s); 1.70(3H, s); 2.02–2.10(2H, m); 2.22–2.26(2H, q); 3.50–4.00(2H, two br signals); 4.52–4.56 (1H, m); 6.46(1H, s); 7.24(1H, m); 8.30(1H, d); 8.40(1H, d) |
| 16 (1) | 1.04(3H, t); 1.08–1.12(3H, t); 1.62(3H, s); 1.64(3H, s); 1.98–2.04(2H, m); 2.14–2.20 (2H, q); 3.96(3H, s); 4.52–4.54(1H, m); 6.36(1H, s); 7.80(1H, m); 8.52(1H, d); 8.90(1H, d) |

Table 4 shows selected proton NMR data for certain compounds described in Tables 1 and 2. Chemical shifts are measured in ppm from tetramethylsilane, and deuterochloroform or dimethyl-$d_6$ sulphoxide was used as the solvent. The following abbreviations are used:

s = singlet
d = doublet
t = triplet
q = quartet
m = multiplet
br = broad
ppm = parts per million The compounds of general formula (I) may be prepared as outlined in Schemes 1 to 6 below, in which X, Y, $R^1$, $R^2$, $R^3$, $R^4$ and $R^5$ have the meanings given above, L is a leaving group such as halo, methylsulphonyloxy or arylsulphonyloxy (e.g. phenylsulphonyloxy), R is H or $C_{1-4}$ allyl, as indicated, R' is H or $C_{1-3}$ alkyl, R" is H or $C_{1-3}$ alkyl, provided that when R' and R" are both alkyl their total number of carbon atoms does not exceed 3, R'" is $C_{1-6}$ alkyl, optionally substituted benzyl or optionally substituted thienylmethyl, DMF is N,N-dimethylformamide and DMAP is 4-dimethylaminopyridine.

As shown in Scheme 1 the compounds of general formula (I) may be prepared by reacting an appropriately substituted pyridinol (II) with a compound of formula (III) in the presence of a suitable base and an aprotic solvent.

The pyridinol (II), which, in the case of a 2- or 4-pyridinol, may exist in tautomeric form, i.e. as the pyridone, is either commercially available or may be prepared by standard literature methods from commercially available materials.

The compound of formula (III) may be prepared as shown in Scheme 2 by reacting an amine (V) with an acid halide (IV), or the corresponding acid anhydride, in the presence of a suitable inorganic or organic base, such as potassium carbonate or diisopropylethylamine, in a suitable solvent, such as tetrahydrofuran or dichloromethane.

As shown in Scheme 3, amines of general formula (V), wherein $R^2$ is H, correspond to amines of general formula (IX) and may be prepared by alkylation of a silyl-protected aminoalkyne of general formula (VII) using a suitable base such as n-butyl lithium and reacting with a suitable alkylating reagent $R^5L$, such as an alkyl iodide, for example, methyl iodide, to form an alkylated compound of general formula (VIII). Where $R^5$ is halo, such as chloro, the reagent $R^5L$ is a suitable halogenating agent such as N-chlorosuccinimide. In a similar procedure, a silyl-protected aminoalkyne of general formula (VII) may be reacted with a carbonyl derivative, for example formaldehyde or acetaldehyde, using a suitable base, such as n-butyl lithium, to provide an aminoalkyne (VIII) in which $R^5$ is a hydroxyalkyl moiety. The silyl protecting group may then be removed from a compound of general formula (VIII) with, for example, an aqueous acid to form an aminoalkyne of general formula (IX). Aminoalkynes of general formula (IX) may be further derivatised, for instance when $R^5$ is a hydroxyalkyl group, for example, by reacting a compound of general formula (IX) with a silylating agent, for example tert-butyldimethylsilyl chloride, to give a trialkylsilyloxy derivative of general formula (IXa). In another example, a compound of general formula (IX) may be treated with a base, such as sodium hydride or potassium bis(trimethylsilyl)-amide, followed by a compound R'"—L, where L represents a halogen or sulphonate ester such as $OSO_2Me$, or $OSO_2$-4tolyl, to give compounds of general formula (IXb). In an alternative sequence, a compound of general formula (VIII) may be treated with a base, such as sodium or potassium bis(trimethylsilyl)amide, followed by a compound R'"—L, where L represents a halogen or sulphonate ester such as $OSO_2Me$, or $OSO_2$-4-tolyl to give, after removal of the silyl protecting group, compounds of general formula (IXb).

The $R^2$ group may be introduced into an aminoalkyne of general formula (IX) by known techniques to form an amine of general formula (V), where $R^2$ is other than H. Silyl-protected aminoalkynes of general formula (VII) may be obtained by reacting amines of general formula (VI) with 1,2-bis-(chlorodimethylsilyl)ethane in the presence of a suitable base, such as a tertiary organic amine base, for example, triethylamine.

The amine (VI) is either commercially available or may be prepared by standard literature methods (see, for example, EP-A-0834498) from commercially available materials.

Alternatively, the compounds of general formula (I) may be prepared by condensing a compound of formula (XI), wherein R is H, with the amine of formula (V) using suitable activating reagents such as 1-hydroxybenztriazole and N-(3-dimethylaminopropyl)-N'-ethyl carbodiimide hydrochloride as shown in Scheme 4.

The compound of formula (XI), wherein R is H, may be prepared by the hydrolysis of the corresponding ester of formula (XI), wherein R is $C_{1-4}$ alkyl, using known techniques. The ester of formula (XI), wherein R is $C_{1-4}$ alkyl and also the acid of formula (XI), wherein R is H, may be prepared by reacting the pyridinol (II) with an ester or acid of formula (X) in the presence of a suitable base, such as potassium carbonate, in a suitable solvent, such as N,N-dimethylformamide, under anhydrous conditions. The ester or acid of formula (X) is either commercially available or may be prepared by standard literature methods from commercially available materials.

In another method, shown in Scheme 5, the compounds of general formula (I) may be prepared by reacting an acid halide of formula (XIII) with the amine of formula (V) in a suitable solvent, such as dichloromethane, in the presence of a tertiary amine, such as triethylamine, and an activating agent, such as 4-dimethylaminopyridine.

The acid halide of formula (XIII) may be prepared by chlorinating a compound of formula (XII) with a suitable chlorinating agent, such as oxalyl chloride, in a suitable solvent, such as dichloromethane, and in the presence of, for example, N,N-dimethylformamide. The compound of formula (XII) corresponds to the compound of formula (XI) where R is H.

Other compounds of the invention may be prepared by transforming the substituents on the pyridine ring of compounds of formula (I) using known procedures or by the alkylation of compounds of formula (I) where $R^2$ is H.

Alternatively, as shown in Scheme 6, compounds of the general formula (XI), wherein R is $C_{1-4}$ alkyl, may be prepared under Mitsunobu conditions by reacting a pyridinol of general formula (II) with a compound of the general formula (XIV) using a phosphine, such as triphenyl phosphine, and an azoester, such as diethyl azodicarboxylate.

Similarly, compounds of general formula (I) may be prepared by reacting a compound of general formula (XVI) with a pyridinol of general formula (II) under Mitsunobu conditions using a phosphine, such as triphenyl phosphine, and an azoester, such as diethyl azodicarboxylate. Compounds of general formula (XVI) may be prepared from a compound of general formula (XV) and an amine of general formula (V) using suitable activating reagents such as 1-hydroxybenzotriazole and N-(3-dimethylaminopropyl)-N'-ethyl-carbodiimide hydrochloride. Compounds (XIV) and (XV) are either known compounds or may be made from known compounds.

Scheme 1

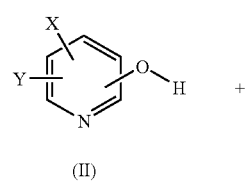

(II)

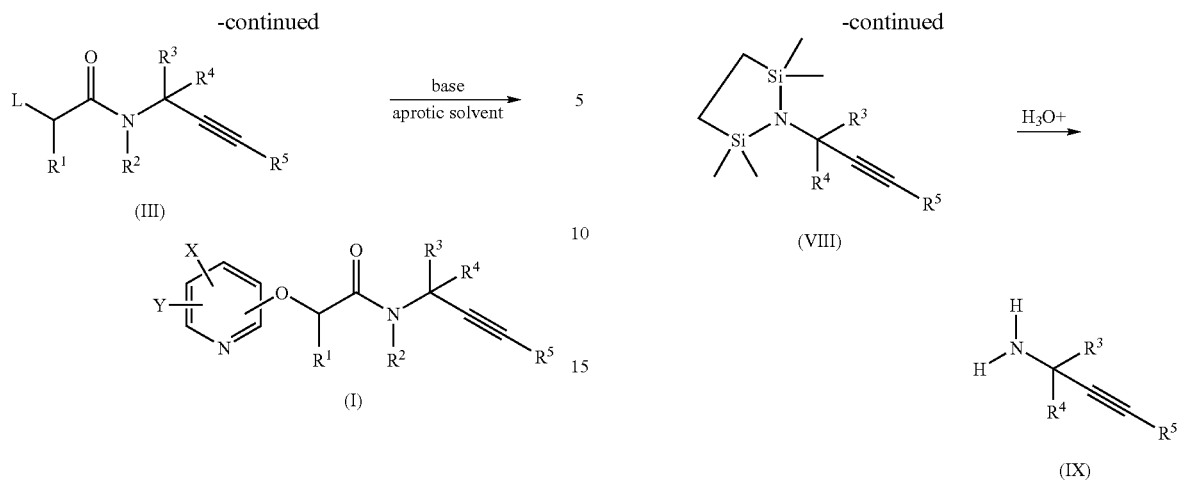
Scheme 2
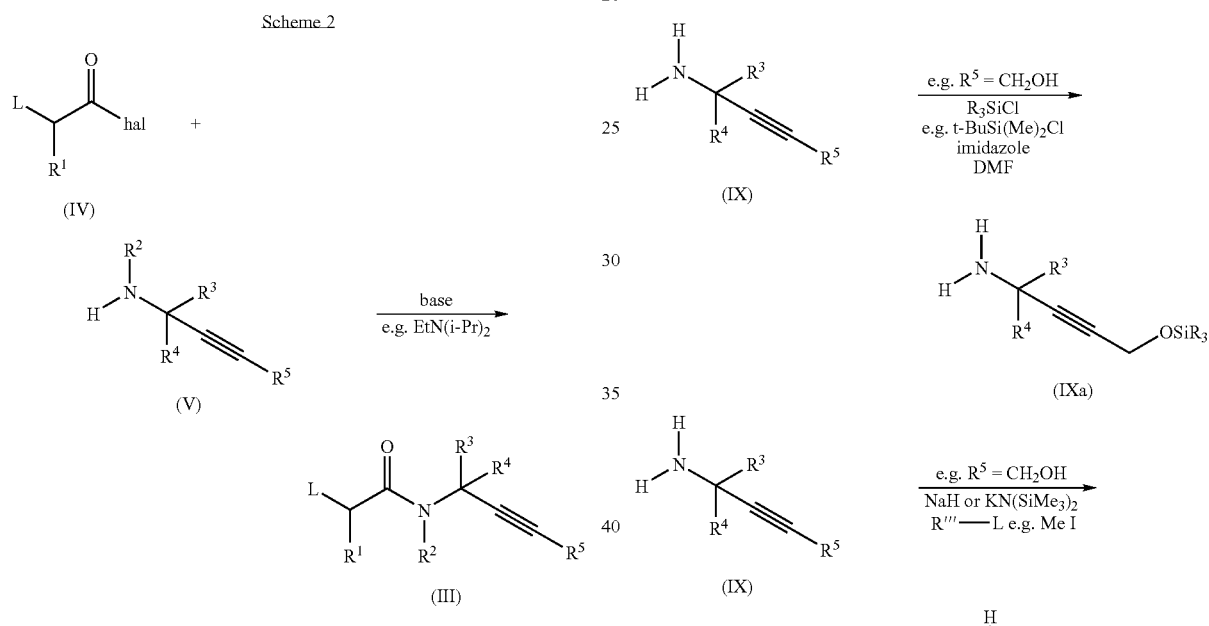
Scheme 3
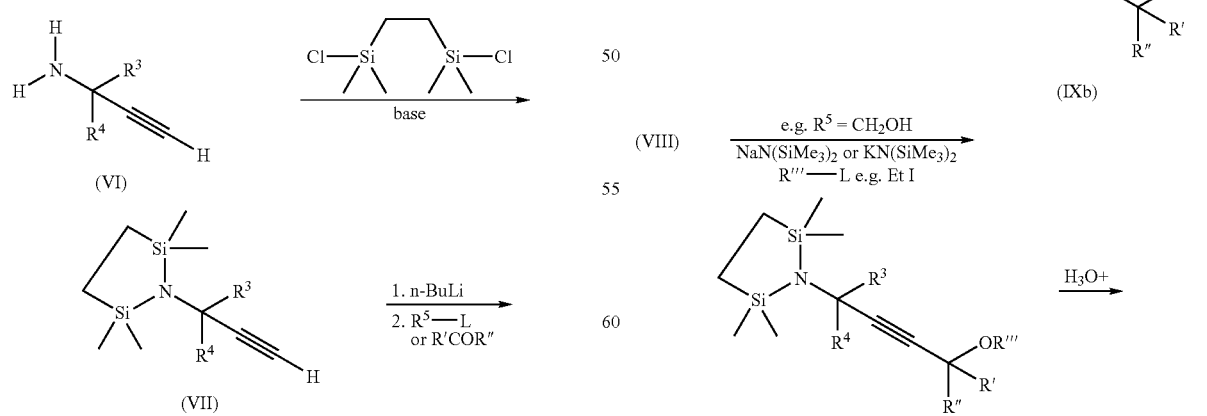

-continued
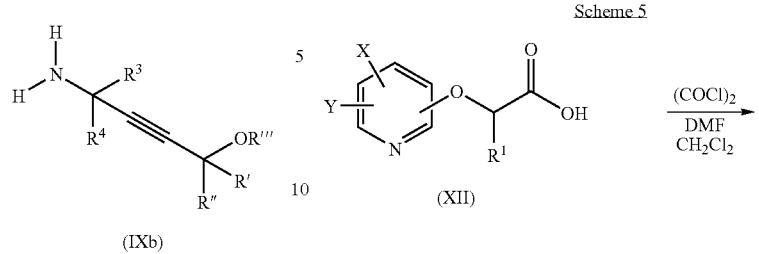
Scheme 4
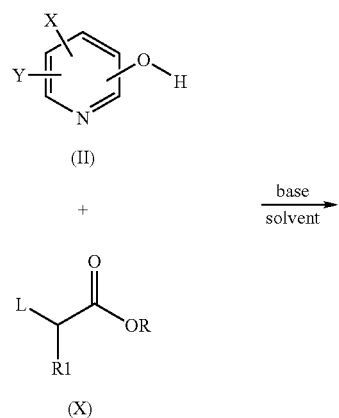
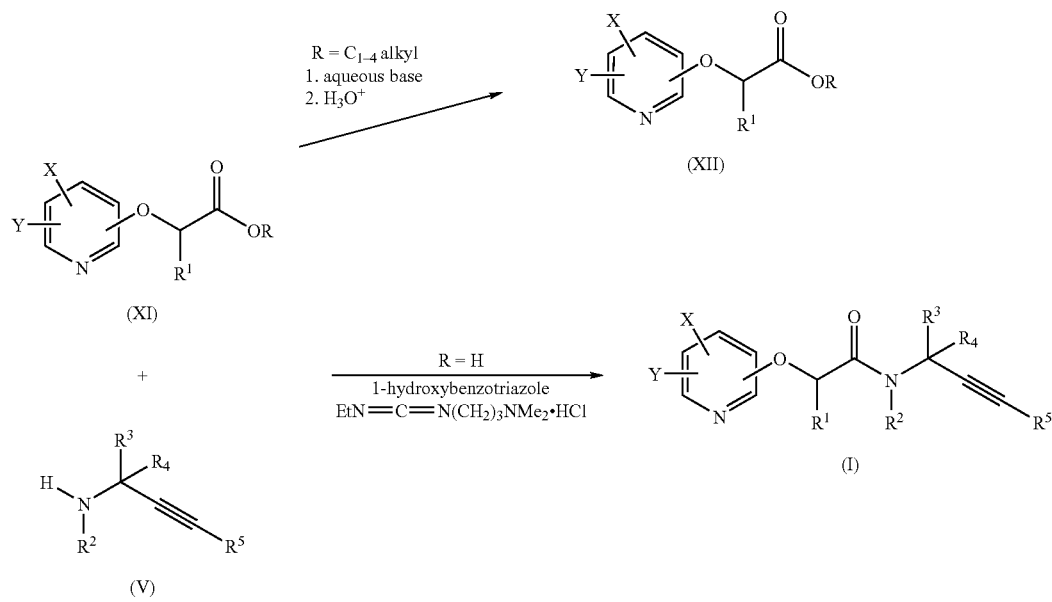

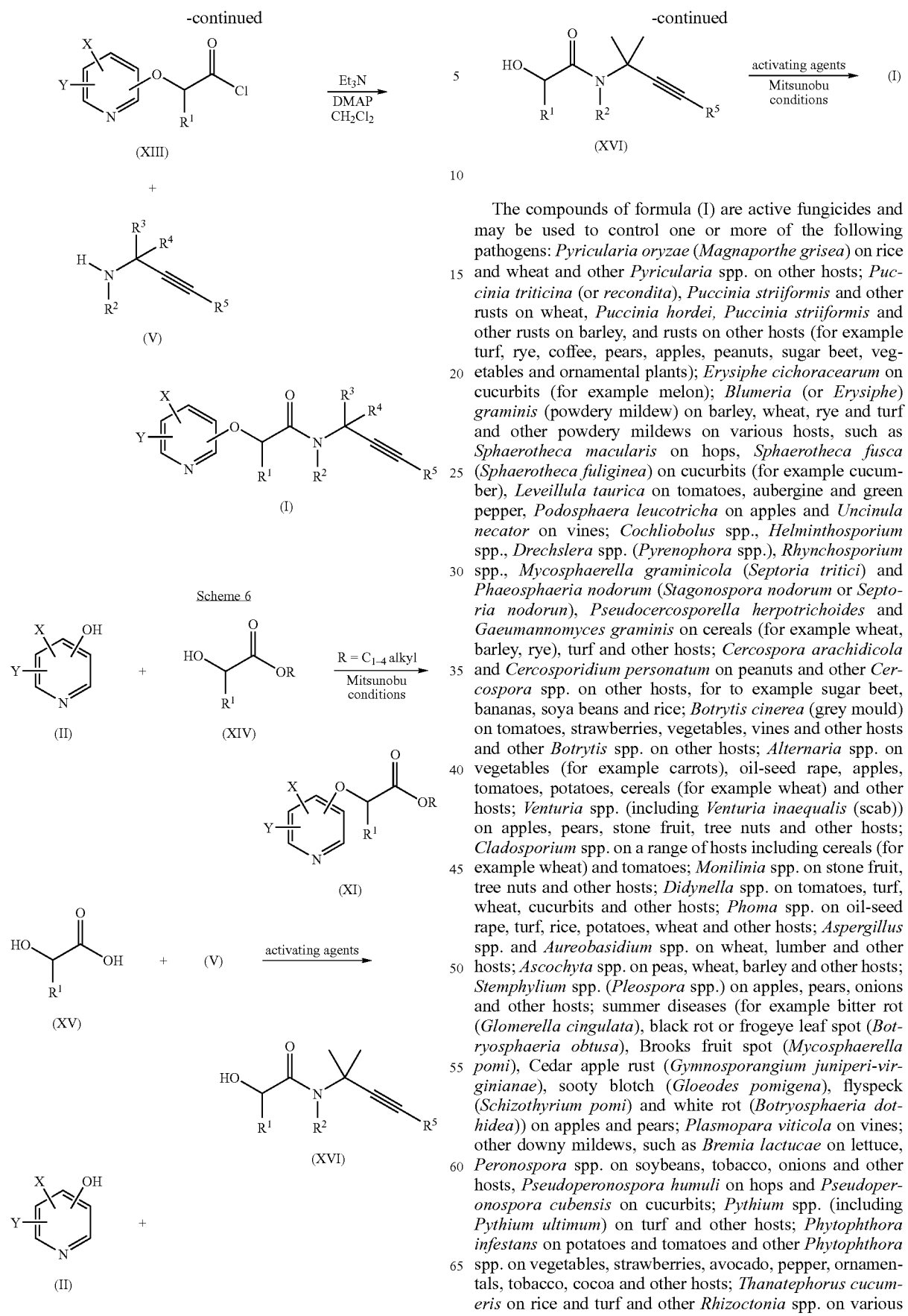

The compounds of formula (I) are active fungicides and may be used to control one or more of the following pathogens: *Pyricularia oryzae* (*Magnaporthe grisea*) on rice and wheat and other *Pyricularia* spp. on other hosts; *Puccinia triticina* (or *recondita*), *Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorun*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for to example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didynella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale, Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum, Penicillium italicum* and *Trichodenna viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodernium seditiosum*) or lumber, notably *Cephaloascus fragrans, Ceratocystis* spp., *Ophiostoma piceae, Penicillium* spp., *Trichoderna pseudokoningii, Trichoderna viride, Trichoderna harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

The compounds of formula (I) show particularly good activity against the Oomycete class of pathogens such as *Phytophthora infestans, Plasmopara* species, e.g. *Plasmopara viticola* and *Pythium* species e.g. *Pythium ultimum*.

A compound of formula (I) may move acropetally, basipetally or locally in plant tissue to be active against one or more fungi. Moreover, a compound of formula (I) may be volatile enough to be active in the vapour phase against one or more fungi on the plant.

The invention therefore provides a method of combating or controlling phytopathogenic fungi which comprises applying a fungicidally effective amount of a compound of formula (I), or a composition containing a compound of formula (I), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (I) are preferably used for agricultural, horticultural and turfgrass purposes in the form of a composition.

In order to apply a compound of formula (I) to a plant, to a seed of a plant, to the locus of the plant or seed or to soil or any other growth medium, a compound of formula (I) is usually formulated into a composition which includes, in addition to the compound of formula (I), a suitable inert diluent or carrier and, optionally, a surface active agent (SFA). SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of fungi such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (I) and a suitable carrier or diluent therefor.

In a still further aspect the invention provides a method of combating and controlling fungi at a locus, which comprises treating the fungi, or the locus of the fungi, with a fungicidally effective amount of a composition comprising a compound of formula (I).

The compositions can be chosen from a number of formulation types, including dustable powders (DP), soluble powders (SP), water soluble granules (SG), water dispersible granules (WG), wettable powders (WP), granules (GR) (slow or fast release), soluble go concentrates (SL), oil miscible liquids (OL), ultra low volume liquids (UL), emulsifiable concentrates (EC), dispersible concentrates (DC), emulsions (both oil in water (EC) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from preformed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$–$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SPAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be SFAs of the to cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SPAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethyleneglycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, VVPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a ferdliser to and a compound of formula (I).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (I) alone. Further the other fungicide may have a synergistic effect on the fungicidal activity of the compound of formula (I).

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of fungicidal compounds which may be included in the composition of the invention are AC 382042 (N-(1-cyano-1,2-dimethylpropyl)-2-(2,4-dichlorophenoxy) propionamide), acibenzolar-S-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquinolate, copper sulphate, copper tallate, and Bordeaux mixture, cyamidazosulfamid, cyazofamid (IK-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, O,O-di-iso-propyl-S-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)-N-benzyl-N([methyl(methylthioethylideneaminooxycarbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, fefimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thiabendazole, thifluzamide, 2-(thiocyanomethylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

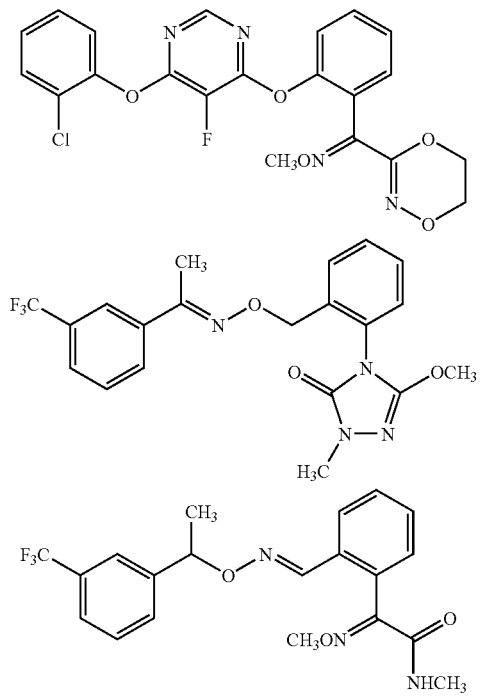

The compounds of formula (I) may be mixed with soil, peat or other rooting media for the protection of plants against seed-borne, soil-borne or foliar fungal diseases.

Some mixtures may comprise active ingredients that have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples in which the following abbreviations are used along with the abbreviations given in Table 4:
ml=millilitres DMSO=dimethylsulphoxide
g=grammes NMR=nuclear magnetic resonance
m.p. =melting point

EXAMPLE 1

This Example illustrates the preparation of (a) 2-(5-chloro-3-pyridyloxy)-N-(2-methylpent-3-yn-2-yl)butyramide (Compound No. 8 of Table 1); (b) 2-(5chloro-3-pyridyloxy)-N-(4methylhex-2-yn-4-yl)butyramide (Compound No.136 of Table 1); (c) 2-(5-chloro-3-pyridyloxy)-N-(6-methylhept-4-yn-6-yl)butyramide (Compound No. 120 of Table 1); and (d) 2-(5-bromo-3-pyridyloxy)-N-(6-methylhept4-yn-6-yl)butyramide (Compound No. 128 of Table 1)

Stage 1: Preparation of methyl
2-(5chloro-3-pyridyloxy)butyrate

5-Chloro-3-pyridinol (10.0 g) was dissolved in anhydrous N,N-dimethyl formamide (150 ml) containing anhydrous potassium carbonate (21.2 g) and methyl 2-bromobutyrate (16.4 ml). The mixture was stirred at 70° C. for 1.5 hours and allowed to cool to ambient temperature. The mixture was poured into water, extracted with diethyl ether (three times) and the combined extracts were washed with water (twice), dried over magnesium sulphate and evaporated under reduced pressure to give the required product as a pale brown oil, 27.4 g.

$^1$H NMR (CDCl$_3$) δ: 1.08–1.12 (3H, t); 2.00–2.08 (2H, m); 3.80 (3H, s); 4.60–4.64 (1H, m); 7.20 (1H, m); 8.08 (1H, m); 8.24 (1H, m).

Stage 2: Preparation of
2-(5-chloro-3-pyridyloxy)butyric acid.

The product from Stage 1 (27.4 g) was treated with a solution of sodium hydroxide (9.6 g) in water (50 ml) then stirred at 90° C. for 1.5 hours. The mixture was cooled to ambient temperature, diluted with water then washed with ethyl acetate. The aqueous phase was separated, acidified with concentrated hydrochloric acid and extracted with ethyl acetate (three times). The extracts were combined, washed with brine and dried over magnesium sulphate. The solvent was evaporated under reduced pressure to give the required product as a pale brown solid, 24.8 g, m.p. 98–101° C.

$^1$H NMR (CDCl$_3$) δ: 1.10–1.14 (3H, t); 2.02–2.14 (2H, m); 4.62–4.66 (1H, m) 7.36 (1H, s); 8.18–8.22 (2H, m); 8.88 (1H, br s).

Stage 3: Preparation of 2-(5-chloro-3-pyridyloxy)-
N-(2-methylpent-3-yn-2-yl)butyramide To a stirred solution of 4-aminomethyl-pent-2-yne hydrochloride (2.67 g; prepared as described below) in dry N,N-dimethyl formamide (150 ml) at ambient temperature was added dry triethylamine (4.2 ml). The mixture was stirred at ambient temperature for 5 minutes and 1-hydroxybenzotriazole hydrate (2.97 g), N-(3-dimethylaminopropyl)-N'-ethyl carbodiimide hydrochloride (4.22 g) and 2-(5-chloro-3-pyridyloxy)butyric acid (4.53 g) were added sequentially. The mixture was stirred at ambient temperature for 2.75 hours, stored at ambient temperature for 18 hour and poured into water. The product was extracted into diethyl ether (three times) and the extracts were combined, washed with aqueous sodium o hydrogen carbonate (twice), water (twice) and dried over magnesium sulphate. The solvent was evaporated under reduced pressure and the residual gum fractionated by chromatography (silica: diethyl ether) to give a pale yellow oil, which was triturated with hexane to give the required product as a colourless solid, 4.5 g, m.p. 87–89° C.

$^1$H NMR (CDCl$_3$) δ: 1.02–1.06 (3H, t); 1.60 (6H, s); 1.82 (3H, s); 1.94–2.02 (2H, q); 4.40–4.44 (1H, t); 6.30 (1H, br s); 7.24–7.26 (1H, m); 8.24–8.26 (2H, m).

Preparation of 4-aminomethylpent-2-yne hydrochloride (for use in Stage 3)

Step 1

3-Amino-3-methylbutyne (commercially available as 90% aqueous solution; 16.6 g) was dissolved in dichloromethane (150 ml), dried over sodium sulphate and filtered to give a solution containing 14.9 g of amine. To the stirred solution of amine under an atmosphere of nitrogen at ambient temperature was added dry triethylamine (48.4 ml). 1,2-Bis-(chlorodimethylsilyl)ethane (38.98 g) in dichloromethane (100 ml) was then added dropwise, maintaining the reaction temperature at 15° C. by cooling. The mixture was stirred for 3 hours, the colourless solid, which had formed during the reaction, was filtered from solution and the filtrate was evaporated under reduced pressure to give a paste. The paste was extracted into hexane and refiltered. The filtrate was evaporated under reduced pressure and the oil obtained was distilled to give 1-(1,1-dimethyl-2-propynyl)-2,2,5,5-tetramethyl-1-aza-2,5-disilacyclopentane, 21.5 g, b.p. 41° C. at 0.06 mm Hg pressure.

$^1$H NMR (CDCl$_3$) δ: 0.16 (12H, s); 0.60 (4H, s); 1.48 (6H, s); 2.24 (1H, s).

Step 2

The product from Step 1 (13.0 g) in dry tetrahydrofuran (140 ml) was cooled to −70° C. under an atmosphere of nitrogen with stirring and a solution of n-butyl lithium (23.1 ml of 2.5M solution in hexanes) was added at −65 to −70° C. during 5 minutes. The mixture was allowed to warm to −5° C. and methyl iodide (3.93 ml) was added dropwise over 10 minutes. The reaction mixture was allowed to warm to 10° C. when an exothermic reaction occurred. The mixture was maintained at 20° C. by cooling for 2 hours then evaporated under reduced pressure to a small volume. The residue was dissolved in hexane, filtered to remove the insoluble material and evaporated under reduced pressure to give 1-(1,1-dimethyl-2-butynyl)-2,2,5,5-tetramethyl-1-aza-2,5-disilacyclopentane as a yellow oil, 13.0 g.

$^1$H NMR (CDCl$_3$) δ: 0.10 (12H, s); 0.56 (4H, s); 1.40 (6H, s); 1.72 (3H, s).

Step 3

The product from Step 2 (13.0 g) was added slowly to aqueous hydrochloric acid (35 ml, 4M) at 0° C. with stirring. The emulsion formed was stirred for 0.5 hours then taken to pH14 with aqueous sodium hydroxide (4M) while maintaining the reaction mixture at 0° C. by cooling in ice. The aqueous mixture was extracted into dichloromethane (three times) and the extracts combined, dried over sodium sulphate and filtered. The filtrate was made acidic by adding an excess of a saturated solution of hydrogen chloride in 1,4-dioxan. The mixture was concentrated under reduced pressure until a colourless precipitate was formed. Hexane was added to the suspension and the solid was filtered from solution. The solid was washed with dry diethyl ether and placed under vacuum to remove any residual solvents to give the required product as a colourless solid, 5.0 g.

$^1$H NMR (d$_6$-DMSO) δ: 1.74 (6H, s); 1.82 (3H, s); 8.74 (3H, br s).

The following amines were prepared using a similar procedure to that described for 4-amino-4-methylpent-2-yne hydrochloride in Steps 2 and 3 above.

4-Amino4methylhex-2-yne hydrochloride $^1$H NMR (CDCl$_3$) δ: 1.00–1.06 (3H, t); 1.66 (3H, t); 1.84 (3H, s); 1.84–2.06 (2H, m); 8.65 (3H, broad singlet).

5-Amino-5-methylhex-3-yne hydrochloride $^1$H NMR (d6-DMSO) δ: 1.10–1.16 (3H, t); 1.74 (6H, s); 2.16–2.20 (2H, q); 8.70 (3H, broad signal).

6-Amino-6-methylheptyne hydrochloride $^1$H NMR (CDCl$_3$) δ: 0.94–1.00 (3H, t); 1.48–1.58 (2H, m); 1.72-(6H, s); 2.14–2.18 (2H, t); 8.72-(3H, broad singlet).

In a similar procedure to that described in Stage 3 above, the following compounds of the invention were prepared from 2-(5-chloro-3-pyridyloxy)butyric acid or 2 (5-bromo-3-pyridyloxy)butyric acid and the corresponding amine above.

2-(5-Chloro-3-pyridyloxy)-N-(4-methylhex-2-yn-4 yl)butyraride (Compound No.136 of Table 1), gum,
$^1$H NMR spectrum is consistent with the sample being a 1:1 mixture of diastereoisomers.

$^1$H NMR (CDCl$_3$) δ: 0.86–0.94 (3H, two t); 1.02–1.06 (3H, t); 1.60–1.62-(3H, two s); 1.70–1.80 (1H, m); 1.84 (3H, s); 1.96–2.04 (2H, m); 2.04–2.14 (1H, m); 4.40–4.44 (1H, m); 6.24 (1H, broad singlet); 7.24–7.26 (1H, m); 8.26 (2H, s).

2-(5-Chloro-3-pyridyloxy)-N-(6-methylhept-4-yn-6-yl)butyramide (Compound No. 120 of Table 1), colourless solid, m.p. 70–71° C.

$^1$H NMR (CDCl$_3$) δ: 0.96 (3H, t); 1.02 (3H, t); 1.50 (2H, m); 1.61 (6H, s); 1.99 (2H, m); 2.14 (2H, t); 4.42-(1H, t); 6.31 (1H, broad singlet); 7.24 (2H, m); 8.26 (1H, m).

2-(5-Bromo-3-pyridyloxy)-N-(6-methylheptyn-6-yl) butyramide (Compound No. 128 of Table 1), characterised by the $^1$H NMR spectrum (data incomplete due to overlapping peaks with NMR solvent).

$^1$H NMR (CD$_3$CN) δ: 0.91 (3H, t); 0.95 (3H, t); 1.42 (2H, m); 1.48 (3H, s); 1.50 (3H, s); 4.45 (1H, t); 6.72-(1H, broad singlet); 7.46 (1H, m); 8.23 (1H, m); 8.27 (1H, m).

EXAMPLE 2

Preparation of 2-(5chloro-3-pyridyloxy)-N-(2-methylpent-3-yn-2-yl)valeramide (Compound No. 3 of Table 1)

This compound was prepared using a similar procedure to that described in Stage 3 of Example 1 except that 2-(5-chloro-3-pyridyloxy)valeric acid was used in place of 2-(5-chloro-3-pyridyloxy)butyric acid. The compound was characterised as follows: m.p. 73–75° C.; $^1$H NMR (CDCl$_3$) δ: 0.94–0.98 (3H, t); 1.42–1.56 (2H, m); 1.60 (6H, s); 1.80 (3H, s); 1.90–1.96 (2H, m); 4.40–4.46 (1H, t); 6.26 (1H, s); 7.24–7.26 (1H, m); 8.24–8.28 (2H, m).

The 2-(5-chloro-3-pyridyloxy)valeric acid was prepared using a similar procedure to that described in Stage 2 of Example 1 except that ethyl 2-(5-chloro-3-pyridyloxy)valerate was used in place of methyl 2-(5-chloro-3-pyridyloxy) butyrate. The compound was characterised as follows: m.p.

89–91° C.; $^1$H NMR (CDCl$_3$) δ: 0.96–1.02 (3H, t); 1.52–1.64 (2H, m); 1.98–2.06 (2H, m); 4.68–4.72 (1H, m); 5.95 (1H, br s); 7.34 (1H, s); 8.16 (1H, s); 8.22 (1H, s).

The ethyl 2-(5-chloro-3-pyridyloxy)valerate was prepared using a similar procedure to that described in Stage 1 of Example 1 except that ethyl 2-bromovalerate was used in place of methyl 2-bromobutyrate. The compound was characterised as follows: $^1$H NMR (CDCl$_3$) δ: 0.96–1.02 (3H, t); 1.24–1.30 (3H, t); 1.50–1.60 (2H, m); 1.90–2.02 (2H, m); 4.20–4.26 (2H, q); 4.60–4.64 (1H, m); 7.18 (1H, s); 8.22 (1H, s); 8.22 (1H, s).

EXAMPLE 3

Preparation of 2-(5-chloro-3-pyridyloxy)-N-(2-methylpent-3-yn-2-yl)phenylacetamide (Compound No. 11 of Table 1)

This compound was prepared using a similar procedure to that described in Stage 3 of Example 1 except that 2-(5-chloro-3-pyridyloxy)phenylacetic acid was used in place of 2-(5-chloro-3-pyridyloxy)butyric acid. The compound was characterised as follows: 1H NMR (CDCl$_3$) δ: 1.60 (3H, s); 1.65 (3H, s); 1.85 (3H, s); 5.45(1H, s); 6.65 (1H, br s); 7.25 (1H, s); 7.40 (3H, m); 7.50 (2H, m); 8.25 (2H, m).

The 2-(5-chloro-3-pyridyloxy)phenylacetic acid was prepared using a similar procedure to that described in Stage 2 of Example 1 except that methyl 2-(5-chloro-3-pyridyloxy)-2-phenylacetate was used in place of methyl 2-(5-chloro-3-pyridyloxy)butyrate. The compound was characterised as follows: $^1$H NMR (CDCl$_3$) δ: 5.65 (1H, s); 7.25 (1H, s); 7.35 (1H, s); 7.40 (3H, m); 7.60 (2H, m); 8.20 (1H, s); 8.30 (1H, s).

The methyl 2-(5-chloro-3-pyridyloxy)-2-phenylacetate was prepared using a similar procedure to that described in Stage 1 of Example 1 except that methyl 2-bromophenylacetate was used in place of methyl 2-bromobutyrate. The compound was characterised as follows: $^1$H NMR (CDCl$_3$) δ: 3.75 (3H, s); 5.65 (1H, s); 7.25 (1H, s); 7.40 (3H, m); 7.55 (2H, m); 8.25 (2H, m).

EXAMPLE 4

This Example illustrates the preparation of 3-(5-chloro-3-pyridyloxy)-N-(1-chloro-3-methylbut-1-yn-3-yl)butyramide (Compound No. 5 of Table 1)

2-(5-Chloro-3-pyridyloxy)butyric acid (0.35 g; prepared as described in Stage 2 of Example 1) was stirred in dry dichloromethane (5 ml) containing N,N-dimethylformamide (0.1 ml) and treated dropwise with oxalyl chloride (0.145 ml) at ambient temperature. The solution was stirred for 0.5 hours and added in portions to a mixture of 1-chloro-3-amino-3-methylbut-1-yne hydrochloride (0.25 g; prepared as described below), dry triethylamine (0.68 ml) and 4-dimethylaminopyridine (0.01 g) in dry dichloromethane (5 ml) with stirring at ambient temperature. The mixture was stirred for 1 hour, stored for 18 hours, diluted with further dichloromethane, washed with aqueous sodium hydrogen carbonate, dried over magnesium sulphate and evaporated under reduced pressure to give an oil. The oil was fractionated by chromatography (silica:hexane/ethyl acetate 3:1 by volume) to give a solid that was recrystallised from hexane to give the required product as a colourless solid, 0.15 g, m.p. 78–82° C.

Preparation of 1-chloro-3-amino-3-methylbut-1-yne hydrochloride 1-(1,1-Dimethyl-2-propynyl)-2,2,5,5-tetramethyl-1-aza-2,5-disilacyclopentane (3.0 g) in dry tetrahydrofuran (25 ml) was cooled to −50° C. with stirring under an atmosphere of nitrogen and then treated dropwise with a solution of n-butyl lithium in hexanes (8.3 ml; 1.6M). The mixture was allowed to warm to −25° C. and N-chlorosuccinimide (2.0 g) was added in one portion. The mixture was stirred at −25° C. for 1 hour and then allowed to warm to ambient temperature over 1 hour. The solution was acidified with 5% aqueous hydrochloric acid, washed with diethyl ether and the aqueous solution was made basic with aqueous sodium hydroxide. The mixture was extracted with diethyl ether, dried over magnesium sulphate, filtered and the filtrate then treated with a solution of hydrogen chloride in ethanol until acidic. The solvents were evaporated under reduced pressure to give the required product as a colourless solid, 0.5 g.

EXAMPLE 5

This Example illustrates the preparation of 2-(5-chloro-3-pyridyloxy)-N-methyl-N-(2-methylpent-3-yn-2-yl)butyramide (Compound No. 10 of Table 1)

To a solution of 2-(5-chloro-3-pyridyloxy)-N-(2-methylpent-3-yn-2-yl)butyramide (0.10 g; prepared as described in Example 1) in dry tetrahydrofuran (9 ml) was added sodium hydride (0.011 g) at ambient temperature under an atmosphere of nitrogen. The mixture was stirred for 0.75 hours, a solution of methyl iodide (0.023 ml) in dry tetrahydrofuran was added then the reaction mixture stirred for a further 0.5 hours at ambient temperature. The reaction was diluted with water, extracted with ethyl acetate (three times) and the extracts were combined, washed with brine, dried over magnesium sulphate and evaporated under reduced pressure. The residual oil was fractionated by chromatography (silica: hexane/ethyl acetate, 3:1 by volume) to give the required product as a beige solid, 0.075 g. m.p. 67–68° C. $^1$H NMR (CDCl$_3$) δ: 1.14 (3H, t); 1.68 (3H, s); 1.69 (3H, s); 1.85 (3H, s); 2.02 (2H, m); 3.20 (3H, s); 4.70 (1H, t); 7.18 (1H, m); 8.18 (1H, m); 8.20 (1H, m).

EXAMPLE 6

The preparation of 2-(5-chloro-3-pyridyloxy)-N-ethoxymethyl-N-(2-methylpent-3-yn-2-yl)butyramide (Compound No. 9 of Table 1)

This compound was prepared using a similar procedure to that described in Example 5 except that ethoxymethyl chloride was used in place of the methyl iodide. The compound, which was obtained as an oil, was characterised as follows: $^1$H NMR (CDCl$_3$) δ: 1.10 (3H, t); 1.32 (3H, t); 1.72 (3H, s); 1.74 (3H, s); 1.86 (3H, s); 2.00 (2H, m); 3.60 (2H, m); 4.82 (1H, m); 4.90 (1H, d); 5.25 (1H, d); 7.40 (1H, m); 8.15 (1H, m); 8.28 (1H, m).

EXAMPLE 7

The preparation of 2-(5-chloro-3-pyridyloxy)N-(2-methylhex-3-yn-2-yl)butyramide (Compound No 1 of Table 1)

This compound was prepared using a similar procedure to that described in Stage 3 of Example 1 except that 5-amino- 5-methylhex-3-yne hydrochloride was used in place of the 4-aminomethylpent-2-yne hydrochloride.

The 5-amino-5-methylhex-3-yne hydrochloride was prepared using a similar procedure to that described for preparing 4-amino4methylpent-2-yne hydrochloride in Example 1 but using ethyl iodide instead of methyl iodide in Step 2. The 5-amino-5-methylhex-3-yne hydrochloride was characterised as follows: $^1$H NMR (d$_6$-DMSO) δ: 1.10–1.16 (3H, t); 1.74 (6H, s); 2.16–2.20 (2H, q); 8.70 (3H, br s).

EXAMPLE 8

Preparation of 2-(5-bromo-3-pyridyloxy)-N-(2-methylpent-3-yn-2-yl)butyramide (Compound No. 13 of Table 1)

This compound was prepared using a similar procedure to that described in Stage 3 of Example 1 except that 2-(5-bromo-3-pyridyloxy)butyric acid was used in place of 2-(5-chloro-3-pyridyloxy)butyric acid. The compound was characterised as follows: colourless solid; m.p. 102–104° C.; $^1$H NMR (CDCl$_3$) δ: 1.02–1.06 (3H, t); 1.62 (6H, s); 1.82 (3H, s); 1.96–2.02 (2H, m); 4.40–4.44 (1H, m); 6.30 (1H, br s); 7.40 (1H, m); 8.28 (1H, d); 8.36 (1H, d).

The 2-(5-bromo-3-pyridyloxy)butyric acid was prepared using a similar procedure to that described in Stage 2 of Example 1 except that methyl 2-(5-bromo-3-pyridyloxy) butyrate was used in place of methyl 2-(5-chloro-3-pyridyloxy)butyrate. The compound was characterised as follows: m.p. 100–102° C.; $^1$H NMR (CDCl$_3$) δ: 1.12–1.18 (3H, t); 2.04–2.14 (2H, m); 4.64–4.68 (1H, m); 7.36 (1H, br s); 7.54 (1H, m); 8.24 (1H, d); 8.34 (1H, d).

The methyl 2-(5-bromo-3-pyridyloxy)butyrate was prepared using a similar procedure to that described in Stage 1 of Example 1 except that 5-bromo-3-pyridinol was used in place of 5-chloro-3-pyridinol. The compound was characterised as follows: $^1$H NMR (CDCl$_3$) δ: 1.06–1.10 (3H, t); 2.00–2.06 (2H, m); 3.80 (3H, s); 4.60–4.64 (1H, m); 7.34 (1H, m); 8.22 (1H, d); 8.32 (1H, d).

The 5-bromo-3-pyridinol was prepared as follows.

Step 1

3,5-Dibromopyridine (30.0 g) was added to a stirred solution of sodium methoxide (prepared from 11.6 g of sodium) in methanol (120 ml) and heated to reflux for 70 hours under an atmosphere of nitrogen. The mixture was cooled to ambient temperature, poured into water (1 l), extracted with diethyl ether (three times) and the extracts combined, washed with water (four times) and dried (magnesium sulphate). The solvent was evaporated under reduced pressure to give 3-bromo-5-methoxypyridine as a colourless liquid, 19.3 g, which slowly crystallised on storing.

$^1$H NMR (CDCl$_3$) δ: 3.86 (3H,s); 7.35–7.37 ((1H, m); 8.248.30 (2H, m).

Step 2

The product from Step 1 (11.58 g) was mixed with aqueous hydrobromic acid (60 ml; 48% w/v) and heated to 120° C. for 48 hours with stirring. The mixture was cooled to ambient temperature, poured into water and made alkaline with aqueous sodium hydroxide (2M). The aqueous phase was extracted with diethyl ether (twice) and the organic extracts discarded. The aqueous phase was taken to pH 6–7 with concentrated hydrochloric acid and the precipitate that had formed was filtered from solution. The solid was washed with water and sucked to dryness under vacuum to give the required product as a colourless solid, 8.67 g; m.p. 151–154° C.

$^1$H NMR (d$_6$-DMSO) δ: 7.52–7.54 (1H, m); 8.22–8.30 (2H, m); 10.50–10.80 (1H, br s).

EXAMPLE 9

Preparation of 2-(5-bromo-3-pyridyloxy)-N-(2-methylhex-3-yn-2-yl)butyramide (Compound No. 14 of Table 1)

This compound was prepared using a similar procedure to that described in Stage 3 of Example 1 except that 5-amino-5-methylhex-3-yne hydrochloride was used in place of 4-amino-4-methylpent-2-yne hydrochloride and 2-(5-bromo-3-pyridyloxy)butyric acid was used in place of 2-(5-chloro-3-pyridyloxy)butyric acid. The compound was characterised as follows: colourless solid, m.p. 90–92° C.; $^1$H NMR (CDCl$_3$) δ: 1.02–1.06 (3H, t); 1.10–1.14 (3H, t); 1.62 (6H, s); 1.96–2.02 (2H, m); 2.16–2.22 (2H, m); 4.424.46 (1H, m); 6.30 (1H, br s); 7.40 (1H, m); 8.30 (1H, d); 8.36 (1H, d).

The 5-amino-5-methylhex-3-yne hydrochloride was prepared as described in Example 7 and the 2-(5-bromo-3-pyridyloxy) butyric acid was prepared as described in Example 8.

EXAMPLE 10

This Example illustrates the preparation of (a) 2-(5-methoxycarbonyl-3-pyridyloxy)-N-(5-methylhex-3-yn-5-yl)butyramide (Compound No. 16 of Table 1); (b) 2-(5-carboxy-3-pyridyloxy)-N-(5-methylhex-3-yn-5-yl) butyramide (Compound No. 17 of Table 1); (c) 2-(5-(N,N-diisopropylaminocarbonyl)-3-pyridyloxy)-N-(5-methylhex-3-yn-5-yl)butyramide (Compound No. 15 of Table 1); (d) 2-(2,6-Dichloropyridyloxy)- N-(4methylpent-2-yn-4-yl)butyramide (Compound No. 23 of Table 2); and (e) 2-(2,6-Dichloro4pyridyloxy)-N-(6-methylheptyn-6-yl)butyramide (Compound No. 40 of Table 2)

Stage 1

Preparation of 2-bromo-N-(5-methylhex-3-yn-5-yl)butyramide.

5-Amino-5-methylhex-3-yne hydrochloride (2.21 g) was dissolved in dry dichloromethane (50 ml) and cooled to 5° C. with stirring. 2-Bromobutyryl bromide (3.45 g) was added to the mixture and dry triethylamine (4.17 ml) was added dropwise while maintaining the reaction temperature between 8–15° C. by cooling during the addition. The suspension, which had formed during the reaction, was diluted with further dry dichloromethane (20 ml) and stirred at 5° C. for 0.5 hours. The mixture was allowed to warm to ambient temperature and stirred for a further 2 hours. The reaction was treated with water and extracted with dichloromethane. The organic phase was separated, washed with water (three times), dried over magnesium sulphate and evaporated under reduced pressure to give a brown oil. The oil was fractionated by chromatography (silica; hexane/diethyl ether, 1:1 by volume) to give the required product, as a pale yellow solid, 3.17 g, m.p. 53–55° C.

$^1$H NMR (CDCl$_3$) δ: 1.04 (3H, t); 1.10–1.14 (3H, t); 1.64 (6H, s); 2.02–2.16 (2H, m); 2.16–2.22 (2H, q); 4.20–4.24 (1H, m); 6.44 (1H, s).

Stage 2

Preparation of 2-(5-methoxycarbonyl-3-pyridyloxy)-N-(5-methylhex-3-yn-5-yl)butyramide (Compound No 16 of Table 1)

3-Hydroxy-5-methoxycarbonylpyridine (1.68 g, prepared using the method described in *Bull. Acad. Sci.* (Chem. Div.), (1976), 598) and 2-bromobromo-N-(5-methylhex-3-yn-5-yl)-butyramide (3.06 g) were dissolved in dry N,N-dimethylformamide (30 ml) containing anhydrous potassium carbonate (2.35 g). The mixture was heated to 70° C. for 3 hours with stirring, cooled to ambient temperature, diluted with water and extracted with diethyl ether (three times). The organic extracts were combined, washed with water (three times), dried over magnesium sulphate and evaporated under reduced pressure to give a brown gum. The gum was fractionated by chromatography (silica; diethyl ether) to give the required product, 2.38 g, as a yellow oil.

$^1$H NMR (CDCl$_3$) δ: 1.04 (3H, t); 1.08–1.12 (3H, t); 1.62 (3H, s); 1.64 (3H, s); 1.98–2.04 (2H, m); 2.14–2.20 (2H, q); 3.96 (3H, s); 4.52–4.54 (11H, m); 6.36 (1H, s); 7.80 (1H, m); 8.52 (1H, d); 8.90 (1H, d).

Stage 3

Preparation of 2-(5-carboxy-3-pyridyloxy)-N-(5-methylhex-3-yn-5-yl)butyramide (Compound No. 17 of Table 1)

The product from Stage 2 (2.18 g) was dissolved in propan-2-ol (25 ml) and a solution of sodium hydroxide (0.28 g) in water (10 ml) was added at ambient temperature. The mixture was stirred for 1.5 hours, stored at ambient temperature for 18 hours and evaporated under reduced pressure to remove the propan-2-ol. The residual aqueous solution was diluted with water, washed with ethyl acetate and the aqueous phase was acidified with hydrochloric acid. The acidic aqueous phase was extracted with ethyl acetate (three times) and the extracts were combined, washed with water (twice), dried over magnesium sulphate and evaporated under reduced pressure to give a solid. The solid was washed with a small volume of diethyl ether then filtered from solution to give the required product as a colourless solid; 1.47 g; m.p. 162–164° C.

$^1$H NMR (CDCl$_3$) δ: 1.02–1.12 (6H, m); 1.62 (3H, s); 1.64 (3H, s); 2.00–2.08 (2H, m); 2.14–2.20 (2H, q); 4.68–4.72 (1H, m); 4.60–5.30 (1H, br s); 6.48 (1H, s); 8.00 (1H, m); 8.60 (1H, d); 9.00 (1H, d).

Stage 4

Preparation of 2-(5-(N,N-diisopropylaminocarbonyl)-3-pyridyloxy)N-(5-methylhex-3-yn-5-yl)butyramide (Compound No. 15 of Table 1)

The product from Stage 3 (0.22 g) in dry N,N-dimethylformamide (5 ml) containing N-(3-(dimethylaminopropyl))-N'-ethylcarbodiimide hydrochloride (0.14 g) was stirred at ambient temperature and treated dropwise with diisopropylamine (0.20 ml). The mixture was stirred at ambient temperature for 2 hours, diluted with water, extracted with diethyl ether (three times) and the organic fractions combined, washed with aqueous sodium hydrogen carbonate (twice), water (twice) and dried over magnesium sulphate. The solvent was evaporated under reduced pressure and the residual gum was fractionated by chromatography (silica; ethyl acetate) to give the required product as a colourless gum, 0.06 g.

$^1$H NMR (CDCl$_3$) δ: 1.06–1.10 (3H, t); 1.16–1.20 (3H, t); 1.20–1.64 (12H, m); 1.66 (3H, s); 1.70 (3H, s); 2.02–2.10 (2H, m); 2.22–2.26 (2H, q); 3.50–4.00 (2H, two broad signals); 4.52–4.56 (1H, m); 6.46 (1H, s); 7.24 (1H, m); 8.30 (1H, d); 8.40 (1H, d).

In a similar procedure to Stage 2 above, the following compounds were prepared from 2,6-dichloro-4-hydroxypyridine and the corresponding 2-bromobutyramide.

2-(2,6-Dichloropyridyloxy)- N-(4-methylpent-2-yn-4-yl)butyramide (Compound No. 23 of Table 2), colourless solid, m.p. 122–124° C., was prepared from 2,6-dichloro-4-hydroxypyridine and 2-bromo- N-(4methylpent-2-yn-4-yl)butyramide.

$^1$H NMR (CDCl$_3$) δ: 1.02-(3H, t); 1.61 (6H, s); 1.81 (3H, s); 1.99 (2H, m); 4.47 (1H, t); 6.09 (1H, br s); 6.83 (2H, s).

2-(2,6-Dichloropyridyloxy)-N-(6-methylhept-4-yn-6-yl)butyramide (Compound No. 40 of Table 2), characterised by the $^1$H NMR spectrum (incomplete due to overlapping peaks with NMR solvent): $^1$H NMR (CD$_3$CN) δ: 0.90(3H, t); 0.94 (3H, t); 1.21(2H, m); 1.48(3H, s); 1.49 (3H, s); 4.52-(1H, t); 6.71H, br s); 6.90 (2H, s), was prepared from 2,6-dichloro-4-hydroxypyridine and 2-bromo N-(6-methylhept-4-yn-6-yl)butyramide (itself prepared from 2-bromobutyryl bromide and 6-amino-6-methylheptyne hydrochloride).

EXAMPLE 11

This Example illustrates the preparation of (a) 2-(5-chloro-3-pyridyloxy)-N-(1-methoxy-4-methylpent-2-ynyl) butyramide (Compound No 49 of Table 1) and (b) 2-(5-chloro-3-pyridyloxy)-N-(1-tert.butyldimethylsilyloxy-4-methylpent-2-yn-4-yl)butyramide (Compound No 159 of Table 1)

Stage 1: Preparation of 1-(1-hydroxymethylpent-2-yn-4-yl)-2,2,5,5-tetramethyl-1-aza-2,5-disilacyclopentane Step 1: Preparation of 4-amino-1-hydroxy-4-methylpent-2-yne hydrochloride 1-(1,1-Dimethyl-2-propynyl)-2,2,5,5-tetramethyl-1-aza-2,5-disilacyclopentane (22.6 g) in dry tetrahydrofuran (250 ml) was cooled to −50° C. under an atmosphere of nitrogen with stirring and a solution of n-butyl lithium (44 ml, 2.5M solution in hexanes) was added dropwise over 10 minutes. The mixture was stirred for 0.5 hour, allowed to warm to −20° C. then formaldehyde gas was bubbled through the mixture until no starting material remained as determined by glc analysis. On completion of reaction the mixture was treated with water, the ether phase separated, the aqueous phase extracted with ethyl acetate (twice) and the organic extracts combined and washed with water (three times). The organic extract was dried over magnesium sulphate and evaporated under reduced pressure to give (1-hydroxy-4-methylpent-2-yn-4-yl)- 2,2,5,5-tetramethyl-1-aza-2,5-disilacyclopentane, 24.96 g, as a pale yellow liquid.

$^1$H NMR (CDCl$_3$) δ: 0.00 (12H, s); 0.46 (4H, s); 1.32-(6H, s); 4.08 (2H, s); OH not observed.

Step 2

The product from Step 1 (24.96 g) was treated with dilute aqueous hydrochloric acid (300 ml) and stired at ambient temperature for 0.5 hour. The mixture was washed with diethyl ether (twice), the aqueous phase was evaporated under reduced pressure, distilled with toluene (twice) to remove residual water and the residual solid obtained was triturated with hexane to give 4-amino-1-hydroxymethyl-pent-2-yne hydrochloride, 13.1 g, as a cream coloured solid.

$^1$H NMR (CDCl$_3$) δ: 1.48 (6H, s); 4.06 (2H, s); 5.32-(1H, s); 8.64 (3H, s).

Stage 2: Preparation of 4-amino-1-tert.-butyldimethylsilyloxymethylpent-2-yne

4-Amino-1-hydroxy-4-methylpent-2-yne hydrochloride (4.40 g) was dissolved in dry N N-dimethylformamide (100 ml) and triethylamine (4.44 ml) was added. The suspension was stirred at ambient temperature for 10 minutes, imidazole (4.93 g) was added followed by tert-butyldimethylsilyl chloride (5.24 g) in dry N,N-dimethylformamide (40 ml). The mixture was stirred at ambient temperature for 18 hours, diluted with water and extracted with diethyl ether (three times). The organic extracts were combined, washed with water (twice), dried over magnesium sulphate and evaporated under reduced pressure to give the required product, 6.88 g, as a yellow liquid.

$^1$H NMR (CDCl$_3$) δ: 0.04 (6H, s); 0.84 (9H, s); 1.30 (6H, s); 4.22-(2H, s).

Stage 3: Preparation of 2-(5-chloro-3-pyridyloxy)-N-(1-tert.butyldimethylsilyloxy-4-methylpent-2-yn-4-yl)butyramide (Compound No 159 of Table 1)

2-(5-Chloro-3-pyridyloxy)butyric acid (2.26 g), 4-amino-1-tert.-butyldimethylsilyloxy-4-methylpent-2-yne (2.27 g) and 4-dimethylaminopyridine (0.010 g) in dry dichloromethane (50 ml) were stirred at ambient temperature and N-dimethylaminopropyl-N'-ethylcarbodiimide hydrochloride (2.11 g) was added. The mixture was stirred at ambient temperature for 3 hours, stored for 18 hours, diluted with dichloromethane and washed with saturated aqueous sodium hydrogen carbonate (twice) then water (twice). The organic phase was dried over magnesium sulphate and evaporated under reduced pressure to give a dark yellow oil, 4.4 g, containing the required product.

$^1$H NMR (CDCl$_3$) δ: 0.10 (6H, s); 0.90 (9H, s); 1.02–1.06 (3H, t); 1.64 (3H, s); 1.66 (3H, s); 1.96–2.02-(2H, m); 4.32-(2H, s); 4.42–4.44 (1 H, t); 6.34 (1H, s); 7.24 (1H, m); 8.24 (1H, m), 8.26 (1H, m).

Stage 4

The product from Stage 3 (4.4 g) in tetrahydrofuran (100 ml) was stirred at 3–5° C. and a solution of tetra n-butylammonium fluoride (20 ml of 1M solution in tetrahydrofuran) was added dropwise over 10 minutes. On completion of addition the mixture was stirred for 0.5 hour at 0° C., 3 hours at ambient temperature then stored for 57 hours. The solvent was evaporated under reduced pressure and the residue partitioned between ethyl acetate and aqueous ammonium chloride. The organic phase was separated, washed with aqueous ammonium chloride and brine then dried over magnesium sulphate and evaporated under reduced pressure to give a yellow oil. The oil was fractionated by chromatography (silica; hexane/ethyl acetate, 2:1 by volume) to give 2-(5-chloro-3-pyridyloxy)-N-(1-hydroxy-4-methyl-pent-2-ynyl)butyramide as a colourless oil, 2.07 g.

$^1$H NMR (CDCl$_3$) δ: 1.00–1.06 (3H, t); 1.60 (3H, s); 1.96–2.02-(2H, m); 4.26 (2H, s); 4.42–4.46 (1H, t); 6.28 (1H, s); 7.28 (1H, s); 8.24 (1H, s), 8.26 (1H, s).

Stage 5

The product from Stage 4 (0.31 g) in dry N,N-dimethylformamide (5 ml) was added dropwise over 5 minutes to a suspension of sodium hydride (0.063 g, 80% dispersion in mineral oil) in dry N,N-dimethylformamide (1 ml) under an atmosphere of nitrogen at ambient temperature. The mixture was stirred for 1.25 hours and methyl iodide (0.71 g) in dry N,N-dimethylformamide (1 ml) was added over 1 minute at ambient temperature. The mixture was stirred for 1.75 hours, stored at ambient temperature for 18 hours then diluted with water and extracted with ethyl acetate (three times). The extracts were combined, washed with water (twice), dried over magnesium sulphate and evaporated under reduced pressure to give a gum. The gum was fractionated by chromatography (silica; hexane/ethyl acetate, 2:1 by volume) to give the required product as a colourless gum, 0.12 g, that solidified on storing, m.p. 81–82° C.

$^1$H NMR (CDCl$_3$) δ: 1.02–1.06 (3H, t); 1.64 (6H, s); 1.92–2.02-(2H, m); 3.36 (3H, s); 4.10 (2H, s); 4.42–4.46 (1H, t); 6.32-(1H, br s); 7.24 (1H, s); 8.24 (1H, s); 8.26 (1H, s).

EXAMPLE 12

This Example illustrates the preparation of 2-(5,6-dichloro-3-pyridyloxy)-N-(4-methylpent-2-yn-4-yl)butyramide (Compound No. 247 of Table 1)

Stage 1: Preparation of 5,6 dichloropyridin-3-ol

Step 1: Preparation of 3-amino-5,6-dichloropyridine

A solution of 2,3dichloro-5-nitropyridine (prepared as described in *Rocz. Chem.* (1968), 42 (12), 2079–2088; CAN 70:106327; 2.83 g) in propan-2-ol (40 ml) was added over 10 minutes to a stirred mixture of reduced iron powder (2.96 g), propan-2-ol (25 ml), water (15 ml) and concentrated hydrochloric acid (0.24 ml) at 70° C. The mixture was heated to reflux for 1 hour then sodium hydroxide (0.13 g) in water (1 ml) was added and the reaction filtered whilst hot through kieselguhr. The insoluble material was washed with ethyl acetate and water and the filtrates were combined and evaporated under reduced pressure to a small volume. The residue was extracted with dichloromethane (three times) and the extracts were combined, washed with water, dried over magnesium sulphate and evaporated under reduced pressure to give the required product, 2.11 g, as a pale yellow solid, m.p. 117–119° C.

$^1$H NMR (CDCl$_3$) δ: 3.80 (2H, s); 7.26 (1H, s); 7.76 (1H, s).

Step 2: Preparation of (5,6-dichloro-3-pyridyl) acetate

To a stirred solution of 3-amino-5,6-dichloropyridine (2.00 g) in 50% aqueous tetrafluoroboric acid (18 ml) at 0° C. was added dropwise a solution of sodium nitrite (0.90 g) in water (12 ml). The resulting thick suspension that formed was stirred at 0° C. for 1 hour then the diazonium salt was filtered from solution, washed with diethyl ether (3×10 ml) and sucked to dryness.

The diazonium terafluoroborate salt was suspended in acetic anhydride (20 ml) and stirred whilst the mixture was gradually heated to 70° C., during which time nitrogen gas was evolved and the solid gradually dissolved to give an orange coloured solution. The mixture was heated at 70° C. for 1.5 hours, cooled to ambient temperature and evaporated under reduced pressure to give a red oil. The oil was dissolved in diethyl ether and the solution washed with water (four times), dried over magnesium sulphate and the solvent evaporated under reduced pressure to give an oil, which was re-evaporated under reduced pressure with toluene to remove residual acetic acid/acetic anhydride, to provide (5,6-dichloro-3-pyridyl) acetate, 1.57 g, red oil.

$^1$H NMR (CDCl$_3$) δ: 2.36 (3H, s); 7.68 (1H, s); 8.16 (1H, s).

Step 3

The product from Step 2 (1.55 g) was stirred with an aqueous solution of potassium hydroxide (10 ml, 2M) at 5° C. for 0.75 hour, diluted with water and the solution taken pH 7 with acetic acid. The solid that precipitated was filtered from solution, washed with water and sucked to dryness to give the required product, 1.03 g, as an off-white solid, m.p. 178–180° C.

$^1$H NMR (d6 DMSO) δ: 7.44 (1H, d); 7.88 (1H, d).

Step 4: Preparation of 2-bromo-N-(4-methylpent-2-yn-4-yl) butyramide

4-Amino-4-methylpent-2-yne hydrochloride (5.0 g) was dissolved in dry dichloromethane (200 ml) and cooled to 3° C. with stirring. 2-Bromobutyryl bromide (6.25 g) was added followed by the dropwise addition of dry triethylamine (10.93 ml) whilst maintaining the reaction at 5° C. The suspension, which had formed during the reaction, was stirred at ambient temperature for 1 hour and water was added. The organic phase was separated, washed with water, dried over magnesium sulphate then evaporated under reduced pressure. The residue was fractionated by chromatography (silica; hexane/diethyl ether, 3:1 by volume) to give the required product, 5.2 g, as a colourless solid, mp 79–81° C.

$^1$H NMR (CDCl$_3$) δ: 1.04 (3H, t); 1.64 (6H, s); 1.84 (3H, s); 2.04–2.18 (2H, m); 4.20–4.24 (1H, m); 6.46 (1H, broad signal).

Stage 2

5,6-Dichloropyridin-3-ol was reacted with 2-bromo-N-(4methylpent-2-yn-4-yl)butyramide in a similar procedure to that described in Example 10, Stage 2 to give 2-(5,6-dichloro-3-pyridyloxy)-N-(4methylpent-2-yn-4-yl)butyramide, gum.

$^1$H NMR (CDCl$_3$) δ: 1.00–1.04 (3H, t); 1.62-(6H, s); 1.80 (3H, s); 1.94–2.02-(2H, m); 4.38–4.42-(1H, t); 6.26 (1H, s); 7.38 (1H, s); 8.04 (1H, s).

EXAMPLE 13

This Example illustrates the preparation of 2-(5,6-dichloro-3-pyridyloxy)-N-(1-methoxy-4-methylpent-2-yn-4-yl)butyramide (Compound No. 259 of Table 1)

Stage 1

Step 1: Preparation of methyl 2-(5,6-dichloro-3-pyridyloxy)butyrate 5,6-Dichloropyridin-3-ol was reacted with methyl 2-bromobutyrate using a similar procedure to that described in Example 1, Stage 1 to give methyl 2-(5,6-dichloro-3-pyridyloxy)butyrate, orange liquid.

$^1$H NMR (CDCl$_3$) δ: 1.06–1.10 (3H, t); 1.98–2.08 (2H, m); 3.78 (3H, s); 4.58–4.62-(1H, t); 7.32-(1H, s); 7.98 (1H, s).

Step 2: Preparation of methyl 2-(5,6-dichloro-3-pyridyloxy)butyric acid

Methyl 2-(5,6-dichloro-3-pyridyloxy)butyrate was hydrolysed with aqueous sodium hydroxide, using a similar procedure to that described in Example1, Stage 2 to provide 2-(5,6-dichloro-3-pyridyloxy)butyric acid as a solid, m.p. 117–118° C.

$^1$H NMR (CDCl$_3$) δ: 1.10–1.14 (3H, t); 2.20–2.12-(2H, m); 4.20–5.00 (1H, br s); 4.64–4.68 (1H, t); 7.38 (1H, s); 8.02-(1H, s).

Stage 2: Preparation of 2-(5,6-dichloro-3-pyridyloxy)-N-(1-tert.-butyldimethylsilyloxy-4-methylpent-2-yn-4-yl)butyramide In a similar procedure to that described in Example 11 Stage 3, the product from Step 2 was reacted with 4-amino-1-tert-butyldimethylsilyloxy-4-methylpent-2-yne to give 2-(5,6-dichloro-3-pyridyloxy)-N-(1-tert-butyldimethylsilyloxy-4methylpent-2-yn-4-yl)butyramide as a yellow oil.

$^1$H NMR (CDCl$_3$) δ: 0.10 (6H, s); 0.90 (9H, s); 1.00–1.04 (3H, t); 1.64 (3H, t); 1.66 (3H, s); 1.94–2.02-(2H, m); 4.32-(2H, s); 4.48–4.52-(1H, t); 6.28 (1H, s); 7.38 (1H, m); 8.04 (1H, m).

Stage 3: Preparation of 2-(5,6chloro-3-pyridyloxyl)-N-(1-hydroxy-4methylpent-2-yn-4-yl)butyramide In a similar procedure to Example11 Stage 4, 2-(5, 6dichloro-3-pyridyloxy)-N-(1-tert-butyldimethylsilyloxy-4-methylpent-2-yn-4-yl)butyramide was reacted with n-tetrabutylammonium fluoride to give 2-(5,6-dichloro-3-pyridyloxy)-N-(1-hydroxy-4-methylpent-2-yn-4-yl) butyramide as a pale yellow solid, m.p. 129–131° C.

$^1$H NMR (CDCl$_3$) δ: 1.00–1.04 (3H, t); 1.63 (3H, s); 1.65 (3H, s); 1.94–2.02-(2H, m); 2.08–2.12-(1H, t); 4.28–4.30 (2H, d); 4.40–4.44 (1H, t); 6.24 (1H, s); 7.40 (1H, s); 8.04 (1H, s).

Stage 4

In a similar procedure to that described in Example 11 Stage 5, 2-(5,6-dichloro-3-pyridyloxy)-N-(1-hydroxymethylpent-2-yn-4-yl)butyramide was reacted with methyl iodide to give 2-(5,6-dichloro-3-pyridyloxy)-N-(1-methoxy-4-methylpent-2-yn-4-yl)butyramide as a pale yellow gum.

$^1$H NMR (CDCl$_3$) δ: 1.00–1.04 (3H, t); 1.64 (6H, s); 1.94–2.02-(2H, m); 3.36 (3H, s); 4.10 (2H, s); 4.42–4.44 (1I, t); 6.28 (1H, s); 7.36 (1H, m); 8.02-(1H, m).

EXAMPLE 14

This Example illustrates the preparation of (a) 2-(5-chloro-3-pyridyloxy)-N-(2-methoxy-5-methylhex-3-yn-5-yl)butyramide (Compound No.384 of Table 1) and (b) 2-(5-Chloro-3-pyridyloxy)-N-(1-ethoxymethylpent-2-yn-4-yl)butyramide (Compound No.382 of Table 1)

Stage 1: Preparation of 5-amino-2-methoxy-5-methylhex-3-yne hydrochloride

Step 1: Preparation of 5-amino-2-hydroxy-5-methylhex-3-yne hydrochloride 1-(1,1-Dimethyl-2-propynyl)-2,2,5,5-tetramethyl-1-aza-2,5-disilacyclopentane (1.0 g) in dry tetrahydrofuran (10 ml) was cooled to −50° C. under an atmosphere of nitrogen with stirring and a solution of n-butyl lithium (2.0 ml, 2.5M solution in hexanes) was added dropwise over 2 minutes. The mixture was stirred for 0.25 hour at −50° C., allowed to warm to −20° C. then acetaldehyde (0.22 g) in tetrahydrofuran (2 ml) was added dropwise. The reaction was stirred at −20° C. for 1.5 hours, allowed to warm to ambient temperature over 1 hour and treated with water. The product was extracted with ethyl acetate (three times) and the extracts were combined, washed with water (twice) then dried over magnesium sulphate and evaporated under reduced pressure to give (2-hydroxy-5-methylhex-3-yn-5-yl)- 2,2,5,5-tetramethyl-1-aza-2,5-disilacyclopentane,1.06 g, as a yellow liquid.

$^1$H NMR (CDCl$_3$) δ: 0.00 (12H, s); 0.46 (4H, s); 1.23 (3H, d); 1.30 (6H, s); 4.32–4.36 (1H, q).

Step 2

The product from Step 1 (1.06 g) in dry tetrahydrofuran (10 ml) was cooled to −10° C. under an atmosphere of nitrogen with stirring and potassium bis(trimethylsilylamide) (0.83 g) in tetrahydrofuran (10 ml) was added over 2 minutes. The mixture was stirred at −(10 to 5)° C. for 0.75 hours. Methyl iodide (0.60 g) in tetrahydrofuran (2 ml) was added over 1 minute. The mixture was allowed to warm to ambient temperature over 1.5 hours, diluted with water and extracted with ethyl acetate (three times). The extracts were combined, dried over magnesium sulphate and evaporated under reduced pressure to give (2-methoxy-5-methylhex-3-yn-5-yl)-2,2,5,5-tetramethyl-1-aza-2,5-disilacyclopentane, 1.2 g, as a yellow liquid.

Step 3

(2-Methoxy-5-methylhex-3-yn-5-yl)-2,2,5,5-tetramethyl-1-aza-2,5-disilacyclopentane (1.2 g) was stirred with dilute aqueous hydrochloric acid (12 ml) for 0.25 hours. The aqueous phase was washed with diethyl ether (twice) and the evaporated under reduced pressure. The residue was evaporated with toluene (twice) to remove residual water to give 5-amino-2-methoxy-5-methylhex-3-yne hydrochloride, 0.54 g, as a yellow solid.

$^1$H NMR (CDCl$_3$) δ: 1.43 (3H, d); 1.78 (6H, s); 4.06–4.12 (1H, q), 8.80–9.00 (3H, s).

Stage: 2

5-Amino-2-methoxy-5-methylhex-3-yne hydrochloride was reacted with 2-(5-chloro-3-pyridyloxy)butyric acid in a similar procedure to Example 1, Stage 3 to give 2-(5-chloro-3-pyridyloxy)-N-(2-methoxy-5-methylhex-3-yn-5-yl)butyramide as a yellow oil.

$^1$H NMR (CDCl$_3$) δ: 1.02–1.06 (3H, t); 1.38–1.40 (3H, d); 1.64 (6H, s); 1.96–2.02-(2H, m); 3.36–3.38 (3H, d); 4.06–4.12-(1H, q); 4.44–4.48 (1H, t); 6.34 (1H, s); 7.26 (1H, m); 8.24–8.28 (2H,d).

In a similar procedure to Example 1, Stage 3, the following compound was prepared from 2-(5-chloro-3-pyridyloxy) butyric acid and the corresponding amine.

2-(5-Chloro-3-pyridyloxy)-N-(1-ethoxy-4methylpent-2-yn-4-yl)butyramide (Compound No. 382 of Table 1), colourless gum, $^1$H NMR (CDCl$_3$) δ: 1.02–1.06 (3H, t); 1.22–1.26 (3H, t); 1.66 (6H, s); 1.96–2.02-(2H, q); 3.52–3.58 (2H, q); 4.16 (2H, s); 4.42–4.46 (1H, t); 6.34 (1H, s); 7.24 (1H, m); 8.24–8.28 (2H, m) was prepared from 4-amino-1-ethoxy-4-methylpent-2-yne hydrochloride [$^1$H NMR (CDCl$_3$) δ: 1.20–1.24 (3H, t); 1.78 (6H, s); 3.56–3.62 (2H, q); 4.16 (2H, s); 8.86 (3H, br s)]. The 4-amino-1-ethoxy-4-methylpent-2-yne hydrochloride was prepared from (1-hydroxymethylpent-2-yn-4-yl)-2,2,5,5-tetramethyl-1-aza-2,5-disilacyclopentane and ethyl iodide.

EXAMPLE 15

This Example illustrates the preparation of (−) 2-(5-bromo-3-pyridyloxy)-N-(4-methylpent-2-yn-4-yl)butyramide (the (−) isomer of Compound 13 of Table 1)

Step 1: Preparation of homochiral 2-(5-bromo-3-pyridyloxy)butyric acid

A racemic mixture of methyl 2-(5-bromo-3-pyridyloxy) butyrate was selectively hydrolysed using *Pseudomonas fluorescens* lipase to give homochiral 2-(5-bromo-3-pyridyloxy) butyric acid e.e. >99% by chiral hplc.

Step 2: Preparation of homochiral 2-(5-bromo-3-pyridyloxy)butyric acid chloride.

Homochiral 2-(5-bromo-3-pyridyloxy)butyric acid (0.12 g) was mixed with thionyl chloride (0.5 ml) and heated to reflux with stirring for 2 hours. The excess thionyl chloride was evaporated under reduced pressure to give the required acid chloride, 0.11 g, as a pale yellow oil, that was used in the next Step without further purification.

Step 3

To a stirred solution of the product from Step 2 (0.11 g) in dry dichloromethane (2.5 ml) at −5° C. was added 4-amino-4-methylpent-2-yne hydrochloride (0.061 g) followed by dropwise addition of dry triethylamine (0.21 ml) over 1 minute. The suspension formed was stirred for 0.5 hour at 0° C., 2 hour at ambient temperature then stored for 18 hours. The mixture was diluted with further dichloromethane, washed with saturated sodium hydrogen carbonate and water then dried over magnesium sulphate and evaporated under reduced pressure to give a gum. The gum was triturated with hexane to give the required product, 0.078 g, as a pale brown solid, m.p. 95–97° C.; [α] recorded at 26.5° C., 589 nm in methanol=(−)51.2°; optical purity >98% by $^1$H NMR using homochiral 2,2,2-trifluoro-1-(9-anthryl)ethanol as co-solvent

EXAMPLE 16

This Example illustrates the preparation of 2-(5-cyano-3-pyridyloxy)-N-(4-methylpent-2-yn-4-yl) butyramide (Compound No. 342 of Table 1)

Step 1: Preparation of methyl 2-(5-cyano-3-pyridyloxy)butyrate

A solution of methyl 2-(5-bromo-3-pyridyloxy)butyrate (1.37 g) and copper (1) cyanide (0.67 g) in dry N-methylpyrollidin-2-one (5 ml) was stirred at 150° C. under an atmosphere of nitrogen for 3.25 hours then cooled to ambient temperature and stored for 18 hours. The mixture was diluted with water and extracted with ethyl acetate (four times). The extracts were combined, washed with water (three times), dried over magnesium sulphate and evaporated under reduced pressure to give a liquid which was fractionated by chromatography (silica; ethyl acetate) to give the required product, 0.29 g, as an orange oil.

$^1$H NMR (CDCl$_3$) δ: 1.08–1.14 (3H, t); 2.02–2.10 (2H, m); 3.80 (3H, s); 4.62–4.66 (1H, t); 7.34 (1H, m); 8.50–8.54 (2H, m).

Step 2: Preparation of 2 (5-cyano-3-pyridyloxy)butyric acid

The product from Step 1 (0.29 g) was dissolved in propan-2-ol (5 ml) containing sodium hydroxide (0.053 g) and water (2 ml). The mixture was stirred at ambient temperature for 20 minutes, evaporated under reduced pressure to a small volume and diluted with water. The solution was acidified with dilute aqueous hydrochloric acid and extracted with ethyl acetate (three times). The extracts were combined, washed with water (three times), dried over magnesium sulphate and evaporated under reduced pressure to give the required product, 0.25 g, as a gum.

Step 3

The product from Step 2 was condensed with 4-amino-4-methylpent-2-yne hydrochloride in a similar procedure to that described in Example 1 Stage 3 to give the required product as a colourless solid, m.p. 112–113° C.

$^1$H NMR (CDCl$_3$) δ: 1.00–1.06 (3H, t); 1.60 (6H, s); 1.80 (3H, s); 1.98–2.04 (2H, m); 4.44–4.48 (1H, t); 6.22-(1H, s); 7.44 (1H, s); 8.54 (2H, s).

EXAMPLE 17

This Example illustrates the preparation of 2-(4-methylthio-5-phenoxy-3-pyridyloxy)-N-(4-methylpent-2-yn-4-yl)butyramide (Compound No 263 of Table 1)

Step 1: Preparation of 3-bromo-5-phenoxypyridine 3,5-Dibromopyridine (4.74 g), phenol (1.88 g), anhydrous potassium carbonate (3.04 g), copper bronze (0.1 g) in dry N,N-dimethylformamide (20 ml) were stirred under an atmosphere of nitrogen at 145–150° C. for 4.25 hours then cooled and poured into water. The mixture was extracted with diethyl ether (three times), the extracts were combined, washed with water (three times) then dried over magnesium sulphate and evaporated under reduced pressure to give an oil. The oil was fractionated by chromatography (silica; hexane: diethyl ether; 2:1 by volume) to give the required product, 1.70 g, as a colourless oil.

$^1$H NMR (CDCl$_3$) δ: 7.02–7.06 (2H, d); 7.20–7.24 (1H, t); 7.38–7.42-(3H, m); 8.32-(1H, s); 8.40 (1H, s).

Step 2: Preparation of 3-hydroxy-4-methylthio-5-phenoxypyridine

3-Bromo-5-phenoxypyridine (0.50 g) and potassium superoxide (1.42 g) in dry dimethyl sulphoxide (100 ml) containing 1,4,7,10,13,16-hexaoxacyclooctadecane (3.20 g) were stirred at ambient temperature under an atmosphere of nitrogen for 18 hours. The solvent was evaporated under reduced pressure to a small volume and the mixture diluted with water, washed with ethyl acetate (twice) and the basic aqueous phase was acidified to pH 4 with dilute aqueous hydrochloric acid. The mixture was extracted with ethyl acetate (three times), the extracts were combined and washed with water (four times), dried over magnesium sulphate and evaporated under reduced pressure to give an oil. The oil was fractionated by chromatography (silica; diethyl ether) to give the required product, 0.19 g, as a colourless solid, m.p. 131–133° C.

$^1$H NMR (CDCl$_3$) δ: 2.42-(3H, s); 7.02–7.04 (2H, d); 7.14–7.20 (1H, t); 7.36–7.40 (2H, m); 7.80 (1H, s); 8.20 (1H, s).

Step 3

3-Hydroxymethylthio-5-phenoxypyridine was reacted with 2-bromo-N-(4-methylpent-2-yn-4-yl)butyramide in a similar procedure to that described in Example10 Stage 2 to give 2-(4-methylthio-5-phenoxy-3-pyridyloxy)- N-(4-methylpent-2-yn-4-yl)butyramide as a pale yellow oil.

$^1$H NMR (CDCl$_3$) δ: 1.06–1.10 (3H, t); 1.66 (3H, s); 1.67 (3H, s); 1.80 (3H, s); 2.10–2.16 (2H, m); 2.54 (3H, s); 4.72–4.74 (1H, m); 6.98–7.00 (2H, d);.7.14–7.18 (1H, t); 7.24 (1H, br s); 7.34–7.40 (2H, t); 7.92-(1H, s); 8.04 (1H, s).

EXAMPLE 18

This Example illustrates the preparation of 2-(5-chloro-3-pyridyloxy)- N-(4-methylpent-2-yn-4-yl)-3-methoxypropionamide (Compound No 21 in Table 1)

Stage 1: Preparation of 2-bromo-N-(4-methylpent-2-yn-4-yl) 3-methoxypropionamide Step1: Preparation of methyl 2-bromo-3-methoxypropionate Methyl 2,3-dibromopropionate (21.9 g) and trimethylamine N-oxide (0.1 g) in methanol (8 ml) were cooled to −5° C. with stirring under an atmosphere of nitrogen. A solution of sodium methoxide [freshly prepared from sodium (2.25 g) and methanol (24 ml)] was added dropwise over 15 minutes to the mixture, which was maintained below 0° C. by cooling. On completion of the addition, the mixture was stirred for a further 30 minutes and acetic acid (1 ml) was added followed by diethyl ether (100 ml). The mixture was filtered to remove insoluble salts and the filtrate evaporated under reduced pressure to give an oil, which was re-dissolved in a small volume of diethyl ether and re-filtered. The filtrate was evaporated under reduced pressure to give the required product, 17.4 g, as a pale yellow oil.

$^1$H NMR (CDCl$_3$) δ: 3.41 (3H, s); 3.74(1H, dd); 3.82-(3H, s); 3.92-(1H, dd); 4.34 (1H, dd).

Step 2: Preparation of 2-bromo-3-methoxypropionic acid

Methyl 2-bromo-3-methoxypropionate (1.00 g) in tetrahydrofuran (8 ml) was stirred at 10° C. and lithium hydroxide monohydrate (0.21 g) in water (1.5 ml) was added dropwise. On completion of the addition, the mixture was stirred for 1.5 hours. The colourless solution was evaporated under reduced pressure to a small volume and the aqueous solution was taken to pH 3 with dilute sulphuric acid. The mixture was extracted with diethyl ether (50 ml) and the organic phase separated, washed with brine, dried over magnesium sulphate and evaporated under reduced pressure to give the required product, 0.6 g, as a colourless liquid.

$^1$H NMR (CDCl$_3$) δ: 3.45 (3H, s); 3.78 (1H, m); 3.92-(1H, m); 4.38 (1H, m); 6.65 (1H, broad signal).

Step 3: Preparation of 2-bromo-N-(4-methylpent-2-yn-4-yl) 3-methoxypropionamide

2-Bromo-3-methoxypropionic acid (0.366 g) was dissolved in dry dichloromethane (4 ml) containing dry N,N-dimethylformamide (0.05 ml) with stirring and oxalyl chloride (0.254 g) was added. The mixture was stirred at ambient temperature for 2 hours then evaporated under reduced pressure to give 2-bromo-3-methoxypropionic acid chloride (C=O, v1780cms$^{-1}$). The acid chloride was dissolved in dry dichloromethane (6 ml) and 4-amino-4-methylpent-2-yne hydrochloride (0.267 g) was added. The mixture was cooled to 3° C. and triethylamine (0.404 g) was added dropwise, keeping the reaction temperature between 0–5° C. The suspension that had formed was stirred at ambient temperature for 1 hour, diluted with further dichloromethane, washed with hydrochloric acid (2M) and the organic phase separated, dried over magnesium sulfate then evaporated under reduced pressure to give a gum. The gum was fractionated by chromatography (silica: hexane/ethyl acetate, 3:2 by volume) to give the required product, 0.300 g, as a colourless solid.

$^1$H NMR (CDCl$_3$) δ: 1.63 (6H, s); 1.82-(3H, s); 3.44 (3H, s); 3.88 (2H, m); 4.32-(1H, m); 6.62-(1H, s).

Stage 2

3-Chloro-5-hydroxypyridine (0.074 g), anhydrous potassium carbonate (0.087 g) and 2-bromo-N-(4-methylpent-2-yn-4-yl)-3-methoxypropionamide (0.150 g) in dry N,N-dimethylformamide (3 ml) were stirred at 80° C. for 5 hours. The mixture was allowed to cool to ambient temperature and stored for 2 days. The mixture was poured into water, extracted with ethyl acetate and the organic phases were combined, washed with water, dried over magnesium sulphate and evaporated under reduced pressure to give a gum. The gum was fractionated by chromatography (silica; ethyl acetate:hexane, 2:3 by volume) to give a colourless gum that was dissolved in diethyl ether and extracted with aqueous hydrochloric acid (3M). The aqueous acidic fraction was collected and treated with potassium carbonate until basic then extracted with diethyl ether. The ether extracts were combined, dried over magnesium sulphate and evaporated under reduced pressure to give the required product, 0.094 g, as a colourless gum.

$^1$H NMR (CDCl$_3$) δ: 1.53 (3H, s); 1.55 (3H, s); 1.72-(3H, s); 3.34 (3H, s); 3.72–3.82-(2H, m); 4.56 (1H, m); 6.47 (1H, s); 7.27 (1H, m); 8.03 (2H, m).

EXAMPLE 19

This Example illustrates the preparation of (5-chloro-3-pyridyloxy)-N-(1-methoxy-4-methyl-pent-2-yn-4-yl)-3-methoxypropionamide (Compound No 53 of Table 1)

Step 1: Preparation of 2-bromo-N-(1-methoxymethylpent-2-yn-4-yl)-3-methoxypropionamide 2-Bromo-N-(1-methoxy-4-methylpent-2-yn-4-yl)-3-methoxypropionamide was prepared in a similar manner to 2-bromo-N-(4-methylpent-2-yn-4-yl) 3-methoxypropionamide described in Example 18, Step 3 using 4-amino-1-methoxy-4-methylpent-2-yne hydrochloride in place of 4-amino-4-methylpent-2-yne hydrochloride.

$^1$H NMR (CDCl$_3$) δ: 1.68 (6H, s); 3.38 (3H, s); 3.44 (3H, s); 3.82–3.92-(2H, m); 4.10 (2H, s); 4.33 (1H, t); 6.64 (1H, broad s), yellow gum.

Step 2

2-Bromo-N-(1-methoxy-4-methylpent-2-yn-4-yl)-3-methoxypropionamide was reacted with 3-chloro-5-hydroxypyridine in a similar procedure to Example 10, Stage 2 to give the required product as a pale yellow oil.

$^1$H NMR (CDCl$_3$) δ: 1.58 (3H, s); 1.60 (3H, s); 3.30 (3H, s); 3.34 (3H, s); 3.74–3.82-(2H, m); 4.04 (2H, s); 4.55 (1H, m); 6.44 (1H, br s); 7.26 (1H, m); 8.22-(2H, m).

EXAMPLE 20

This Example illustrates the preparation of 2-(5-ethynyl-3-pyridyloxy)-N-(4-methylpent-2-yn-4-yl) butyramide (Compound No. 358 of Table 1)

Stage 1: Preparation of 2-(5-trimethylsilylethynyl-3-pyridyloxy)-N-(4-methylpent-2-yn-4-yl)butyramide 2-(5-Bromo-3-pyridyloxy)-N-(4-methylpent-2-yn-4-yl) butyramide (0.40 g), trimethylsilylacetylene (0.24 ml), copper (I) chloride (0.015 g) and palladium dichloride bis (triphenyl)phosphine (0.030 g) in dry triethylamine (4 ml) were sealed in a glass tube and heated to 90° C. for 3 hours. The mixture was cooled to ambient temperature and stored for 18 hours. Further trimethylsilylacetylene (0.24 ml) and palladium dichloride bis(triphenyl)-phosphine (0.030 g) were added and the mixture re-heated in the sealed tube for another 5.5 hours. The reaction mixture was cooled to ambient temperature, stored for 72 hours, diluted with diethyl ether and washed with water (three times). The organic phase was separated, dried over magnesium sulphate and evaporated under reduced pressure to give a dark yellow gum, ca. 0.4 g, containing the required product, which was used in the next Stage without further purification.

Stage 2

The product from Stage 1 (0.4 g) was dissolved in dichloromethane (10 ml) with stirring and a solution of tetra n-butylammonium fluoride in tetrahydrofuran (1.4 ml, 1M) was added. The mixture was stirred at ambient temperature for 2 hours then stored for 18 hours. Further dichloromethane was added and the organic phase was washed with water (twice), dried over magnesium sulphate and evaporated under reduced pressure to give a gum that was fractionated by chromatography (silica; diethyl ether/hexane, 2:1 by volume) to give the required product, 0.21 g, as a pale brown oil.

$^1$H NMR (CDCl$_3$) δ: 1.02–1.06 (3H, t); 1.62-(6H, s); 1.82-(3H, s); 1.96–2.02-(2H, q); 3.22-(1H, s); 4.42–4.46 (1H, t); 6.34 (1H, s); 7.30 (1H, m); 8.32-(1H, d); 8.40 (1H, d).

EXAMPLE 21

This Example illustrates the preparation of 2-(5-ethenyl-3-pyridyloxy)-N-(4-methylpent-2-yn-4-yl) butyramide 2-(5-Bromo-3-pyridyloxy)-N-(4-methylpent-2-yn-4-yl) butyramide (0.34 g), tetrakis(triphenylphosphine) palladium (0) (0.0.02 g) and tributylvinyl tin(0.38 g) in dry toluene (5 ml) were stirred and heated to reflux for 9 hours under an atmosphere of nitrogen. The mixture was cooled to ambient temperature, stored for 72 hours then evaporated under reduced pressure to give a gum that was fractionated by chromatography (silica; diethyl ether) to give the required product, 0.16 g, as a colourless gum.

$^1$H NMR (CDCl$_3$) δ: 1.02–1.08 (3H, t); 1.60 (3H, s); 1.62-(3H, s); 1.80 (3H, s); 1.96–2.04 (2H, m); 5.40–5.44 (1H, d); 5.80–5.84 (1H, m); 6.38 (1H, s); 6.64–6.72-(1H,m); 7.24 (1H, m); 8.24 (1H, d); 8.30 (1H, d).

EXAMPLE 22

This Example illustrates the preparation of (a) 2-(5-acetyl-3-pyridyloxy)-N-(4-methylpent-2-yn-4-yl) butyramide (Compound No. 326 of Table 1) and (b), 2-[5-(1-ethoxyethen-1-yl)-3-pyridyloxy]-N-(4-methylpent-2-ynyl)butyramide (Compound No. 378 of Table 1)

Stage 1

In a similar manner to Example 21, 2-[5-(1-ethoxyethen-1-yl)-3-pyridyloxy]-N-(4-methylpent-2-yn-4-yl)butyramide (Compound No. 378 of Table 1), pale yellow oil, was prepared from 2-(5-bromo-3-pyridyloxy)-N-(4-methylpent-2-yn-4-yl)butyramide using tributyl(1-ethoxyvinyl)tin in place of tributylvinyltin.

$^1$H NMR (CDCl$_3$) δ: 1.00–1.06 (3H, t); 1.40–1.46 (3H, t); 1.60 (31, s); 1.64 (3H, s); 1.80 (3H, s); 1.94–2.02-(2H, m); 3.90–3.94 (2H, m); 4.30 (11H, m); 4.46–4.50 (1H, m); 4.70 (1H, m); 6.42-(1H, s); 7.72-(1H,m); 8.28 (1H, m); 8.54 (1H, s).

Stage 2

The product from Stage 1 (0.32 g) was dissolved in tetrahydrofuran (10 ml) and aqueous hydrochloric acid (2.5 ml, 2M) was added. The mixture was stirred at ambient temperature for 1.25 hours then stored for 18 hours. The mixture was evaporated under reduced pressure to a small volume, treated with excess aqueous sodium hydrogen carbonate then extracted with ethyl acetate (three times). The extracts were combined, washed with water, dried over magnesium sulphate then evaporated under reduced pressure to give the required product, 0.27 g, as a yellow oil.

$^1$H NMR (CDCl$_3$) δ: 1.10 (3H, s); 1.12-(3H, s); 1.80 (3H, s); 1.98–2.04 (2H, m); 2.64 (3H, s); 4.54–4.56 (1H, m); 6.36 (1H, s); 7.74 (1H, m); 8.52-(1H, d); 8.84 (1H, d).

EXAMPLE 23

This Example illustrates the fungicidal properties of compounds of formula (I).

The compounds were tested in a leaf disk assay, with methods described below. The test compounds were dissolved in DMSO and diluted into water to 200 ppm. In the case of the test on *Pythium ultimum*, they were dissolved in DMSO and diluted into water to 20 ppm.

*Erysiphe graminis* f.sp. *hordei* (barley powdery mildew): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Erysiphe graminis* f.sp. *tritici* (wheat powdery mildew): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Puccinia recondita* f.sp. *tritici* (wheat brown rust): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed nine days after inoculation as preventive fungicidal activity.

*Septoria nodorum* (wheat glume blotch): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyrenophora teres* (barley net blotch): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyricularia oryzae* (rice blast): Rice leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Botrytis cinerea* (grey mould): Bean leaf disks were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Phytophthora infestans* (late blight of potato on tomato): Tomato leaf disks were placed on water agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Plasmopara viticola* (downy mildew of grapevine): Grapevine leaf disks were placed on agar in a 24-well plate and sprayed a solution of the test compound. After allowing to dry completely, for between 12 and 24 hours, the leaf disks were inoculated with a spore suspension of the fungus. After appropriate incubation the activity of a compound was assessed seven days after inoculation as preventive fungicidal activity.

*Pythium ultimum* (Damping off): Mycelial fragments of the fungus, prepared from a fresh liquid culture, were mixed into potato dextrose broth. A solution of the test compound in dimethyl sulphoxide was diluted with water to 20 ppm then placed into a 96-well microtiter plate and the nutrient broth containing the fungal spores was added.

The test plate was incubated at 24° C. and the inhibition of growth was determined photometrically after 48 hours.

The following compounds gave at least 70% control of *Plasmopara viticola* at 200 ppm: Compounds Nos. 1, 3, 8, 10, 13, the (−) isomer of 13, 14, 15, 21, 49, 53, 120, 128, 136, 247, 259, 263, 342 and 358 of Table 1 and 23 and 39 of Table 2.

The following compounds gave at least 70% control of *Phytophthora infestans* at 200 ppm: Compounds Nos. 3, 11, the (−) isomer of 13, 15, 53, 128, 263, 326, 342, 374 and 378 of Table 1.

The following compounds gave at least 70% control of *Pythium ultimum* at 20 ppm: Compounds Nos. 8, the (−) isomer of 13, and 374 of Table 1 and 23 of Table 2.

The invention claimed is:

1. A compound of the general formula (I):

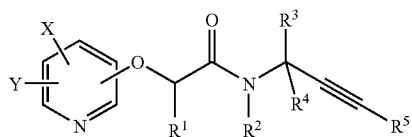
(I)

wherein X is H, $C_{1-4}$ alkyl, halo($C_{1-4}$)alkyl or CN; Y is H, halo, $C_{1-4}$ alkyl or halo($C_{1-4}$)alkyl; $R^1$ is methyl, ethyl, n-propyl or methoxymethyl; $R^2$ is H, methyl, ethyl, n-propyl, methoxymethyl or ethoxymethyl; $R^3$ and $R^4$ are both methyl or $R^3$ is methyl and $R^4$ is ethyl; $R^5$ is halo, $C_{1-4}$ alkyl, hydroxy($C_{1-4}$)alkyl or $C_{1-4}$ alkoxy($C_{1-4}$)alkyl; and the alkanoic acid amide side chain is attached to the 3-position of the pyridine ring.

2. A process for preparing a compound of formula (I) according to claim 1 comprising one of the following steps:

a. reacting an appropriately substituted pyridinol of the formula:

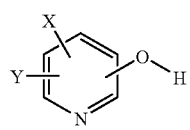
(II)

with a compound of formula

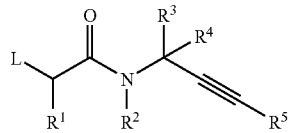
(III)

where L represents a halogen or sulphonate ester, in the presence of a suitable base and an aprotic solvent, to form a compound of formula (I); or b. condensing a compound of formula

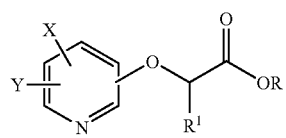
(XI)

wherein R is H, with the amine of formula

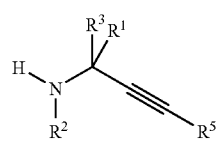
(V)

using suitable activating reagents selected from 1-hydroxybenztriazole and N-(3-dimethylaminopropyl)-N'-ethyl carbodiimide hydrochloride, to form a compound of formula (I); or c. reacting an acid halide of formula

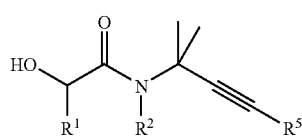
(XIII)

with the amine of formula

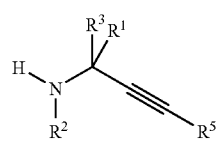
(V)

in a suitable solvent, in the presence of a tertiary amine, and an activating agent, to form a compound of formula (I); or d. reacting a compound of formula

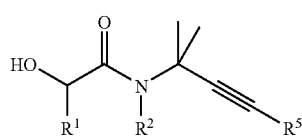
(XVI)

with a pyridinol of formula

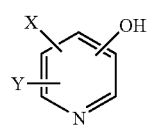
(II)

under Mitsunobu conditions using a phosphine and an azoester to form a compound of formula (I).

3. A fungicidal composition comprising a fungicidally effective amount of a compound according to claim 1 and a suitable carrier or diluent therefor.

4. A method of combating or controlling phytopathogenic fungi which comprises applying to a plant, to a seed of a plant, to the locus of the plant or seed or to soil or to any other plant growth medium, a fungicidally effective amount of a compound according to claim 1.

5. A method of combating or controlling phytopathogenic fungi which comprises applying to a plant, to a seed of a plant, to the locus of the plant or seed or to soil or to any other plant growth medium, a fungicidally effective amount of a composition according to claim 3.

* * * * *